US008309690B2

(12) United States Patent
Allan et al.

(10) Patent No.: US 8,309,690 B2
(45) Date of Patent: Nov. 13, 2012

(54) INTEGRATED APPROACH FOR GENERATING MULTIDOMAIN PROTEIN THERAPEUTICS

(75) Inventors: Christian Allan, Brookeville, MD (US); Herren Wu, Boyds, MD (US); Jeffrey Swers, Rockville, MD (US); William Dall'Acqua, Gaithersburg, MD (US)

(73) Assignee: MedImmune, LLC, Gaithersburg, MD (US)

(*) Notice: Subject to any disclaimer, the term of this patent is extended or adjusted under 35 U.S.C. 154(b) by 661 days.

(21) Appl. No.: 11/993,680

(22) PCT Filed: Jun. 30, 2006

(86) PCT No.: PCT/US2006/025590
§ 371 (c)(1),
(2), (4) Date: Jan. 12, 2010

(87) PCT Pub. No.: WO2007/005612
PCT Pub. Date: Jan. 11, 2007

(65) Prior Publication Data
US 2010/0105873 A1   Apr. 29, 2010

Related U.S. Application Data

(60) Provisional application No. 60/696,113, filed on Jul. 1, 2005, provisional application No. 60/788,692, filed on Apr. 4, 2006.

(51) Int. Cl.
*C07K 16/00* (2006.01)
(52) U.S. Cl. .................................. 530/387.3; 424/130.1
(58) Field of Classification Search .................... None
See application file for complete search history.

(56) References Cited

U.S. PATENT DOCUMENTS

| 5,624,821 | A | 4/1997 | Winter et al. |
|---|---|---|---|
| 5,648,260 | A | 7/1997 | Winter et al. |
| 5,677,425 | A | 10/1997 | Bodmer et al. |
| 5,869,046 | A | 2/1999 | Presta et al. |
| 5,885,573 | A | 3/1999 | Bluestone et al. |
| 5,968,742 | A | 10/1999 | Bandman et al. |
| 6,027,910 | A | 2/2000 | Klis et al. |
| 6,121,022 | A | 9/2000 | Presta et al. |
| 6,165,745 | A | 12/2000 | Ward et al. |
| 6,194,551 | B1 | 2/2001 | Idusogie et al. |
| 6,277,375 | B1 | 8/2001 | Ward et al. |
| 6,737,056 | B1 | 5/2004 | Presta |
| 6,821,505 | B2 | 11/2004 | Ward |
| 7,247,302 | B1 | 7/2007 | Rosok |
| 7,416,726 | B2 | 8/2008 | Ravetch |
| 7,597,889 | B1 | 10/2009 | Armour et al. |
| 2001/0036459 | A1 | 11/2001 | Ravetch |
| 2002/0147311 | A1 | 10/2002 | Gilles et al. |
| 2003/0157108 | A1 | 8/2003 | Presta |
| 2003/0190311 | A1 | 10/2003 | Dall'Acqua et al. |
| 2004/0002587 | A1 | 1/2004 | Watkins et al. |
| 2004/0132101 | A1 | 7/2004 | Lazar et al. |
| 2005/0032114 | A1 | 2/2005 | Hinton |
| 2005/0037000 | A1 | 2/2005 | Stavenhagen |
| 2005/0054832 | A1 | 3/2005 | Lazar et al. |
| 2005/0064514 | A1 | 3/2005 | Stavenhagen |
| 2005/0152894 | A1 | 7/2005 | Krummen |
| 2005/0215768 | A1 | 9/2005 | Armour |
| 2005/0244403 | A1 | 11/2005 | Lazar et al. |
| 2006/0024298 | A1 | 2/2006 | Lazar et al. |
| 2006/0039904 | A1 | 2/2006 | Wu et al. |
| 2006/0040325 | A1 | 2/2006 | Wu et al. |
| 2006/0067930 | A1 | 3/2006 | Adams |
| 2006/0074225 | A1 | 4/2006 | Chamberlain |
| 2006/0134105 | A1 | 6/2006 | Lazar |
| 2006/0173170 | A1 | 8/2006 | Chamberlain |
| 2006/0235208 | A1 | 10/2006 | Lazar et al. |
| 2006/0275283 | A1 | 12/2006 | van Vlijmen |
| 2007/0148164 | A1 | 6/2007 | Farrington |
| 2007/0148167 | A1 | 6/2007 | Strohl |
| 2007/0224188 | A1 | 9/2007 | Allan |
| 2008/0089892 | A1 | 4/2008 | Allan |

FOREIGN PATENT DOCUMENTS

| WO | WO-94-29351 | 12/1994 |
|---|---|---|
| WO | WO 98/05787 | 2/1998 |
| WO | WO-98-23289 | 6/1998 |
| WO | WO 99/58572 | 11/1999 |
| WO | WO 01/58957 | 8/2001 |
| WO | WO 03/074679 | 9/2003 |
| WO | WO 03/104415 | 12/2003 |

(Continued)

OTHER PUBLICATIONS

Ueda et al. (Journal of Molecular Catalysis, vol. 28, pp. 173-179, 2004) cited on IDS filed Oct. 20, 2011.*
Dall'Acqua et al. (Journal of Immunology, vol. 169, pp. 5171-5180, 2002).*
Alegre, M. L., et al. "A Non-Activating "Humanized" Anti-CD3 Monoclonal Antibody Retains Immunosuppressive Properties in Vivo." *Transplantation* (1994) 57: 1537-43.
Armour, K. L., et al. "Recombinant Human IgG Molecules Lacking Fcgamma Receptor I Binding and Monocyte Triggering Activities." *Eur.J.Immunol.* (1999) 29: 2613-24.
Bastida-Corcuera et al., "Differential complement activation by bovine IgG2 allotypes." *Vet Immunol Immunopathol* (1999) 71:115-123.

(Continued)

*Primary Examiner* — Laura B Goddard
*Assistant Examiner* — Meera Natarajan
(74) *Attorney, Agent, or Firm* — MedImmune, LLC

(57) ABSTRACT

The invention provides method for therapeutic protein drug development that incorporates therapeutic and/or formulation and/or manufacturing considerations in the early screening process. The approach involves screening a plurality of different variants of a domain that have been determined to have the desired therapeutic property to identify one or more variants that have desired therapeutic and/or formulation characteristics, and constructing the full multidomain proteins using the identified domain variants. The present invention also provides a method for determining the shelf life of multidomain proteins in formulations. The method comprises determining a thermal denaturation and/or renaturation curve of a domain of the protein whose unfolding leads to aggregation of the protein in a solution. The method evaluates the shelf life of the multidomain protein based on the denaturation/renaturation curve. The invention also provides methods for engineering multidomain proteins to improve their therapeutic and/or formulation characteristics.

25 Claims, 36 Drawing Sheets

FOREIGN PATENT DOCUMENTS

Figure 1:
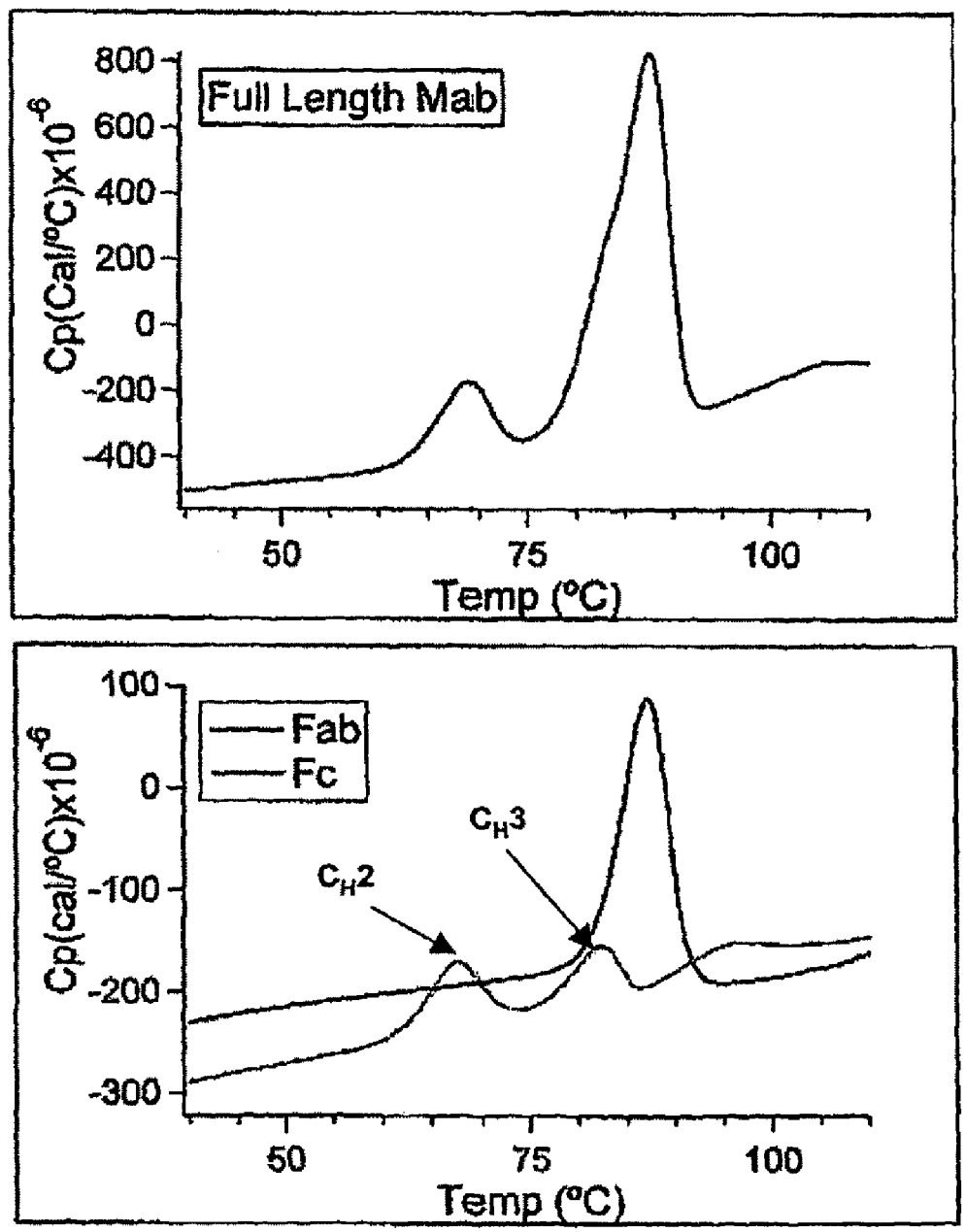

| | | |
|---|---|---|
| WO | WO 2004/016750 | 2/2004 |
| WO | WO 2004/029207 | 4/2004 |
| WO | WO 2004/035752 | 4/2004 |
| WO | WO 2004/099249 | 11/2004 |
| WO | WO 2005/000899 | 1/2005 |
| WO | WO 2005/040217 | 5/2005 |
| WO | WO 2005-047327 | 5/2005 |
| WO | WO-2005-063815 | 7/2005 |
| WO | WO-2005-070963 | 8/2005 |
| WO | WO 2005/092925 | 10/2005 |
| WO | WO 2006/053301 | 5/2006 |
| WO | WO 2006/076594 | 7/2006 |

OTHER PUBLICATIONS

Brekke et al., "Activation of complement by an IgG molecule without a genetic hinge." Nature (1993) 363:628-30.

Brekke et al., "The structural requirements for complement activation by IgG: does it hinge on the hinge?" Immunol. Today (1995) 16:85-90.

Bruggemann, M., et al. "Comparison of the Effector Functions of Human Immunoglobulins using a Matched Set of Chimeric Antibodies." J.Exp.Med. (1987) 166: 1351-61.

Clynes, R., et al. "Fc Receptors are Required in Passive and Active Immunity to Melanoma." Proc.Natl.Acad.Sci.U.S.A. (1998) 95: 652-6.

Coloma et al., "The Hinge as a Is Required for Spacer Contributes Function of IgG" J. Immunol. (1997)158:733-40.

Dall'Acqua, W. F., et al. "Increasing the Affinity of a Human IgG1 for the Neonatal Fc Receptor: Biological Consequences." J. Immunol. (2002) 169:5171-80.

Dall'Acqua, W. F., et al. "Modulation of the Effector Functions of a Human IgG1 through Engineering of its Hinge Region." J.Immunol. (2006) 177: 1129-38.

Dall'Acqua, W.F., et al. "Properties of human IgG1s engineered for enhanced binding to the neonatal Fc Receptor (fcRn)." JBC (2006) 281:23514-23524.

Dangl et al., "Segmental flexibility and complement fixation of genetically engineered chimeric human, rabbit and mouse antibodies."EMBO (1988) 71989-94.

Duncan, A. R., et al. "Localization of the Binding Site for the Human High-Affinity Fc Receptor on IgG." Nature (1988) 332: 563-4.

Ghetie, V., et al. "Increasing the Serum Persistence of an IgG Fragment by Random Mutagenesis." Nat.Biotechnol. (1997) 15: 637-40.

Gillies and Wesolowsi, "Antigen binding and biological activities of engineered mutant chimeric antibodies with human tumor speciicities." Hum. Antibod. Hybridomas (1990) 1: 47-54.

Hutchins, J. T., et al. "Improved Biodistribution, Tumor Targeting, and Reduced Immunogenicity in Mice with a Gamma 4 Variant of Campath-1H." Proc.Natl.Acad.Sci.U.S.A. (1995) 92: 11980-4.

Idusogie, E. E., et al. "Engineered Antibodies with Increased Activity to Recruit Complement." J.Immunol. (2001) 166: 2571-5.

Idusogie, E. E., et al. "Mapping of the C1q Binding Site on Rituxan, a Chimeric Antibody with a Human IgG1 Fc." J.Immunol. (2000) 164: 4178-84.

Jefferis, R., et al. "Interaction Sites on Human IgG-Fc for FcgammaR: Current Models." Immunol.Lett. (2002) 82: 57-65.

Jefferis, R., et al. "Modulation of Fc(Gamma)R and Human Complement Activation by IgG3-Core Oligosaccharide Interactions." Immunol.Lett. (1996) 54: 101-4.

Jefferis, R., et al. "Recognition Sites on Human IgG for Fc Gamma Receptors: The Role of Glycosylation." Immunol.Lett. (1995) 44: 111-7.

Kim, J-K, et al. "Mapping the site on human IgG for binding of the MHC class I-related receptor, FcRn" E. J of Immunol. (1999) 26:2819-2825.

Klein et al., "Expression of biological effector functions by immunoglobulin G molecules lacking the hinge region." Proc Natl Acad Sci USA (1981) 78: 524-8.

Lund, J., et al. "Multiple Interactions of IgG with its Core Oligosaccharide can Modulate Recognition by Complement and Human Fc Gamma Receptor I and Influence the Synthesis of its Oligosaccharide Chains." J.Immunol. (1996) 157: 4963-9.

Lund, J., et al. "Oligosaccharide-Protein Interactions in IgG can Modulate Recognition by Fc Gamma Receptors." FASEB J. (1995) 9: 115-9.

Lund, J., et al. "Multiple Binding Sites on the CH2 Domain of IgG for Mouse Fc Gamma R11." Mol.Immunol. (1992) 29: 53-9.

Lund, J., et al. "Human Fc Gamma RI and Fc Gamma RII Interact with Distinct but Overlapping Sites on Human IgG." J.Immunol. (1991) 147: 2657-62.

Oi, T., et al. "Correlation between segmental flexibility and effector function of antibodies." Nature (1984) 307: 136-40.

Patel, A. K., et al. "An Improved Assay for Antibody Dependent Cellular Cytotoxicity Based on Time Resolved Fluorometry." J.Immunol.Methods (1995) 184: 29-38.

Stefka, P.B., et al. "Enhanced half-life of genetically engineered human IgG1 antibodies in a humanized FcRn mouse model: potential application in humorally mediated autoimmune disease." Intern. Immunol. (2006) 18:1759-69.

Presta, L. G., et al. "Engineering Therapeutic Antibodies for Improved Function." Biochem.Soc.Trans. (2002) 30: 487-90.

Radaev, S., et al. "Recognition of immunoglobulins by Fcγ receptors." Mol. Immunol. (2001) 38:1073-83.

Reddy, M. P., et al. "Elimination of Fc Receptor-Dependent Effector Functions of a Modified IgG4 Monoclonal Antibody to Human CD4." J.Immunol. (2000) 164: 1925-33.

Redpath, S., et al. "Activation of complement by human IgG1 and IgG3 antibodies against the human leucocyte antigen CD52." Immunology (1998) 93:595-600.

Redpath, S., et al. "The Influence of the Hinge Region Length in Binding of Human IgG to Human Fcγ Receptors." Human Immunol. (1998) 59:720-27.

Shields, R. L., et al. "Lack of Fucose on Human IgG1 N-Linked Oligosaccharide Improves Binding to Human Fcgamma RIII and Antibody-Dependent Cellular Toxicity." J.Biol.Chem. (2002) 277: 26733-40.

Shopes, B., "A Genetically engineered human IgG with limited flexibility full initiates cytolysis via complement." Mol. Immunol. (1993) 30: 603-09.

Stevenson G., et al. "Conjugation of Human Fcγ in Closed-Hinge or Open Hinge Configuration to Fab' γ and Analogous Ligands." J. Immunol. (1997) 158:2242-50.

Tan, L., et al. "Influence of the hinge region on complement activation, C1q binding, and segmental flexibility in chimeric human immunoglobulins." Proc.Natl.Acad.Sci.U.S.A. (1990) 87:162-66.

Wilkinson, R. W., et al. "Antibody-Dependent Cell-Mediated Cytotoxicity: A Flow Cytometry-Based Assay using Fluorophores." J.Immunol.Methods (2001) 258: 183-91.

Wisecarver, J., et al. "A Method for Determination of Antibody-Dependent Cellular Cytotoxicity (ADCC) of Human Peripheral Mononuclear Cells." J.Immunol.Methods (1985) 79: 277-82.

Xu, D., et al. "In Vitro Characterization of Five Humanized OKT3 Effector Function Variant Antibodies." Cell.Immunol. (2000) 200: 16-26.

Chowdhury, Partha S. and Wu, Herren, 2005 Tailor-made antibody therapeutics, Methods, 36:11-24.

Dall'Acqua, William, et al., 1998, "Contribution of domain interface residues to the stability of antibody CH3 domain homodimers", Biochemistry, 37(26):9266-73.

Frew, Anthony J., 1998, "Effects of anti-IgE in asthmatic subjects", Thorax, 53, Supplement 2:S52-S57.

International Preliminary Report on Patentability and Written Opinion for corresponding to PCT/US06/25590 dated May 28, 2007.

International Search Report for corresponding to PCT/US06/25590 mailed Jun. 26, 2007.

Kim, Insook et al., 2002, "Lowering of pI by acylation improves the renal uptake of $^{99m}$Tc-labeled anti-Tac dsFv: effect of different acylating reagents", Nuclear Medicine and Biology, 29:795-801.

Onda, Masanori et al., 1999, "Reduction of the Nonspecific Animal Toxicity of Anti-Tac(Fv)-PE38 by Mutations in the Framework Regions of the Fv Which Lower the Isoelectric Point", The Journal of Immunology, 163:6072-6077.

Pardridge, William M. et al., 1998, "Enhanced Endocytosis in Cultured Human Breast Carcinoma Cells and In Vivo Biodistribution in Rats of a Humanized Monoclonal Antibody after Cationization of the Protein", The Journal of Pharmacology and Experimental Therapeutics, 286(1):548-554.

Renders, L. and Valerius, T., 2003, "Engineered CD3 antibodies for immunosuppression", Clin Exp Immunol., 133(3):307-9.

Shields, R.L., et al., 2001, High resolution mapping of the binding site on human IgG1 for Fc gamma RI, Fc gamma RII, Fc gamma RIII, and FcRn and design of IgG1 variants with improved binding to the Fc gamma R., J Biol Chem. 2;276(9):6591-604.

Supplementary European Search Report for corresponding EP Application No. 06785972 dated Dec. 8, 2009.

Triguero, Dominigo et al., 1989, "Blood-brain barrier transport of cationized immunoglobulin G: Enhanced delivery compared to native protein", Proc. Natl. Acad. Sci. USA, 86:4761-4765.

Ueda, Hiroshi et al., 2004, "Stablization of antibody $V_H$—domains by proteolytic selection", Journal of Molecular Catalysis B: Enzymatic 28:173-179.

Vermeer, Arnoldus W.P. et al., 2000, "The Unfolding/Denaturation of Immunogammaglobulin of Isotype 2b and its $F_{ab}$ and $F_c$ Fragments", Biophysical Journal, 79:2150-2154.

* cited by examiner

SEQUENCE LISTING

<160> NUMBER OF SEQ ID NOS: 64

<210> SEQ ID NO 1
<211> LENGTH: 34
<212> TYPE: DNA

```
<213> ORGANISM: Artificial
<220> FEATURE:
<223> OTHER INFORMATION: synthetic primer

<400> SEQUENCE: 1
ccatctccaa agcccagggg cagccccgag aacc                           34

<210> SEQ ID NO 2
<211> LENGTH: 34
<212> TYPE: DNA
<213> ORGANISM: Artificial
<220> FEATURE:
<223> OTHER INFORMATION: synthetic primer

<400> SEQUENCE: 2
ggttctcggg gctgcccctg ggctttggag atgg                           34

<210> SEQ ID NO 3
<211> LENGTH: 34
<212> TYPE: DNA
<213> ORGANISM: Artificial
<220> FEATURE:
<223> OTHER INFORMATION: synthetic primer

<400> SEQUENCE: 3
ccatctccaa agccgagggg cagccccgag aacc                           34

<210> SEQ ID NO 4
<211> LENGTH: 34
<212> TYPE: DNA
<213> ORGANISM: Artificial
<220> FEATURE:
<223> OTHER INFORMATION: synthetic primer

<400> SEQUENCE: 4
ggttctcggg gctgcccctc ggctttggag atgg                           34

<210> SEQ ID NO 5
<211> LENGTH: 37
<212> TYPE: DNA
<213> ORGANISM: Artificial
<220> FEATURE:
<223> OTHER INFORMATION: synthetic primer

<400> SEQUENCE: 5
gccaaagggc agccccgaca gccacaggtg tacaccc                        37

<210> SEQ ID NO 6
<211> LENGTH: 37
<212> TYPE: DNA
<213> ORGANISM: Artificial
<220> FEATURE:
<223> OTHER INFORMATION: synthetic primer

<400> SEQUENCE: 6
gggtgtacac ctgtggctgt cggggctgcc ctttggc                        37

<210> SEQ ID NO 7
<211> LENGTH: 37
<212> TYPE: DNA
<213> ORGANISM: Artificial
<220> FEATURE:
<223> OTHER INFORMATION: synthetic primer

<400> SEQUENCE: 7
gccaaagggc agccccgaaa gccacaggtg tacaccc                        37
```

<210> SEQ ID NO 8
<211> LENGTH: 37
<212> TYPE: DNA
<213> ORGANISM: Artificial
<220> FEATURE:
<223> OTHER INFORMATION: synthetic primer

<400> SEQUENCE: 8
gggtgtacac ctgtggcttt cggggctgcc ctttggc       37

<210> SEQ ID NO 9
<211> LENGTH: 36
<212> TYPE: DNA
<213> ORGANISM: Artificial
<220> FEATURE:
<223> OTHER INFORMATION: synthetic primer

<400> SEQUENCE: 9
ccctgccccc atcccaggag gagatgacca agaacc       36

<210> SEQ ID NO 10
<211> LENGTH: 36
<212> TYPE: DNA
<213> ORGANISM: Artificial
<220> FEATURE:
<223> OTHER INFORMATION: synthetic primer

<400> SEQUENCE: 10
ggttcttggt catctcctcc tgggatgggg gcaggg       36

<210> SEQ ID NO 11
<211> LENGTH: 36
<212> TYPE: DNA
<213> ORGANISM: Artificial
<220> FEATURE:
<223> OTHER INFORMATION: synthetic primer

<400> SEQUENCE: 11
ccctgccccc atccgaggag gagatgacca agaacc       36

<210> SEQ ID NO 12
<211> LENGTH: 36
<212> TYPE: DNA
<213> ORGANISM: Artificial
<220> FEATURE:
<223> OTHER INFORMATION: synthetic primer

<400> SEQUENCE: 12
ggttcttggt catctcctcc tcggatgggg gcaggg       36

<210> SEQ ID NO 13
<211> LENGTH: 35
<212> TYPE: DNA
<213> ORGANISM: Artificial
<220> FEATURE:
<223> OTHER INFORMATION: synthetic primer

<400> SEQUENCE: 13
ggagatgacc aagaacgagg tcagcctgac ctgcc       35

<210> SEQ ID NO 14
<211> LENGTH: 38
<212> TYPE: DNA
<213> ORGANISM: Artificial
<220> FEATURE:
<223> OTHER INFORMATION: synthetic primer

```
<400> SEQUENCE: 14
ccaggcaggt caggctgacc tcgttcttgg tcatctcc                                   38

<210> SEQ ID NO 15
<211> LENGTH: 35
<212> TYPE: DNA
<213> ORGANISM: Artificial
<220> FEATURE:
<223> OTHER INFORMATION: synthetic primer

<400> SEQUENCE: 15
ggagatgacc aagaacaagg tcagcctgac ctgcc                                      35

<210> SEQ ID NO 16
<211> LENGTH: 38
<212> TYPE: DNA
<213> ORGANISM: Artificial
<220> FEATURE:
<223> OTHER INFORMATION: synthetic primer

<400> SEQUENCE: 16
ccaggcaggt caggctgacc ttgttcttgg tcatctcc                                   38

<210> SEQ ID NO 17
<211> LENGTH: 36
<212> TYPE: DNA
<213> ORGANISM: Artificial
<220> FEATURE:
<223> OTHER INFORMATION: synthetic primer

<400> SEQUENCE: 17
cgcctcccgt gctggactcc aacggctcct tcttcc                                     36

<210> SEQ ID NO 18
<211> LENGTH: 36
<212> TYPE: DNA
<213> ORGANISM: Artificial
<220> FEATURE:
<223> OTHER INFORMATION: synthetic primer

<400> SEQUENCE: 18
ggaagaagga gccgttggag tccagcacgg gaggcg                                     36

<210> SEQ ID NO 19
<211> LENGTH: 36
<212> TYPE: DNA
<213> ORGANISM: Artificial
<220> FEATURE:
<223> OTHER INFORMATION: synthetic primer

<400> SEQUENCE: 19
cgcctcccgt gctggactcc aagggctcct tcttcc                                     36

<210> SEQ ID NO 20
<211> LENGTH: 36
<212> TYPE: DNA
<213> ORGANISM: Artificial
<220> FEATURE:
<223> OTHER INFORMATION: synthetic primer

<400> SEQUENCE: 20
ggaagaagga gcccttggag tccagcacgg gaggcg                                     36

<210> SEQ ID NO 21
<211> LENGTH: 40
<212> TYPE: DNA
```

<213> ORGANISM: Artificial
<220> FEATURE:
<223> OTHER INFORMATION: synthetic primer

<400> SEQUENCE: 21
gaccaagaac caggtcagcg agacctgcct ggtcaaaggc                40

<210> SEQ ID NO 22
<211> LENGTH: 40
<212> TYPE: DNA
<213> ORGANISM: Artificial
<220> FEATURE:
<223> OTHER INFORMATION: synthetic primer

<400> SEQUENCE: 22
gcctttgacc aggcaggtct cgctgacctg gttcttggtc                40

<210> SEQ ID NO 23
<211> LENGTH: 40
<212> TYPE: DNA
<213> ORGANISM: Artificial
<220> FEATURE:
<223> OTHER INFORMATION: synthetic primer

<400> SEQUENCE: 23
gaccaagaac caggtcagca agacctgcct ggtcaaaggc                40

<210> SEQ ID NO 24
<211> LENGTH: 40
<212> TYPE: DNA
<213> ORGANISM: Artificial
<220> FEATURE:
<223> OTHER INFORMATION: synthetic primer

<400> SEQUENCE: 24
gcctttgacc aggcaggtct tgctgacctg gttcttggtc                40

<210> SEQ ID NO 25
<211> LENGTH: 41
<212> TYPE: DNA
<213> ORGANISM: Artificial
<220> FEATURE:
<223> OTHER INFORMATION: synthetic primer

<400> SEQUENCE: 25
gctccttctt cctctatagc cagctcaccg tggacaagag c                41

<210> SEQ ID NO 26
<211> LENGTH: 41
<212> TYPE: DNA
<213> ORGANISM: Artificial
<220> FEATURE:
<223> OTHER INFORMATION: synthetic primer

<400> SEQUENCE: 26
gctcttgtcc acggtgagct ggctatagag gaagaaggag c                41

<210> SEQ ID NO 27
<211> LENGTH: 41
<212> TYPE: DNA
<213> ORGANISM: Artificial
<220> FEATURE:
<223> OTHER INFORMATION: synthetic primer

<400> SEQUENCE: 27
gctccttctt cctctatagc gagctcaccg tggacaagag c                41

```
<210> SEQ ID NO 28
<211> LENGTH: 41
<212> TYPE: DNA
<213> ORGANISM: Artificial
<220> FEATURE:
<223> OTHER INFORMATION: synthetic primer

<400> SEQUENCE: 28
gctcttgtcc acggtgagct cgctatagag gaagaaggag c                    41

<210> SEQ ID NO 29
<211> LENGTH: 41
<212> TYPE: DNA
<213> ORGANISM: Artificial
<220> FEATURE:
<223> OTHER INFORMATION: synthetic primer

<400> SEQUENCE: 29
ccatctccaa agccaaaggg gagccccgag aaccacaggt g                    41

<210> SEQ ID NO 30
<211> LENGTH: 41
<212> TYPE: DNA
<213> ORGANISM: Artificial
<220> FEATURE:
<223> OTHER INFORMATION: synthetic primer

<400> SEQUENCE: 30
cacctgtggt tctcggggct cccctttggc tttggagatg g                    41

<210> SEQ ID NO 31
<211> LENGTH: 41
<212> TYPE: DNA
<213> ORGANISM: Artificial
<220> FEATURE:
<223> OTHER INFORMATION: synthetic primer

<400> SEQUENCE: 31
ccatctccaa agccaaaggg aagccccgag aaccacaggt g                    41

<210> SEQ ID NO 32
<211> LENGTH: 41
<212> TYPE: DNA
<213> ORGANISM: Artificial
<220> FEATURE:
<223> OTHER INFORMATION: synthetic primer

<400> SEQUENCE: 32
cacctgtggt tctcggggct tccctttggc tttggagatg g                    41

<210> SEQ ID NO 33
<211> LENGTH: 44
<212> TYPE: DNA
<213> ORGANISM: Artificial
<220> FEATURE:
<223> OTHER INFORMATION: synthetic primer

<400> SEQUENCE: 33
ctccaaagcc aaagggcagc cccaggaacc acaggtgtac accc                 44

<210> SEQ ID NO 34
<211> LENGTH: 44
<212> TYPE: DNA
<213> ORGANISM: Artificial
<220> FEATURE:
<223> OTHER INFORMATION: synthetic primer
```

```
<400> SEQUENCE: 34
gggtgtacac ctgtggttcc tggggctgcc ctttggcttt ggag            44

<210> SEQ ID NO 35
<211> LENGTH: 44
<212> TYPE: DNA
<213> ORGANISM: Artificial
<220> FEATURE:
<223> OTHER INFORMATION: synthetic primer

<400> SEQUENCE: 35
ctccaaagcc aaagggcagc ccgaggaacc acaggtgtac accc            44

<210> SEQ ID NO 36
<211> LENGTH: 44
<212> TYPE: DNA
<213> ORGANISM: Artificial
<220> FEATURE:
<223> OTHER INFORMATION: synthetic primer

<400> SEQUENCE: 36
gggtgtacac ctgtggttcc tcgggctgcc ctttggcttt ggag            44

<210> SEQ ID NO 37
<211> LENGTH: 39
<212> TYPE: DNA
<213> ORGANISM: Artificial
<220> FEATURE:
<223> OTHER INFORMATION: synthetic primer

<400> SEQUENCE: 37
ccctgccccc atcccggcag gagatgacca agaaccagg                  39

<210> SEQ ID NO 38
<211> LENGTH: 39
<212> TYPE: DNA
<213> ORGANISM: Artificial
<220> FEATURE:
<223> OTHER INFORMATION: synthetic primer

<400> SEQUENCE: 38
cctggttctt ggtcatctcc tgccgggatg ggggcaggg                  39

<210> SEQ ID NO 39
<211> LENGTH: 39
<212> TYPE: DNA
<213> ORGANISM: Artificial
<220> FEATURE:
<223> OTHER INFORMATION: synthetic primer

<400> SEQUENCE: 39
ccctgccccc atcccggaag gagatgacca agaaccagg                  39

<210> SEQ ID NO 40
<211> LENGTH: 39
<212> TYPE: DNA
<213> ORGANISM: Artificial
<220> FEATURE:
<223> OTHER INFORMATION: synthetic primer

<400> SEQUENCE: 40
cctggttctt ggtcatctcc ttccgggatg ggggcaggg                  39

<210> SEQ ID NO 41
<211> LENGTH: 44
<212> TYPE: DNA
```

```
<213> ORGANISM: Artificial
<220> FEATURE:
<223> OTHER INFORMATION: synthetic primer

<400> SEQUENCE: 41
caagaccacg cctcccgtgg aggactccga cggctccttc ttcc            44

<210> SEQ ID NO 42
<211> LENGTH: 44
<212> TYPE: DNA
<213> ORGANISM: Artificial
<220> FEATURE:
<223> OTHER INFORMATION: synthetic primer

<400> SEQUENCE: 42
ggaagaagga gccgtcggag tcctccacgg gaggcgtggt cttg            44

<210> SEQ ID NO 43
<211> LENGTH: 44
<212> TYPE: DNA
<213> ORGANISM: Artificial
<220> FEATURE:
<223> OTHER INFORMATION: synthetic primer

<400> SEQUENCE: 43
caagaccacg cctcccgtga aggactccga cggctccttc ttcc            44

<210> SEQ ID NO 44
<211> LENGTH: 44
<212> TYPE: DNA
<213> ORGANISM: Artificial
<220> FEATURE:
<223> OTHER INFORMATION: synthetic primer

<400> SEQUENCE: 44
ggaagaagga gccgtcggag tccttcacgg gaggcgtggt cttg            44

<210> SEQ ID NO 45
<211> LENGTH: 39
<212> TYPE: DNA
<213> ORGANISM: Artificial
<220> FEATURE:
<223> OTHER INFORMATION: synthetic primer

<400> SEQUENCE: 45
ccatctccaa agccaaagac cagccccgag aaccacagg                  39

<210> SEQ ID NO 46
<211> LENGTH: 39
<212> TYPE: DNA
<213> ORGANISM: Artificial
<220> FEATURE:
<223> OTHER INFORMATION: synthetic primer

<400> SEQUENCE: 46
cctgtggttc tcggggctgg tctttggctt tggagatgg                  39

<210> SEQ ID NO 47
<211> LENGTH: 39
<212> TYPE: DNA
<213> ORGANISM: Artificial
<220> FEATURE:
<223> OTHER INFORMATION: synthetic primer

<400> SEQUENCE: 47
ccatctccaa agccaaaaag cagccccgag aaccacagg                  39
```

<210> SEQ ID NO 48
<211> LENGTH: 39
<212> TYPE: DNA
<213> ORGANISM: Artificial
<220> FEATURE:
<223> OTHER INFORMATION: synthetic primer

<400> SEQUENCE: 48
cctgtggttc tcggggctgc tttttggctt tggagatgg                                39

<210> SEQ ID NO 49
<211> LENGTH: 40
<212> TYPE: DNA
<213> ORGANISM: Artificial
<220> FEATURE:
<223> OTHER INFORMATION: synthetic primer

<400> SEQUENCE: 49
cccccatccc gggaggagga aaccaagaac caggtcagcc                               40

<210> SEQ ID NO 50
<211> LENGTH: 40
<212> TYPE: DNA
<213> ORGANISM: Artificial
<220> FEATURE:
<223> OTHER INFORMATION: synthetic primer

<400> SEQUENCE: 50
ggctgacctg gttcttggtt tcctcctccc gggatggggg                               40

<210> SEQ ID NO 51
<211> LENGTH: 40
<212> TYPE: DNA
<213> ORGANISM: Artificial
<220> FEATURE:
<223> OTHER INFORMATION: synthetic primer

<400> SEQUENCE: 51
cccccatccc gggaggagaa gaccaagaac caggtcagcc                               40

<210> SEQ ID NO 52
<211> LENGTH: 40
<212> TYPE: DNA
<213> ORGANISM: Artificial
<220> FEATURE:
<223> OTHER INFORMATION: synthetic primer

<400> SEQUENCE: 52
ggctgacctg gttcttggtc ttctcctccc gggatggggg                               40

<210> SEQ ID NO 53
<211> LENGTH: 37
<212> TYPE: DNA
<213> ORGANISM: Artificial
<220> FEATURE:
<223> OTHER INFORMATION: synthetic primer

<400> SEQUENCE: 53
ccatcccggg aggagatgga gaagaaccag gtcagcc                                  37

<210> SEQ ID NO 54
<211> LENGTH: 37
<212> TYPE: DNA
<213> ORGANISM: Artificial
<220> FEATURE:
<223> OTHER INFORMATION: synthetic primer -continued

<400> SEQUENCE: 54
ggctgacctg gttcttctcc atctcctccc gggatgg             37

<210> SEQ ID NO 55
<211> LENGTH: 37
<212> TYPE: DNA
<213> ORGANISM: Artificial
<220> FEATURE:
<223> OTHER INFORMATION: synthetic primer

<400> SEQUENCE: 55
ccatcccggg aggagatgaa gaagaaccag gtcagcc             37

<210> SEQ ID NO 56
<211> LENGTH: 37
<212> TYPE: DNA
<213> ORGANISM: Artificial
<220> FEATURE:
<223> OTHER INFORMATION: synthetic primer

<400> SEQUENCE: 56
ggctgacctg gttcttcttc atctcctccc gggatgg             37

<210> SEQ ID NO 57
<211> LENGTH: 41
<212> TYPE: DNA
<213> ORGANISM: Artificial
<220> FEATURE:
<223> OTHER INFORMATION: synthetic primer

<400> SEQUENCE: 57
cccgggagga gatgaccaag gaccaggtca gcctgacctg c             41

<210> SEQ ID NO 58
<211> LENGTH: 41
<212> TYPE: DNA
<213> ORGANISM: Artificial
<220> FEATURE:
<223> OTHER INFORMATION: synthetic primer

<400> SEQUENCE: 58
gcaggtcagg ctgacctggt ccttggtcat ctcctcccgg g             41

<210> SEQ ID NO 59
<211> LENGTH: 41
<212> TYPE: DNA
<213> ORGANISM: Artificial
<220> FEATURE:
<223> OTHER INFORMATION: synthetic primer

<400> SEQUENCE: 59
cccgggagga gatgaccaag aagcaggtca gcctgacctg c             41

<210> SEQ ID NO 60
<211> LENGTH: 41
<212> TYPE: DNA
<213> ORGANISM: Artificial
<220> FEATURE:
<223> OTHER INFORMATION: synthetic primer

<400> SEQUENCE: 60
gcaggtcagg ctgacctgct tcttggtcat ctcctcccgg g             41

<210> SEQ ID NO 61
<211> LENGTH: 42
<212> TYPE: DNA

-continued

```
<213> ORGANISM: Artificial
<220> FEATURE:
<223> OTHER INFORMATION: synthetic primer

<400> SEQUENCE: 61
gcaatgggca gccggagaac gactacaaga ccacgcctcc cg            42

<210> SEQ ID NO 62
<211> LENGTH: 42
<212> TYPE: DNA
<213> ORGANISM: Artificial
<220> FEATURE:
<223> OTHER INFORMATION: synthetic primer

<400> SEQUENCE: 62
cgggaggcgt ggtcttgtag tcgttctccg gctgcccatt gc            42

<210> SEQ ID NO 63
<211> LENGTH: 42
<212> TYPE: DNA
<213> ORGANISM: Artificial
<220> FEATURE:
<223> OTHER INFORMATION: synthetic primer

<400> SEQUENCE: 63
gcaatgggca gccggagaac aagtacaaga ccacgcctcc cg            42

<210> SEQ ID NO 64
<211> LENGTH: 42
<212> TYPE: DNA
<213> ORGANISM: Artificial
<220> FEATURE:
<223> OTHER INFORMATION: synthetic primer

<400> SEQUENCE: 64
cgggaggcgt ggtcttgtac ttgttctccg gctgcccatt gc            42
```

INTEGRATED APPROACH FOR GENERATING MULTIDOMAIN PROTEIN THERAPEUTICS

CROSS REFERENCE TO RELATED APPLICATIONS

This application is a national phase filing of Application No. PCT/US2006/025590, which was filed with the Patent Corporation Treaty on Jun. 30, 2006, and claims the benefit under 35 U.S.C. §119(e) of U.S. provisional Patent Application Nos. 60/696,113 filed Jul. 1, 2005 and 60/788,692 filed Apr. 4, 2006, which are hereby incorporated by reference herein in their entirety for all purposes.

1. FIELD OF THE INVENTION

The invention relates to a method for therapeutic protein development that allows generation of proteins of both high therapeutic efficacy and optimal formulation characteristics, e.g., high solubility and long shelf life. The present invention also relates to a method for evaluating one or more metrics, which provide an indication of the shelf life of a multidomain protein formulation.

2. BACKGROUND OF THE INVENTION

A wide variety of biologically active proteins and polypeptides can now be produced in sufficiently large quantities for use as drugs. For example, the development of the hybridoma method and recombinant DNA techniques have made it possible to produce antibodies on large scale. This has allowed wide use of pharmaceutical compositions containing proteins, such as antibodies, for treating a variety of diseases. Such treatments normally require administering to a patient the proteins at high concentrations.

However, a protein that has desired therapeutic properties may not have sufficiently high solubility. Even for those proteins that have high solubility, high concentration liquid formulations tend to have short shelf lives and may lose biological activity as a result of chemical and physical instabilities during the storage. Additionally, proteins are generally more viscous at high concentrations, which can complicate packaging, storage and delivery of the protein therapeutic. Furthermore, chemical instability may be caused by deamidation, racemization, hydrolysis, oxidation, beta elimination or disulfide exchange, and physical instability may be caused by protein denaturation, aggregation, precipitation or adsorption. Among those, aggregation, deamidation and oxidation are known to be the most common causes of antibody degradation (Wang et al., 1988, *J. of Parenteral Science & Technology* 42 (Suppl.):S4-S26; Cleland et al., 1993, *Critical Reviews in Therapeutic Drug Carrier Systems* 10(4):307-377; Manning et al., 1989, Pharm. Res. 6:903-918). Aggregate formation during storage of a liquid protein composition can adversely affect the biological activity of the protein, resulting in loss of therapeutic efficacy and/or an increase in immunogenicity in humans. Aggregate formation may also cause other problems such as blockage of tubing, membranes, or pumps when the protein composition is administered using an infusion system.

Due to the instability of proteins in liquid pharmaceutical formulations, protein therapeutics are often packaged in the lyophilized form along with a suitable liquid medium for reconstitution. Although lyophilization improves storage stability of the composition, many proteins exhibit decreased activity, either due to storage in the dried state (Pikal, 1990, Biopharm. 27:26-30) or as a result of aggregate formation or loss of catalytic activity upon reconstitution as a liquid formulation (see, for example, Carpenter et al., 1991, Develop. Biol. Standard 74:225-239; Broadhead et al., 1992, Drug Devel. Ind. Pharm. 18:1169-1206; Mumenthaler et al., 1994, Pharm. Res. 11:12-20; Carpenter et al., 1988, Cryobiology 25:459-470; and Roser, 1991, Biopharm. 4:47-53). Lyophilized formulations of antibodies also require a prolonged process for lyophilization and high cost for manufacturing. A lyophilized formulation has to be reconstituted aseptically and accurately by healthcare practitioners prior to administering to patients. The reconstitution procedure is cumbersome and the time limitation after the reconstitution can cause great inconveniences in administering the formulation to patients, leading to significant waste, if not reconstituted properly or if the reconstituted dose is not used within six (6) hours and must be discarded. Reconstitution may also increase the possibility of incorrect dosing. Thus, a lyophilized formulation which is more stable and is readily reconstituted with little loss in potency is desirable.

A desirable alternative to lyophilized formulations is liquid formulations of protein therapeutics having concentrations comparable to or higher than the reconstituted lyophilized formulations. Such liquid formulations of protein therapeutics can be administered to a subject without the need of reconstitution, thereby allowing healthcare practitioners much quicker and easier administration of protein therapeutics to a patient. In addition, the manufacturing process of the liquid formulation protein therapeutics is simpler and more efficient than the manufacturing process for the lyophilized version because all stages of the manufacturing of the liquid formulations are carried out in an aqueous solution, involving no drying process, such as lyophilization. Accordingly, it is also more cost effective. The development of high concentration, ready-to-use, liquid formulations of protein therapeutics has thus attracted great attention in the biopharmaceutical industry.

Stability of proteins and polypeptides in pharmaceutical formulations, both liquid and lyophilized, can be affected, for example, by factors such as pH, ionic strength, temperature, repeated cycles of freeze-thaw, and exposure to mechanical shear forces such as occur during processing. Various highly stable, high concentration liquid formulations have been successfully developed. For example, liquid formulations of antibodies that are stable for more than 5 years when stored at 4° C. have been reported. U.S. Pat. No. 6,525,102 discloses a stabilized liquid polypeptide-containing pharmaceutical composition. The composition comprises an amino acid base, which serves as the primary stabilizing agent of the polypeptide, and an acid and/or its salt form to buffer the solution within an acceptable pH range for stability of the polypeptide. The compositions are near isotonic. The '102 patent also discloses methods for increasing stability of a polypeptide in a liquid pharmaceutical composition and for increasing storage stability of such a pharmaceutical composition. Lyophilized formulations are common and their stability and reconstitution characteristics may be modified by the addition of stabilizers and/or excipients. However, the development of such liquid and lyophilized formulations depends on the particular protein therapeutics, and often requires significant optimization efforts. Thus, improving the stability of pharmaceutical compositions containing protein therapeutics of a pharmaceutically effective concentration remains a challenge. An additional challenge is providing for formulations which have low enough viscosity to be readily manufactured and/or administered at high concentrations.

In a traditional approach to therapeutic protein (e.g., antibody) development, the protein that has a desired activity and/or property (e.g., binding affinity) is first generated. The protein is then submitted for formulation development to determine the optimal formulation and storage conditions. Traditional screening and optimization processes require lengthy stability studies which are both time consuming and can only examine a limited number of potential formulations. If the protein should fail to meet the formulation requirements, the whole drug development process essentially fails. Thus, there is a need for methods that allow incorporating formulation considerations into early stages of the drug development process. In addition, since the desired shelf life can be as long as one year or longer, methods relying monitoring the formulations in real time are inefficient. Attempts have been made to develop methods for rapidly screening formulations. For example, U.S. Pat. No. 6,232,085 discloses a multi-variable method for optimizing the shelf life of a protein which is capable of denaturing due to a thermal change. The method comprises contacting the target molecule with one or more of a multiplicity of different molecules or different biochemical conditions in each of a multiplicity of containers, simultaneously heating the multiplicity of containers, measuring in each of the containers a physical change associated with the thermal denaturation of the target molecule resulting from heating, generating a thermal denaturation curve for the target molecule as a function of temperature for each of the containers, comparing each of the denaturation curves to (i) each of the other thermal denaturation curves and to (ii) the thermal denaturation curve obtained for the target under a reference set of biochemical conditions, and ranking the efficacies of multiplicity of different molecules or the different biochemical conditions according to the change in each of the thermal denaturation curves. However, such methods are cumbersome and do not address the address the intrinsic properties or characteristics, such as, pI and Tm, of the protein to be formulated.

The intrinsic properties of proteins not only affect their formulation characteristics but may have serious implications for their therapeutic use as well. For example, studies have shown that recombinant toxins made up of a cell-targeting Fv portion of an antibody fused to a toxin have non-specific dose limiting toxicities (e.g., non-specific liver toxicities) which are attributable to the high isoelectric point (pI) of the Fv portion of the molecule. Lowering the pI of the Fv portion of these recombinant toxins by site directed mutagenesis reduced their non-specific toxicity in animal models without altering reducing their antitumor activity (Onda et al., 1999, J. Immunol., 163: 6072-77, Onda et al., 2001, Cancer Res., 61: 5070-77). Likewise, lowering the pI of a radiolabelled antitumor dsFv (disulfide stabilized Fv) by chemical modification increased renal clearance thereby decreasing the buildup of radioactivity in the kidney (Kim et al., 2002, Nucl. Med. Biol., 29: 795-801).

In other studies the transendothelial migration and endocytosis of antibodies was enhanced by cationization to increase the pI. The cationized antibodies retained their binding affinity and were rapidly internalized into cells with minimal non-specific toxicity or immunogenicity (Pardrige et al., 1998, J. Pharmaol. Exp. Therap., 286: 548-54). Cationization of antibodies has also been shown to enhance the delivery of antibodies across the blood brain barrier (Triguero et al., 1989, PNAS, 86: 4761-4765) These data indicate that there may be an optimal pI for certain therapeutic proteins, such as antibodies or chimeric proteins made up of antibody domains. Particularly those proteins which carry a toxin, are required in large doses for optimal therapeutic response or those which are required intracellularly or in extravascular compartments.

Thus, there is a need for more efficient methods that allow quick indication of the shelf life and/or clinical properties of protein formulations based on the intrinsic properties of the protein. Additionally, because certain intrinsic properties, such as pI and Tm, are generally not selection criterion when therapeutic proteins (e.g., antibodies) are developed, proteins which are therapeutically active may have suboptimal formulation or clinical properties. Methods to engineer certain intrinsic properties, such as pI and Tm, downstream of, or concurrently with development would allow the rapid production of proteins with preferred formulation and therapeutic characteristics.

Discussion or citation of a reference herein shall not be construed as an admission that such reference is prior art to the present invention.

3. SUMMARY OF THE INVENTION

The invention is based in part on the discovery of the inventors that certain therapeutic and/or formulation and/or manufacturing characteristics of a multidomain protein can be evaluated by examining individual domains that form the protein. One or more metrics representing the physical and/or chemical and/or structural characteristics of protein domains are determined and individual domains are then selected based on their metrics. The individual domains may be examined in the context of the intact multidomain protein or as isolated domains. For example, the physical/chemical (including structural) characteristics of a Fab or an Fc domain in an antibody may determine the biodistribution and/or non-specific toxicity and/or stability and/or solubility and/or viscosity of the antibody. An approach incorporating selecting appropriate domains having optimal therapeutic and/or formulation characteristics prior to or concurrently with the generation of the full protein improves the overall drug development efficiency. This approach thus allows generation of proteins of both high therapeutic efficacy and optimal formulation characteristics, e.g., high solubility and long shelf life.

The invention provides an integrated approach to therapeutic protein development which incorporates therapeutic and/or formulation and/or manufacturing considerations in the early screening and development process. The approach involves evaluating one or more individual domains of a protein to identify domains that have both the desired biological activity and desired therapeutic and/or formulation characteristics. For example, a plurality of different variants of a domain that have been determined to have the desired biological activity can be screened to identify one or more variants that have certain desired therapeutic and/or formulation characteristics, e.g., having desired stability and/or solubility. The identified domain variants are then used in the construction of the full multidomain proteins. For example, in therapeutic antibody development, after affinity screening of an expression library (e.g., a phage display library), Fab domains having high binding affinity can be screened for their formulation characteristics, e.g., solubility and/or stability. One or more Fab domains having desired formulation characteristics, e.g., having high solubility and/or stability, are selected and each used with an appropriate Fc domain in the construction of the full antibodies. Different candidate (including variant/modified domains) Fc domains can also be screened for formulation characteristics, e.g., solubility and stability, to select an Fc domain that has the desired formulation characteristics. The constructed antibodies are then submitted for further formulation development.

The invention further provides methods for the development of a therapeutic multidomain protein by engineering one or more domains of the multidomain protein to have the desired therapeutic and/or formulation characteristics such as for example, biodistribution, non-specific toxicity, solubility and/or stability. For example, a domain having a desired biological activity can be modified by replacing one or more amino acid residues in said domain to generated a modified domain or a population of modified domains which are then screened for their therapeutic characteristics, e.g., biodistribution and/or non-specific toxicity. One or more modified domains having desired therapeutic characteristics are selected and each used in the construction of the full multidomain protein.

The present invention also provides a method for evaluating the shelf life, i.e., the long term stability, of a protein preparation comprising a multidomain protein based on a thermal denaturation and/or renaturation behavior of a multidomain protein in a liquid protein preparation. It is contemplated that the multidomain protein may comprise a domain whose unfolding leads to aggregation of the multidomain protein in the liquid protein preparation. The liquid protein preparation can be a solution of the multidomain protein of a particular concentration, e.g., a concentration from about 5 to 300 mg/ml. The liquid preparation can also comprise other substances, including but not limited to, salts, ligands, co-factors, and so on. The method thus can also be used for determining the optimal conditions, e.g., the constituents and the optimal concentration of each such constituent.

The invention provides a method of generating one or more multidomain proteins, comprising (a) evaluating for each of a plurality of candidate domains one or more metrics representing one or more therapeutic and/or formulation and/or manufacturing characteristics of the domain, wherein the plurality of candidate domains exhibits a biological activity above a predetermined threshold level; (b) selecting one or more domains from the plurality based on the metrics; and (c) optionally, constructing a full multidomain protein using each domain selected in step (b) and one or more other domains. In one embodiment, the method of the invention is used to generate one or more antibodies. In a specific embodiment, the domain is an antigen binding domain (e.g., Fab domain). In one embodiment, the metrics of the invention include one or more parameters characterizing the stability of a candidate domain. In another embodiment, the metrics of the invention include one or more parameters characterizing the solubility, biodistribution or non-specific toxicity of a candidate domain. In a specific embodiment, the parameters characterizing stability of a candidate domain include the Tm value of the domain, and the parameters characterizing solubility, biodistribution or non-specific toxicity of a candidate domain include the pI value of the domain. The metrics of the invention may further include metrics characterizing stability of a candidate domain under one or more different conditions selected from the group consisting of different pH values, different temperatures, different shear stresses, and different freeze/thaw cycles.

The plurality of candidate domains can be an antigen binding domains (e.g., Fab domains). In such cases, the biological activity may be the antigen binding domain's binding affinity to a target antigen. In certain embodiments, at least some of the antigen binding domains bind different epitopes of the antigen. In a specific embodiment, the plurality of antigen binding domains are obtained by screening an expression library (e.g., a phage display library) with the antigen. In another specific embodiment, the plurality of antigen binding domains are obtained by digesting a plurality of monoclonal antibodies. Each selected antigen binding is then combined with one or more other domains (e.g., constant region domains) to generate one or more multidomain proteins.

The plurality of candidate domains can be constant region domains. In such cases, the biological activity may be the constant region domain's binding affinity to constant region domain receptors and/or ligands (e.g., FcRn, C1q, FcγRs) and/or ability to mediate effector functions (e.g., ADCC, CDC). In a specific embodiment, the plurality of constant region domains are obtained by screening an expression library with a constant region domain ligand. Each selected constant region domain is then combined with another domain (e.g., a antigen binding domain, a cellular receptor domain) to generate one or more multidomain proteins.

In one embodiment, metrics of the invention include one or more parameters characterizing stability of an antigen binding domain (e.g., Fab domain). In another embodiment, metrics include one or more parameters characterizing solubility, biodistribution or non-specific toxicity of an antigen binding domain. In a specific embodiment, the parameters characterizing stability of an antigen binding domain include a Tm value of the antigen binding domain, and the parameters characterizing solubility, biodistribution or non-specific toxicity of an antigen binding domain comprise a pI value of the antigen binding domain. The metrics of the invention may further include metrics characterizing stability of the antigen binding domain under one or more different conditions selected from the group consisting of different pH values, different temperatures, different shear stresses, and different freeze/thaw cycles.

In one embodiment, metrics of the invention include one or more parameters characterizing stability of a constant region domain (e.g., Fc domain). In another embodiment, metrics include one or more parameters characterizing solubility, biodistribution or non-specific toxicity of a constant region domain. In a specific embodiment, said the parameters characterizing stability of said constant region domain include a Tm value of the constant region domain, and the parameters characterizing solubility, biodistribution or non-specific toxicity of the constant region domain include a pI value of the constant region domain. The metrics of the invention may further include metrics characterizing stability of the constant region domain under one or more different conditions selected from the group consisting of different pH values, different temperatures, different shear stresses, and different freeze/thaw cycles.

In one embodiment, the method of generating one or more multidomain proteins further comprises, before using the selected domain to construct a full multidomain protein (prior to said step (c)), the steps of (i) evaluating for each of a plurality of other candidate domains one or more metrics; and (ii) selecting another domain from the plurality of other candidate domains based on the metrics. In one embodiment, the metrics comprise one or more parameters characterizing stability of the second domain. In another embodiment, the metrics of the invention include one or more parameters characterizing solubility, biodistribution or non-specific toxicity of the second domain. In one embodiment, the parameters characterizing stability of the second domain include a Tm value of the second domain, and the parameters characterizing solubility, biodistribution or non-specific toxicity of said second domain include a pI value of the second domain. The metrics of the invention may further include metrics characterizing stability of the second domain under one or more different conditions selected from the group consisting of different pH values, different temperatures, different shear stresses, and different freeze/thaw cycles. In one embodiment, the second domain is a constant region domain. In a specific embodiment, the first domain is an antigen binding domain (e.g., Fab domain) and the second domain is an antibody constant region domain (e.g., Fc domain).

In a specific embodiment, the invention provides a method of generating one or more antibodies which bind to a given target, comprising (a) identifying a plurality of candidate antigen binding domains exhibiting a binding affinity for the target above a predetermined threshold level; (b) determining the Tm and/or pI values for each of the plurality of candidate antigen binding domains; (c) selecting one or more antigen binding domains from the plurality based on their Tm and/or pI values; and (d) constructing an antibody using each antigen binding domain selected in step (c) and one or more other domains. In one embodiment, at least some of the antigen binding domains bind different epitopes of the target.

The invention also provides a method of screening one or more multidomain proteins, such as antibodies, which bind to a given target, comprising (a) evaluating for each of a plurality of multidomain proteins one or more metrics of the invention representing one or more therapeutic and/or formulation and/or manufacturing characteristics of candidate domains of the multidomain proteins, wherein the plurality of multidomain proteins exhibits a biological activity above a predetermined threshold level; and (b) selecting one or more multidomain proteins from the plurality based on the metrics representing one or more therapeutic and/or formulation and/or manufacturing characteristics of said multidomain proteins.

The invention also provides a method of engineering a multidomain protein to improve one or more therapeutic and/or formulation and/or manufacturing characteristics without significantly altering other biological activities. The method comprises making one or more modifications (e.g., amino acid substitutions), wherein the modifications (e.g., amino acid substitutions) are such that they improve one or more of the characteristics of the multidomain protein.

In the method of engineering a multidomain protein to have improved improve one or more therapeutic and/or formulation and/or manufacturing characteristics without significantly altering other biological activities, the multidomain protein can be an antibody and the biological activities include, but are not limited to, one or more of the following biological activities: antigen binding, serum half-life, complement fixation, Fc receptor binding and antigen-dependent cytotoxicity of the antibody.

The invention also provides a method of evaluating long term stability of a multidomain protein in a solution, wherein long term stability is defined as less than 5%, 10%, or 20% aggregation upon storage for a predetermined period of time (e.g., 1 to 6 months) at a predetermined temperature (e.g., 4° C.). The method comprises (a) providing a solution of a multidomain protein; (b) denaturing one or more domains of a multidomain protein by heating the solution of the multidomain protein; (c) determining if the domains refold upon cooling; and (d) classifying the multidomain protein as having long term stability in the solution if the domains are determined to refold in step (c).

The invention also provides a method of identifying in a multidomain protein one or more domains, the unfolding of which causes aggregation of the multidomain protein in a solution, comprising (a) denaturing the one or more domains by heating the solution of the multidomain protein; (b) determining if one or more of the domains refold upon cooling; and (c) identifying one or more domains that do not refold upon cooling in step (b), thereby identifying a domain or domains, the unfolding of which causes aggregation of the multidomain protein in the solution.

The invention also provides a method of engineering a multidomain protein to have improved long term stability in a solution, wherein said long term stability is defined as less than 5%, less than 10%, or less than 20% aggregation upon storage for a predetermined period of time at a predetermined temperature. The method comprises (a) modifying a domain of a multidomain protein by replacing one or more amino acid residues in the domain to generated a modified domain; (b) denaturing the modified domain by heating a solution of a multidomain protein comprising the modified domain; (c) determining if the modified domain in the multidomain protein refolds upon cooling; and (d) classifying the multidomain protein containing the modified domain as having improved long term stability if the modified domain is determined to refold in step (c). In certain embodiments, the unfolding of the domain prior to modification causes the aggregation of the multidomain protein. In the method of engineering a multidomain protein to have improved long term stability, the multidomain protein can be an antibody. It is contemplated that steps (a) to (d) may be performed on an isolated domain. For example, a Fab domain may be isolated, modified denatured, renatured and classified. In one embodiment, the identified domain having improved long term stability is used in the generation of a multidomain protein. In another embodiment, the modified domain is an antigen binding domain (e.g., Fab domain). In still another embodiment, the modified domain is a constant region domain (e.g., Fc domain).

The invention further provides a method of screening for a multidomain protein which has improved long term stability in a solution, wherein long term stability is defined as less than 5%, 10%, or 20% aggregation upon storage for a predetermined period of time at a predetermined temperature comprising (a) denaturing respectively two or more multidomain proteins that are members of a population of multidomain proteins, wherein each multidomain protein comprises a different modified domain, the modified domains having one or more amino acid residues substituted, wherein the denaturing is accomplished by heating a solution of one of the multidomain proteins comprising a modified domain; (b) determining if the modified domain in each of the multidomain proteins denatured in step (a) refolds upon cooling; and (c) identifying the multidomain proteins containing a modified domain determined to refold in step (b) as having improved long term stability. In one embodiment, the method further comprises generating the population of multidomain proteins comprising different modified domains. In certain embodiments the unfolding of the domain prior to modification causes aggregation of the multidomain protein.

In the method of screening for a multidomain protein which has improved long term stability, the multidomain protein can be an antibody. In one embodiment, the domain is an antigen binding domain (e.g., a Fab domain). In another embodiment, the domain is a constant region domain (e.g., a Fc domain). It is contemplated that the methods of the invention may be performed on an isolated domain or domains. In one embodiment, the modified domain determined to refold upon cooling is used in the generation of a multidomain protein. In one embodiment, said denaturation and renaturation steps are carried out by generating a thermal denaturation/renaturation curve, e.g., using differential scanning calorimetry.

The invention provides a method of engineering a multidomain protein to have improved stability. The method comprises (a) modifying a domain of a multidomain protein by replacing one or more amino acid residues in the domain to generated a modified domain; (b) determining the Tm of the modified domain; and (c) classifying the multidomain protein containing the modified domain as having improved stability if the domain is determined to have a higher Tm in step (b). Accordingly, the invention also provides engineered multidomain proteins which have a higher Tm than the multidomain protein prior to being engineered. The invention also provides engineered multidomain proteins which have improved stability than the multidomain protein prior to being engineered. In certain embodiments, the Tm of the domain prior to modification is either low or contributes to the multidomain protein have a low Tm.

The invention provides a method of engineering a multidomain protein to have improved solubility and/or lower viscosity. The method comprises (a) modifying a domain of a multidomain protein by replacing one or more amino acid residues in the domain to generated a modified domain; (b) determining the pI of the modified domain; and (c) classifying the multidomain protein containing the modified domain as having improved solubility and/or viscosity if the modified domain is determined to have a higher pI in step (b). In another embodiment of the method, the pI of the multidomain protein containing the modified domain is determined in step (b) and the multidomain protein containing the modified domain is classified as having improved solubility and/or viscosity if the multidomain protein containing the modified domain is determined to have a higher pI in step (b). Accordingly, the invention also provides engineered multidomain proteins which have a higher pI relative to the multidomain protein prior to being engineered. The invention also provides engineered multidomain proteins which have improved solubility and/or lower viscosity relative to the multidomain protein prior to being engineered. In certain embodiments, the pI of the domain prior to modification is either low or contributes to the multidomain protein have a low pI.

The invention further provides a method of engineering a multidomain protein to have reduced non-specific toxicity. The method comprises (a) modifying a domain of a multidomain protein by replacing one or more amino acid residues in the domain to generated a modified domain; (b) determining the pI of the modified domain; and (c) classifying the multidomain protein containing the modified domain as having reduced non-specific toxicity if the modified domain is determined to have a lower pI in step (b). In another embodiment of the method, the pI of the multidomain protein containing the modified domain is determined in step (b) and the multidomain protein containing the modified domain is classified as having reduced non-specific toxicity if the multidomain protein containing the modified domain is determined to have a lower pI in step (b). Accordingly, the invention also provides engineered multidomain proteins which have a lower pI relative to the multidomain protein prior to being engineered. The invention also provides engineered multidomain proteins which have reduced non-specific toxicity relative to the multidomain protein prior to being engineered. In certain embodiments, the domain prior to modification either has a pI or contributes to the multidomain protein having a pI which results in non-specific toxicity.

In addition, the invention provides a method of engineering a multidomain protein to have a specific biodistribution (e.g., intracellular, extravascular, extracellular). The method comprises (a) modifying a domain of a multidomain protein by replacing one or more amino acid residues in the domain to generated a modified domain; (b) determining the pI of the modified domain; and (c) classifying the multidomain protein containing the modified domain as having reduced intracellular localization if the modified domain is determined to have a lower pI in step (b) or as having increased intracellular and/or extravascular localization if the modified domain is determined to have a higher pI in step (b). In another embodiment of the method, the pI of the multidomain protein containing the modified domain is determined in step (b) and the multidomain protein containing the modified domain is classified as having reduced intracellular localization if the multidomain protein containing the modified domain is determined to have a lower pI in step (b) or as having increased intracellular and/or extravascular localization if the multidomain protein containing the modified domain is determined to have a higher pI in step (b). Accordingly, the invention also provides engineered multidomain proteins which have a specific biodistribution. Specifically, the invention provides engineered multidomain proteins which have increased intracellular and/or extravascular localization relative to the multidomain protein prior to being engineered. The invention also provides engineered multidomain proteins which have reduced intracellular localization relative to the multidomain protein prior to being engineered. In certain embodiments, the domain prior to modification either has a pI or contributes to the multidomain protein having a pI which determines the biodistribution.

4. BRIEF DESCRIPTION OF THE FIGURES

FIG. 1. The DSC thermogram of the full length Ca-hG1 Mab molecule is shown in the top panel, while the bottom panel is an overlay of the thermograms obtained from purified Fab and Fc fragments of Ca-hG1 Mab molecule. Two discrete peaks are seen for the Fc domain at approximately 68° C. and 83° C. A single peak is seen for the Fab fragment at approximately 87° C.

Figure 2:
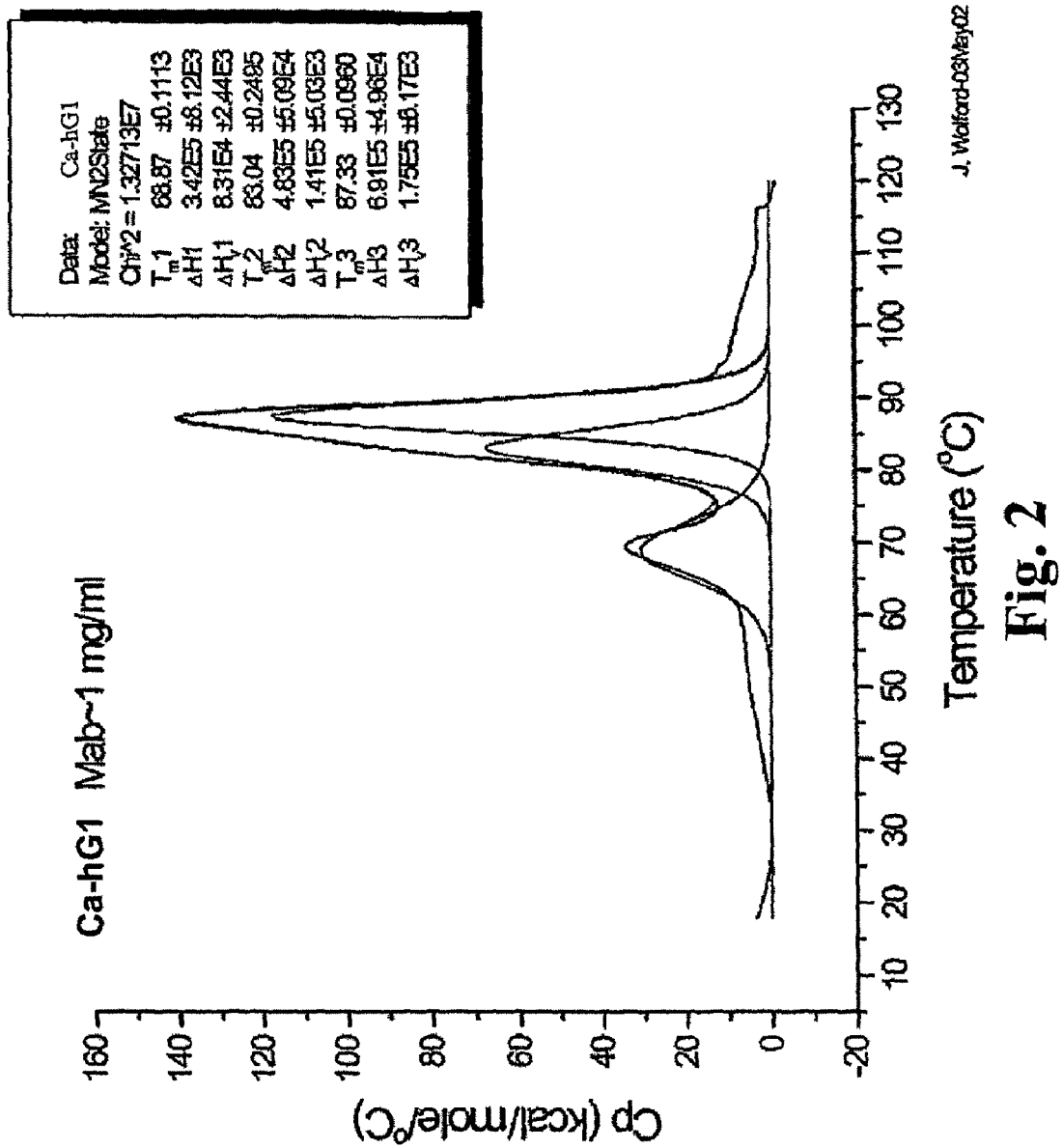

FIG. 2. Deconvolution of the DSC thermogram of the full length Ca-hG1 Mab (see FIG. 1). Three discrete peaks are seen with Tm values of 60° C., 83° C. and 87° C.

Figure 3:
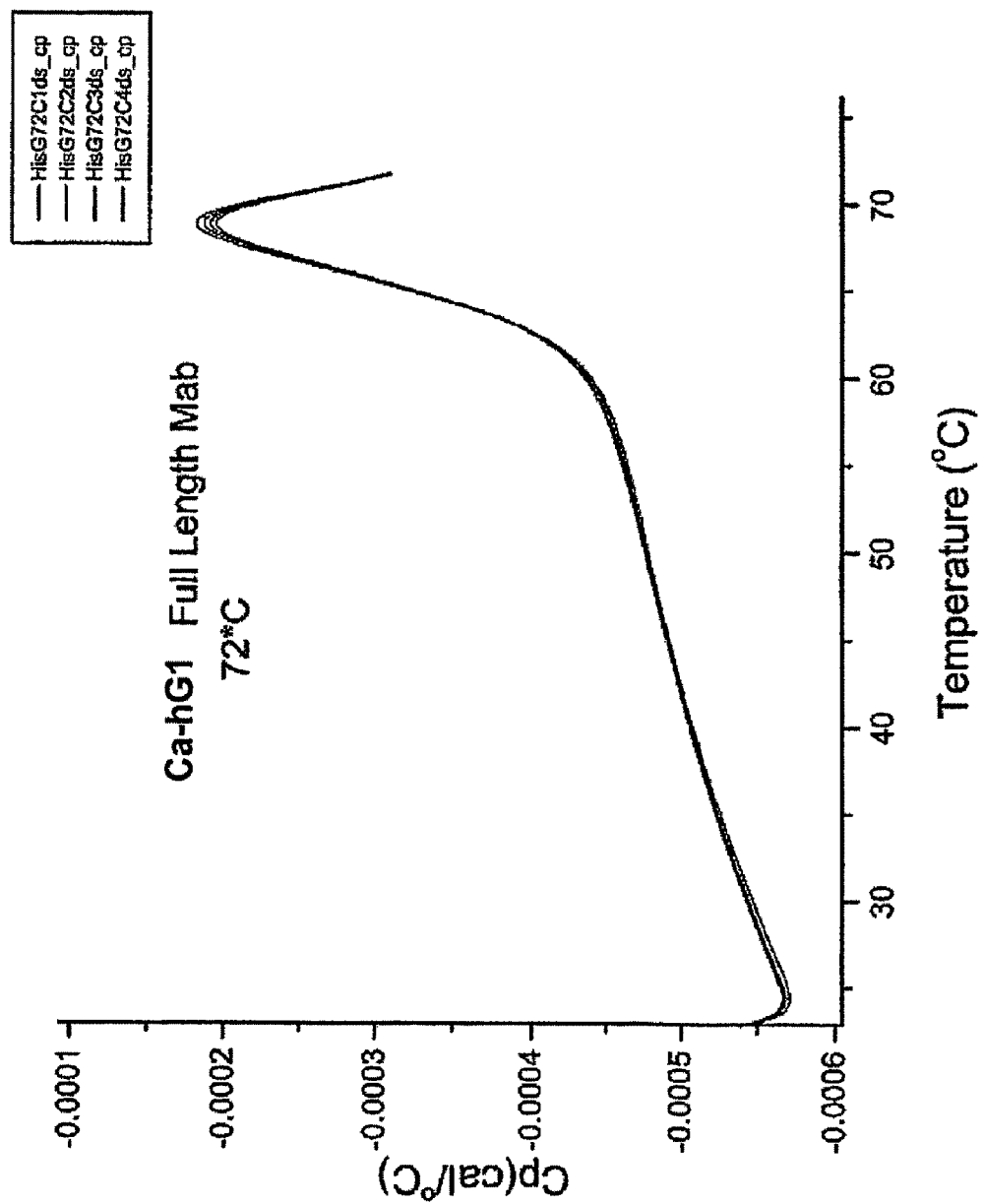

FIG. 3. Overlay of multiple DSC scans of the full length Ca-hG1 Mab, demonstrating reversibility over multiple heating and cooling cycles when heated to 72° C.

Figure 4:
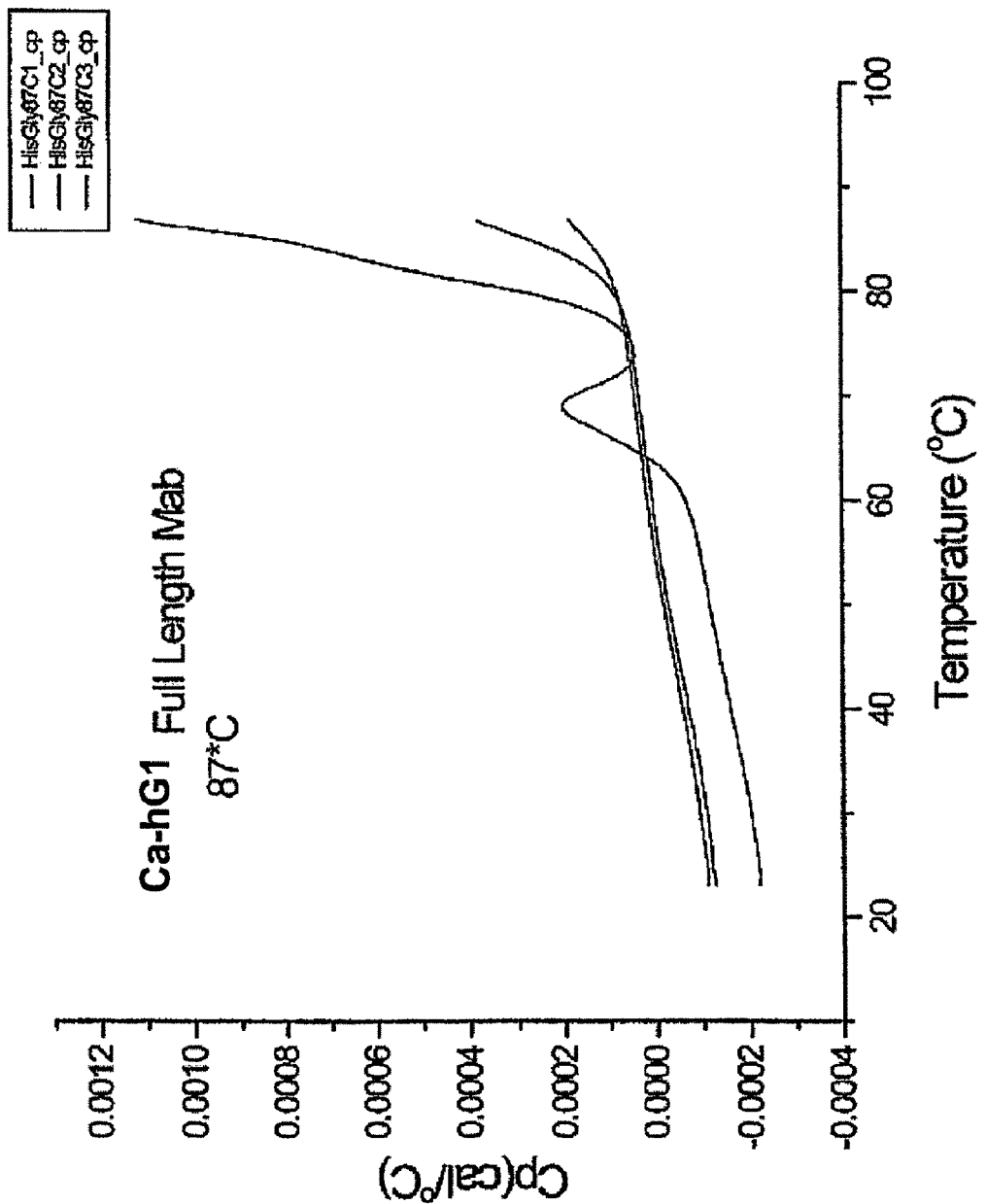

FIG. 4. Overlay of multiple DSC scans of the full length Ca-hG1 Mab, demonstrating less reversibility over multiple heating and cooling cycles when heated to 87° C. than seen for heating to 72° C. (see FIG. 3).

Figure 5:
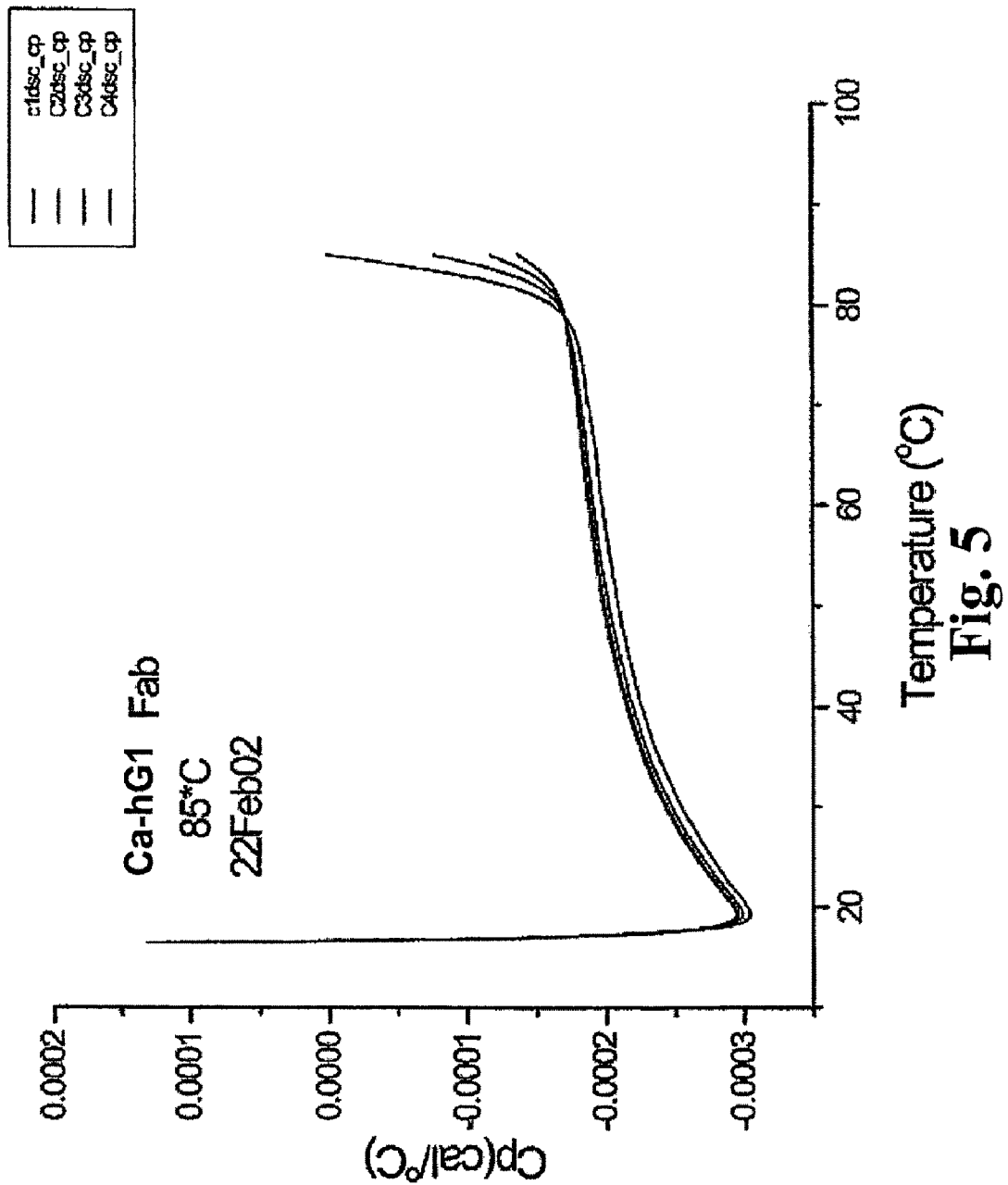

FIG. 5. Overlay of multiple DSC scans of the Fab fragment of Ca-hG1 Mab, demonstrating less reversibility over multiple heating and cooling cycles when heated to 85° C. than seen for heating to 72° C. (see FIG. 3).

Figure 6:
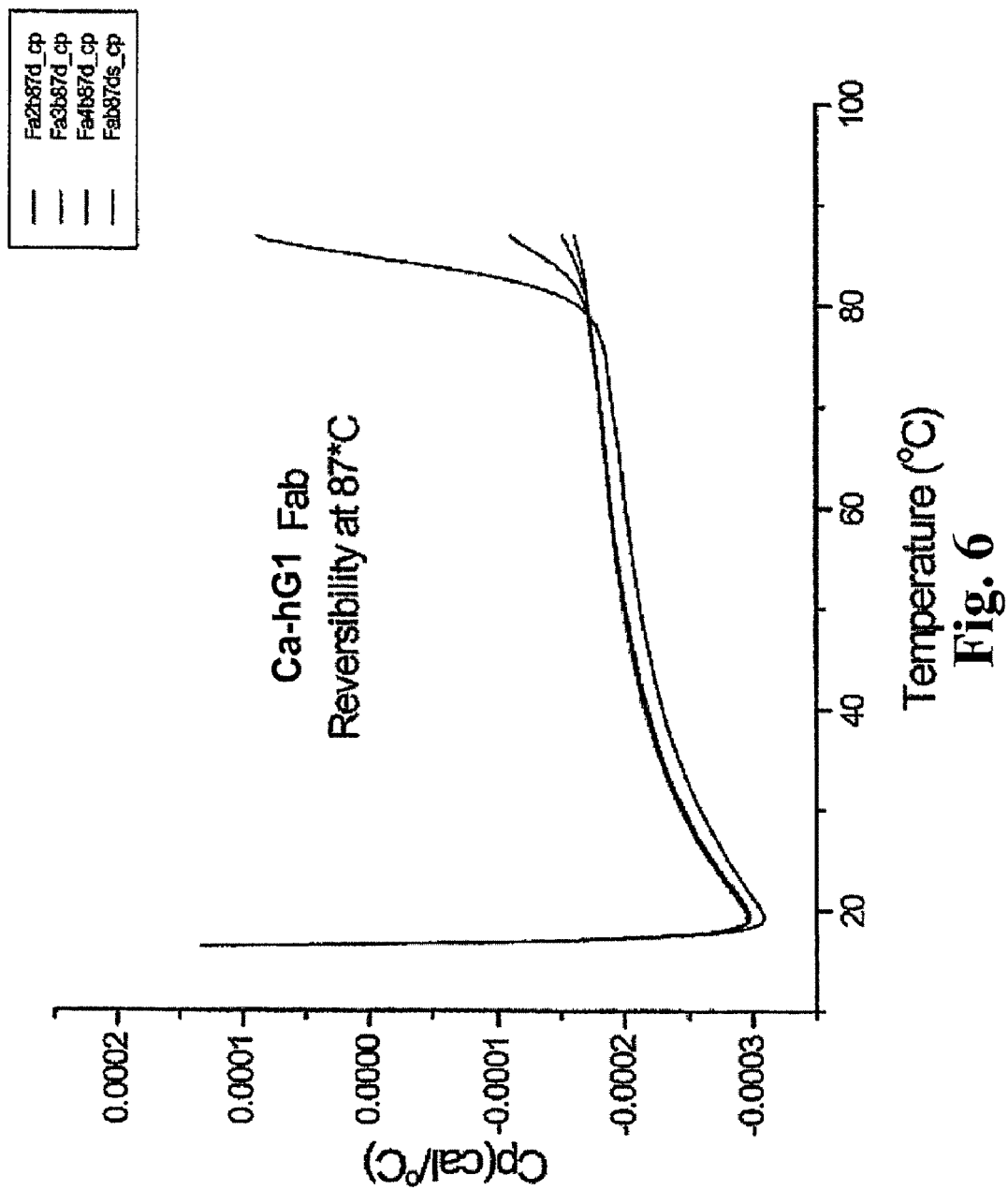

FIG. 6. Overlay of multiple DSC scans of the Fab fragment of Ca-hG1 Mab, demonstrating less reversibility over multiple heating and cooling cycles when heated to 87° C. than seen for heating to 68° C. (see FIG. 7).

Figure 7:
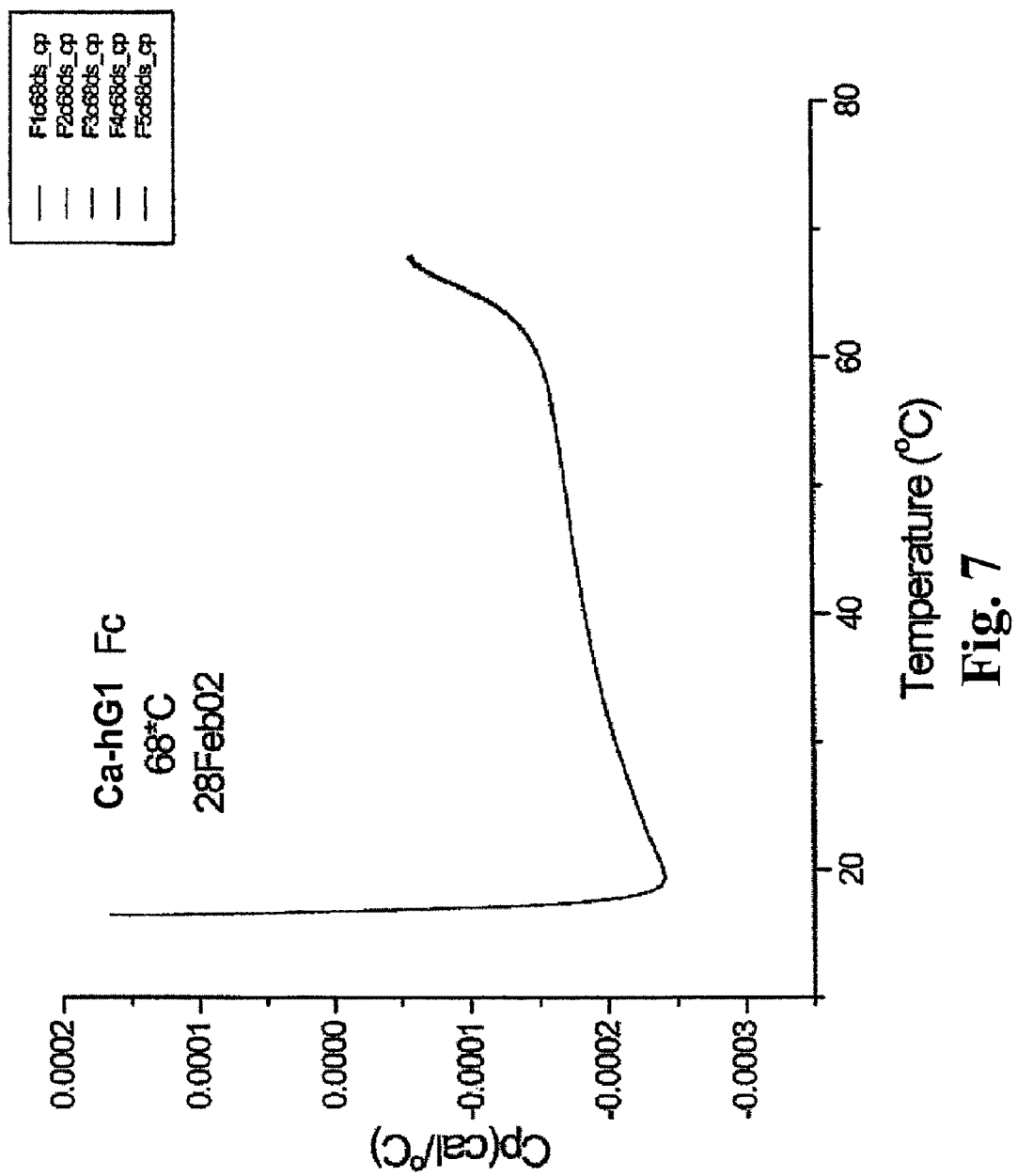

FIG. 7. Overlay of multiple DSC scans of the Fc fragment of Ca-hG1 Mab, demonstrating reversibility over multiple heating and cooling cycles when heated to 68° C.

Figure 8:
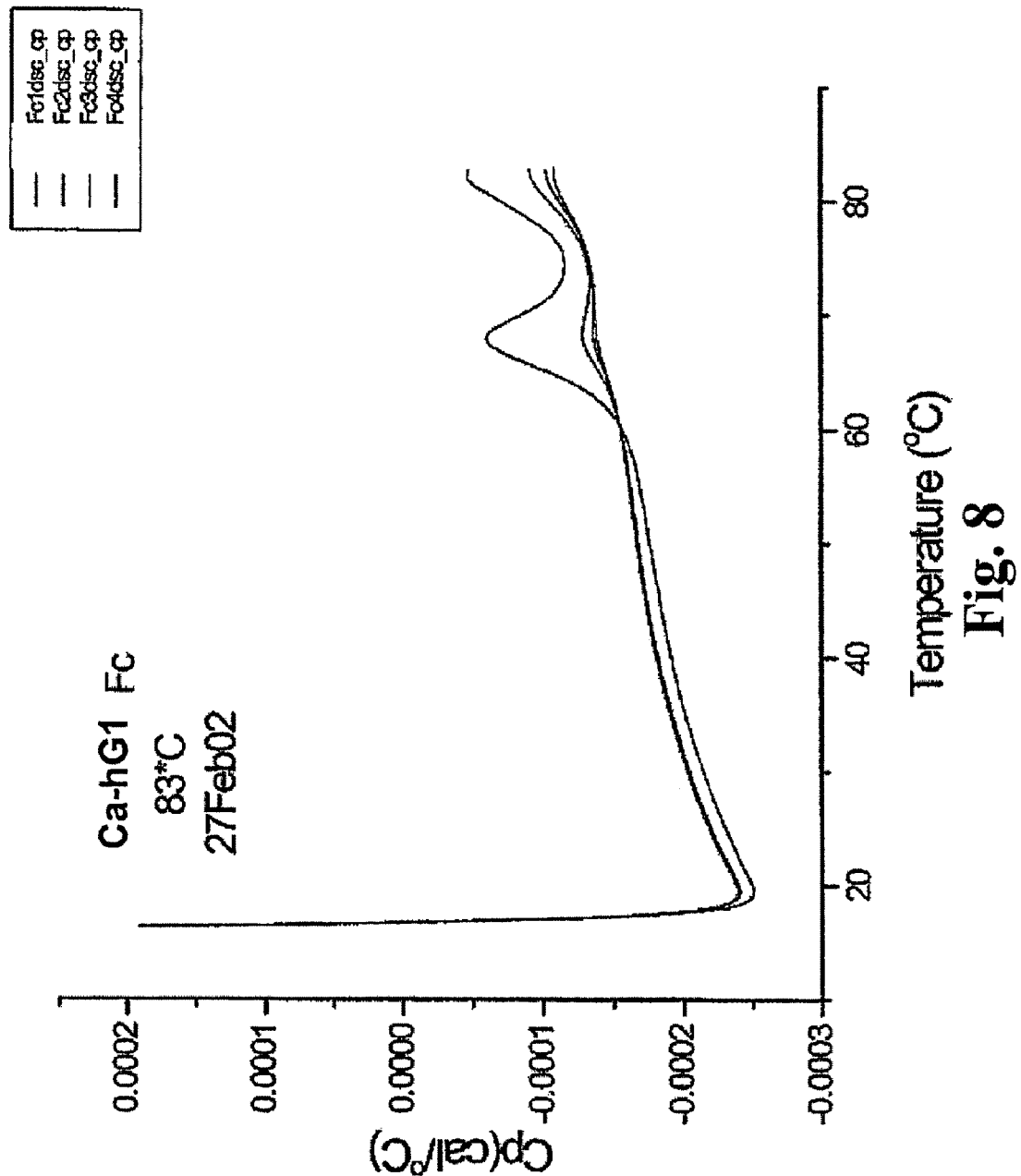

FIG. 8. Overlay of multiple DSC scans of the Fc fragment of Ca-hG1 Mab, demonstrating poor reversibility over multiple heating and cooling cycles when heated to 83° C. than seen for heating to 68° C. (see FIG. 7).

Figure 9:
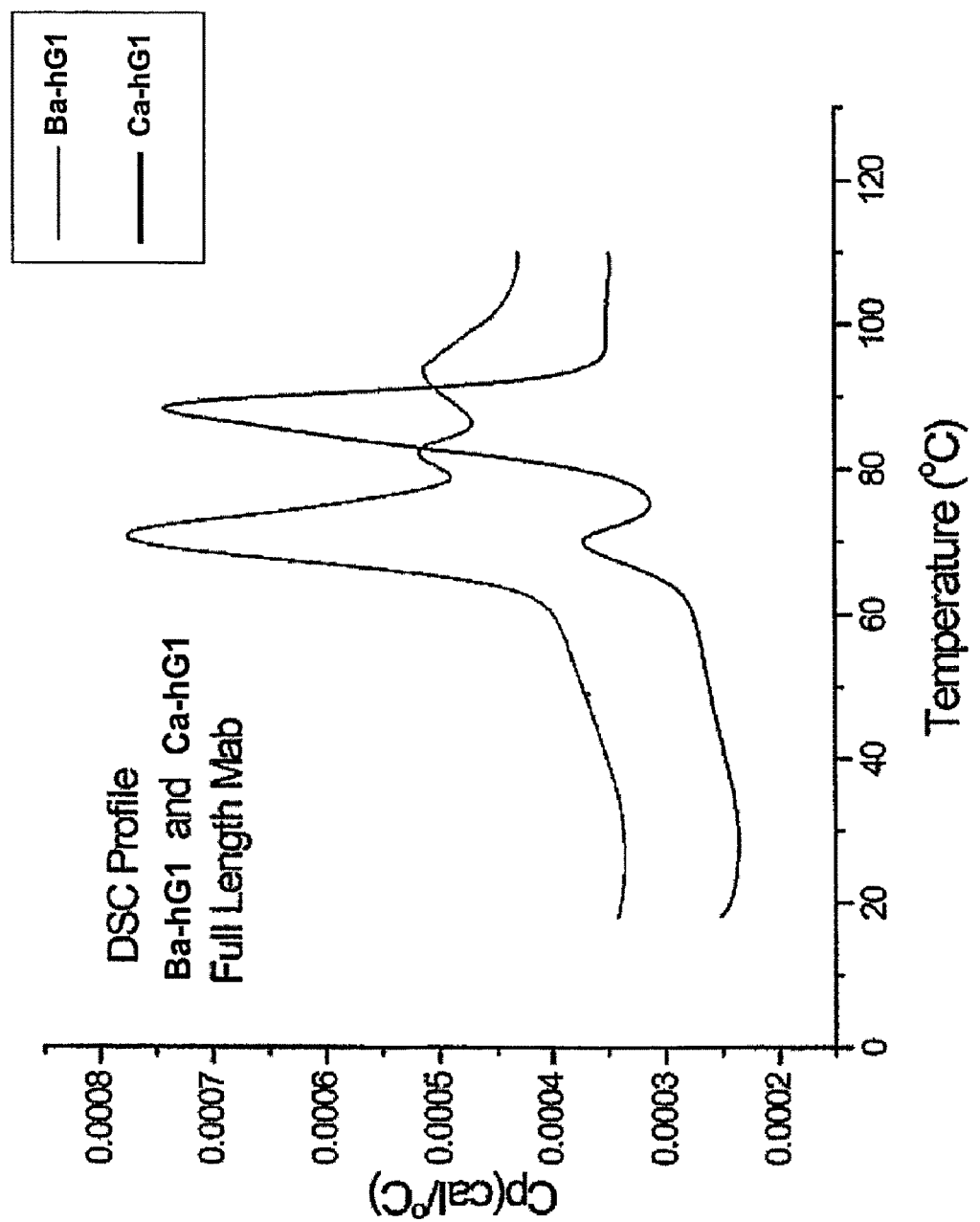

FIG. 9. Overlay of DSC scans of full length Mabs Ba-hG1 and Ca-hG1 showing dramatically different profiles. Ba-hG1 has a major peak at ~72° C. while the major peak for Ca-hG1 is seen at ~87° C.

Figure 10:
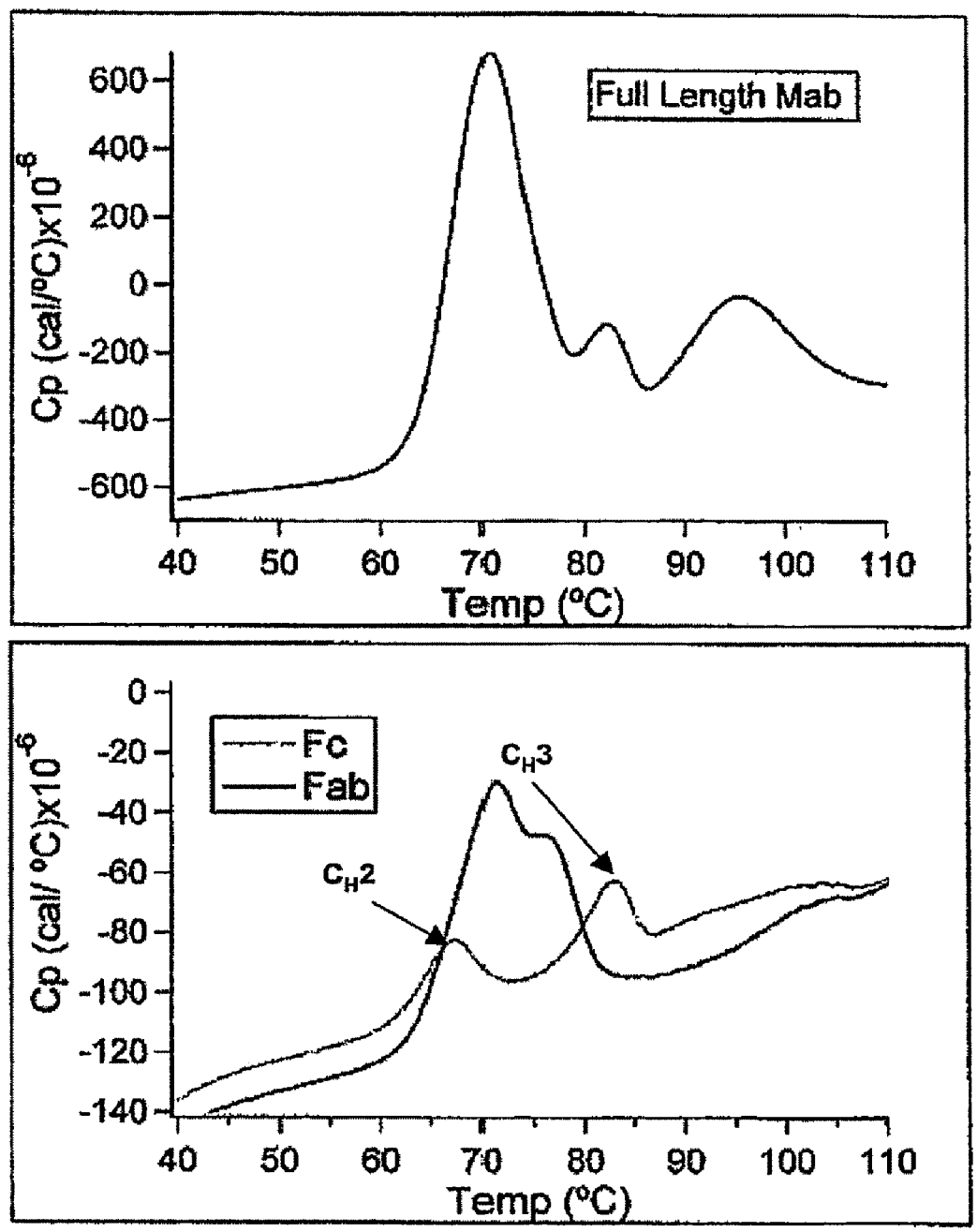

FIG. 10. The DSC thermogram of the full length Ba-hG1 Mab molecule is shown in the top panel, while the bottom panel is an overlay of the thermograms obtained from purified Fab and Fc fragments of Ba-hG1 Mab molecule. Two discrete peaks are seen for the Fc domain at approximately 67° C. and 83° C. Two overlapping peaks are seen for the Fab fragment at approximately 72° C. and 76° C.

Figure 11:
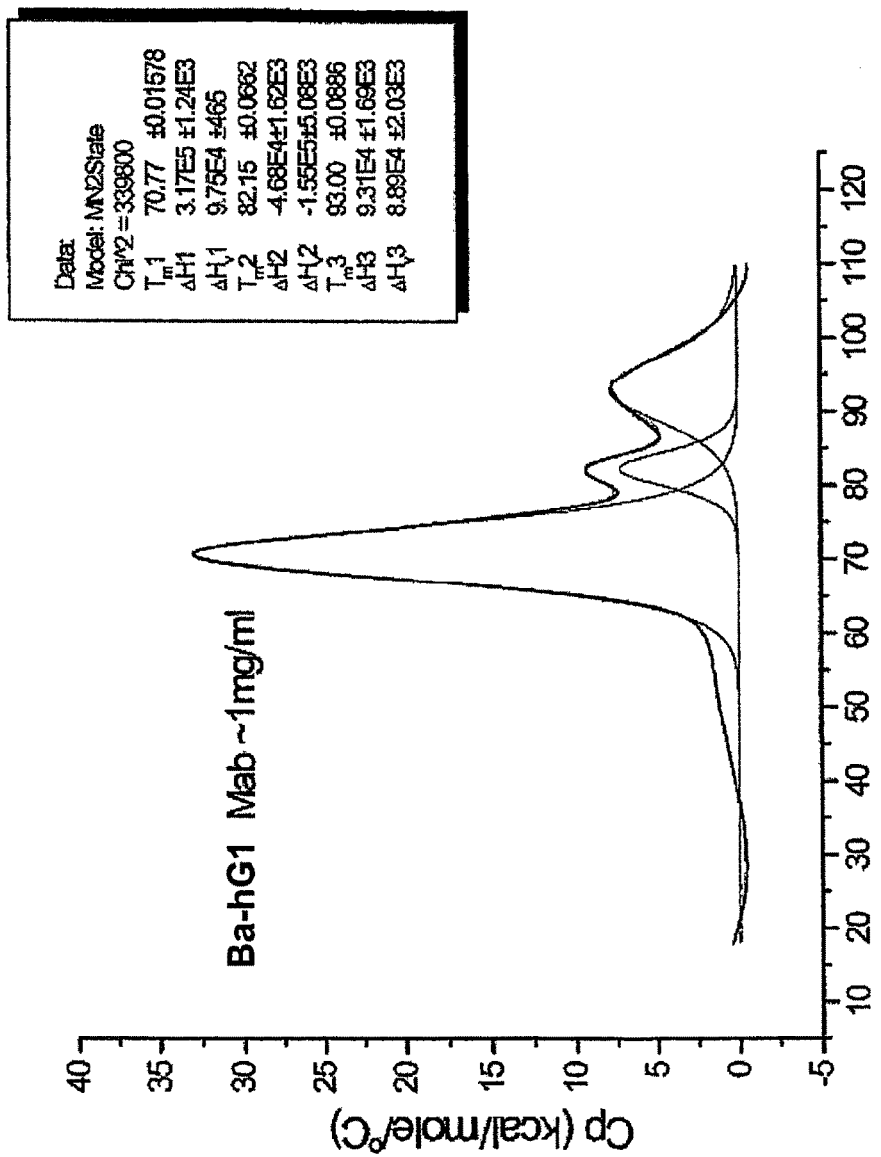

FIG. 11. Deconvolution of the DSC thermogram of the full length Ba-hG1 Mab (see FIG. 10). Three discrete peaks are seen with Tm values of 71° C., 82° C. and 93° C.

Figure 12:
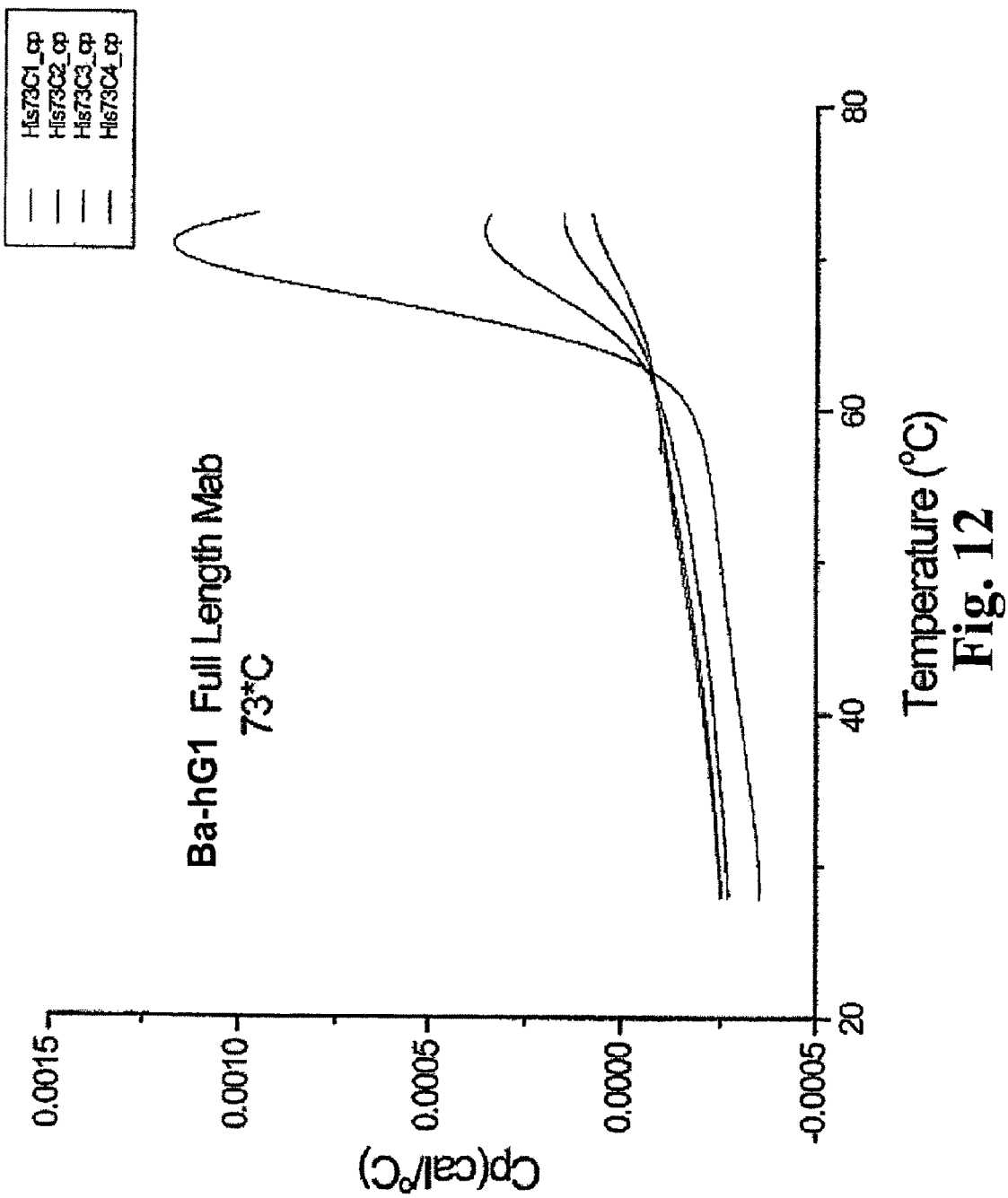

FIG. 12. Overlay of multiple DSC scans of full length Ba-hG1 Mab, demonstrating less reversibility over multiple heating and cooling cycles when heated to 70° C. than seen for the Fab fragment alone heated to 71° C. (see FIG. 14).

Figure 13:
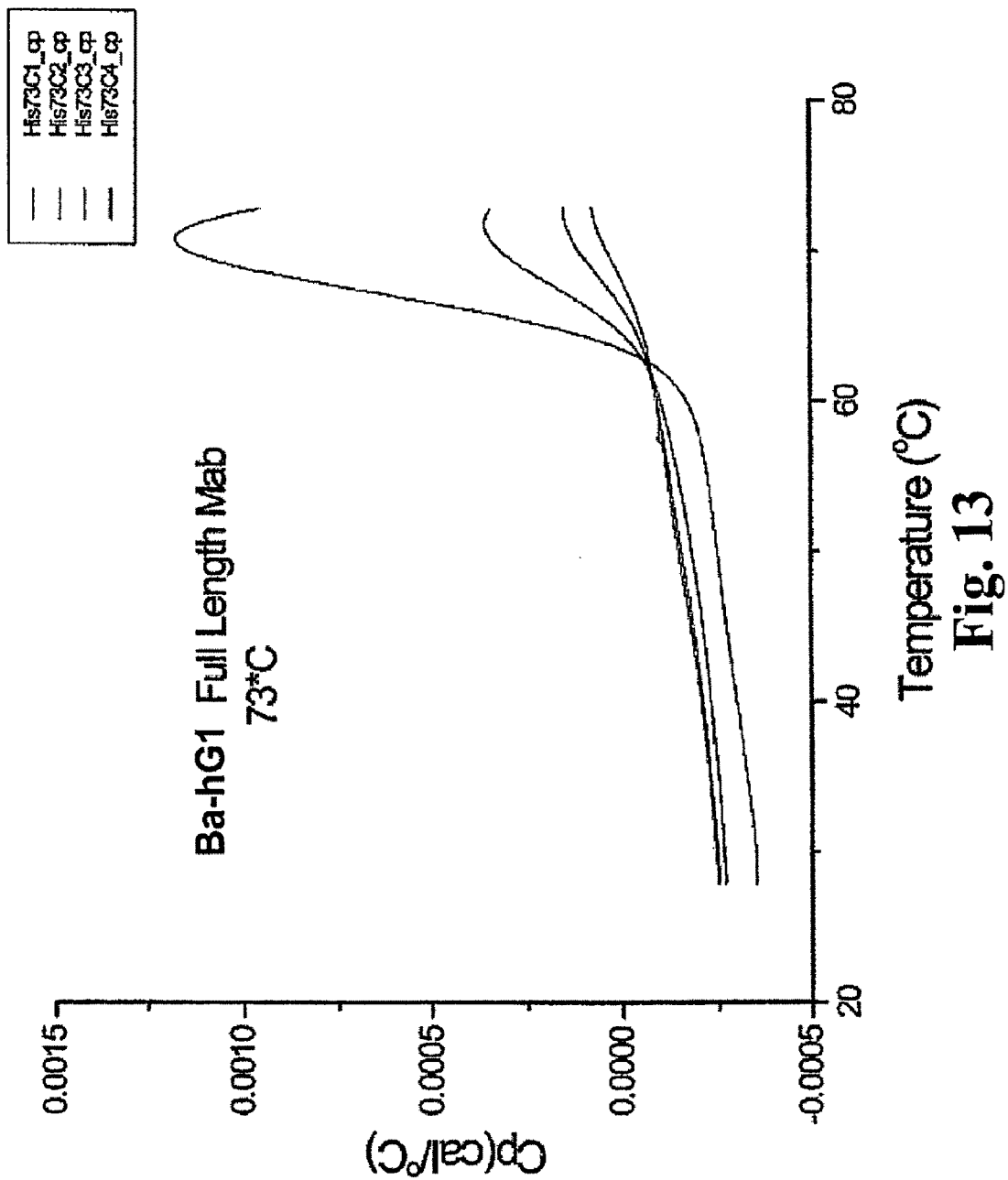

FIG. 13. Overlay of multiple DSC scans of full length Ba-hG1 Mab, demonstrating less reversibility over multiple heating and cooling cycles when heated to 73° C. than seen for the Fab fragment alone heated to 71° C. (see FIG. 14).

Figure 14:
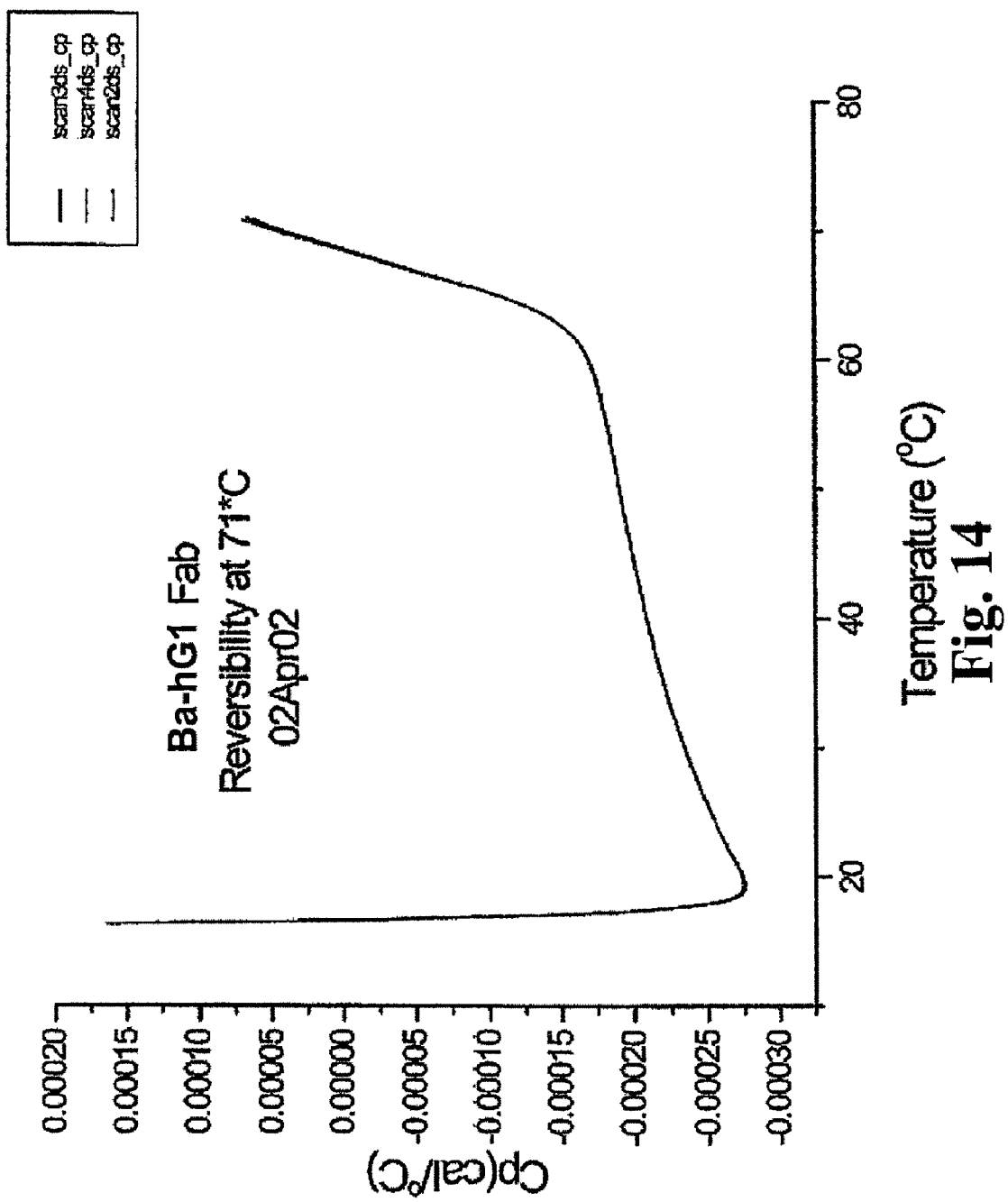

FIG. 14. Overlay of multiple DSC scans of the Fab fragment of Ba-hG1 Mab, demonstrating reversibility over multiple heating and cooling cycles when heated to 71° C.

Figure 15:
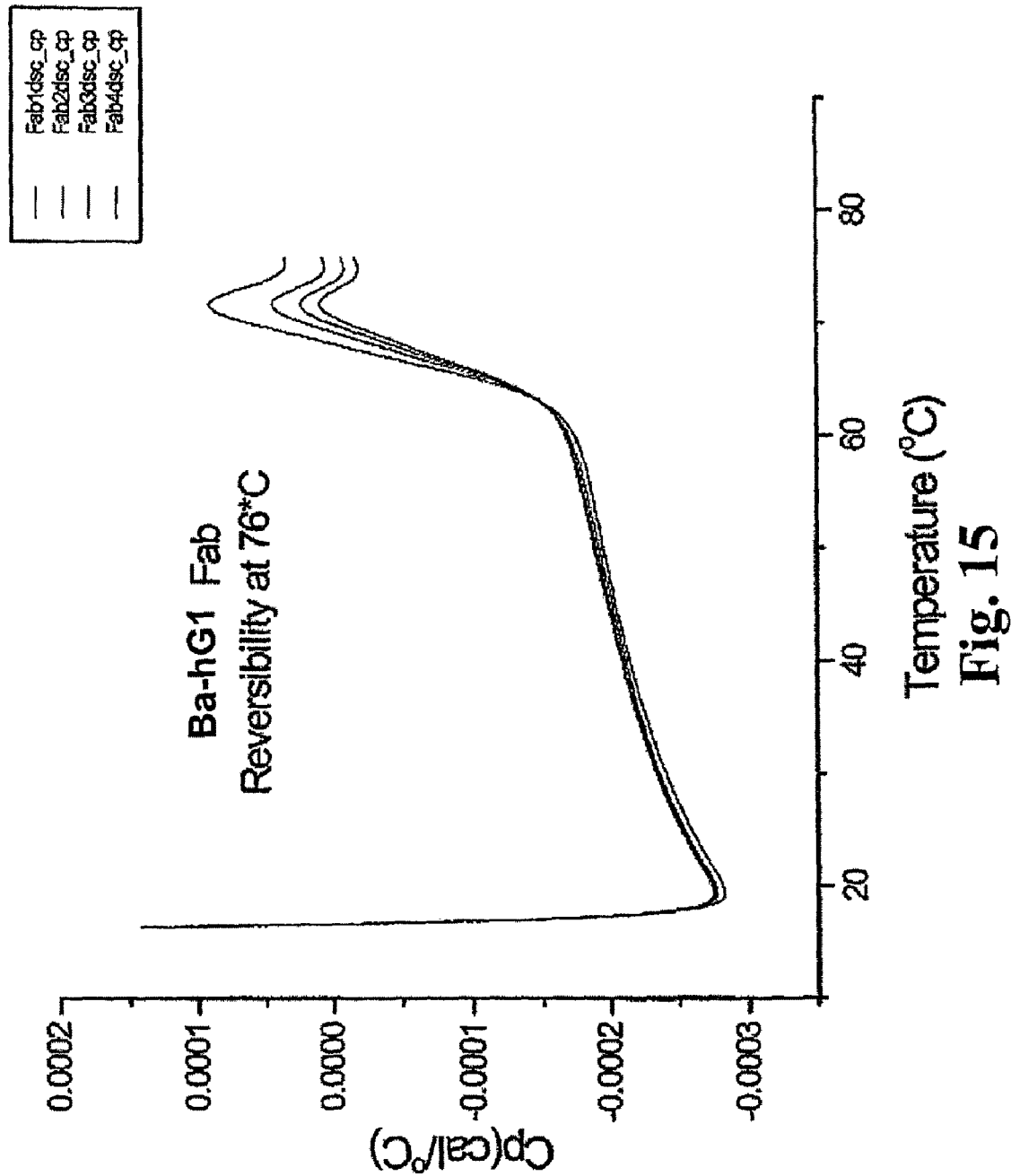

FIG. 15. Overlay of multiple DSC scans of the Fab fragment of Ba-hG1 Mab, demonstrating less reversibility over multiple heating and cooling cycles when heated to 76° C. than seen for heating to 71° C. (see FIG. 14).

Figure 16:
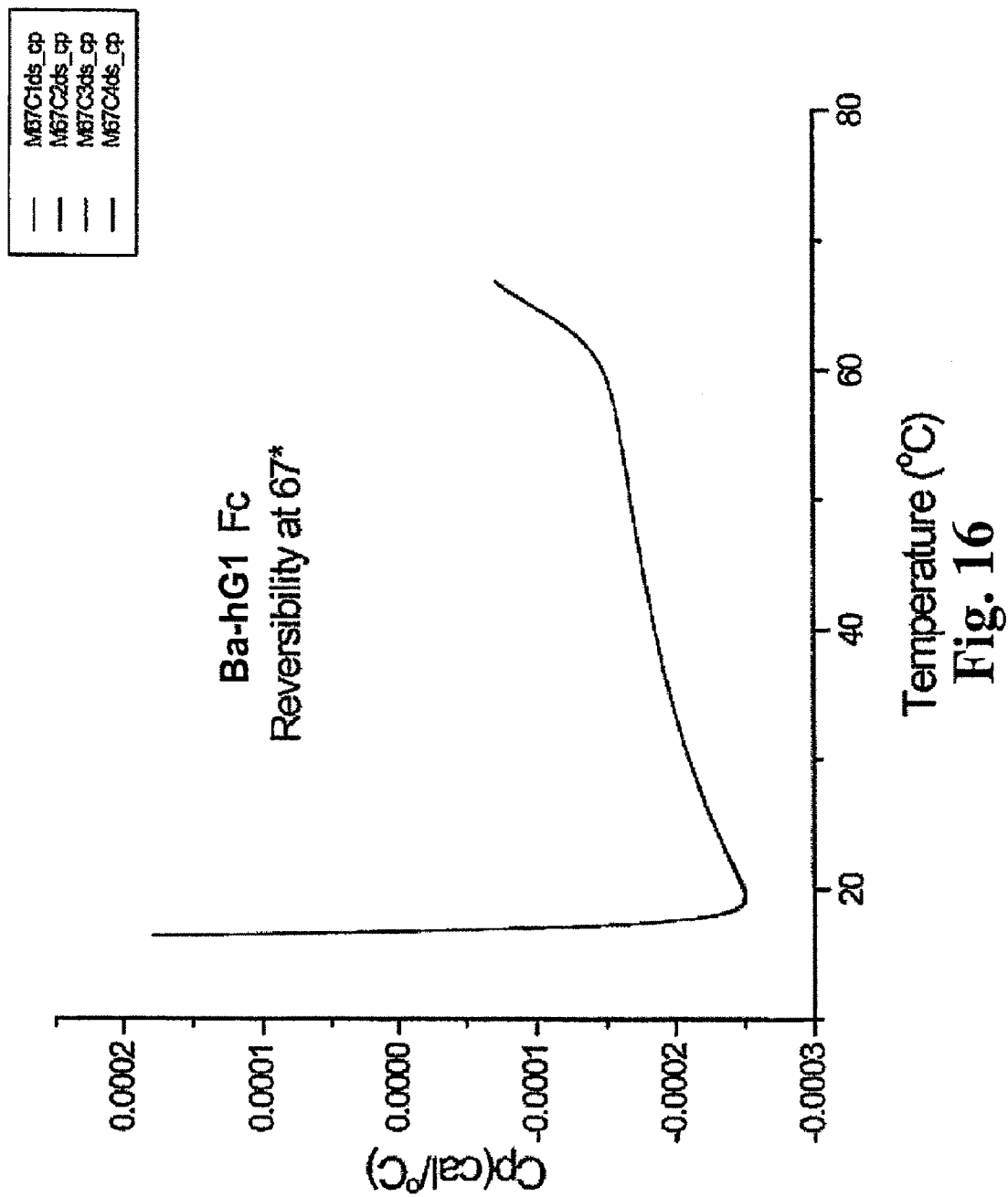

FIG. 16. Overlay of multiple DSC scans of the Fc fragment of Ba-hG1 Mab, demonstrating reversibility over multiple heating and cooling cycles when heated to 67° C.

Figure 17:
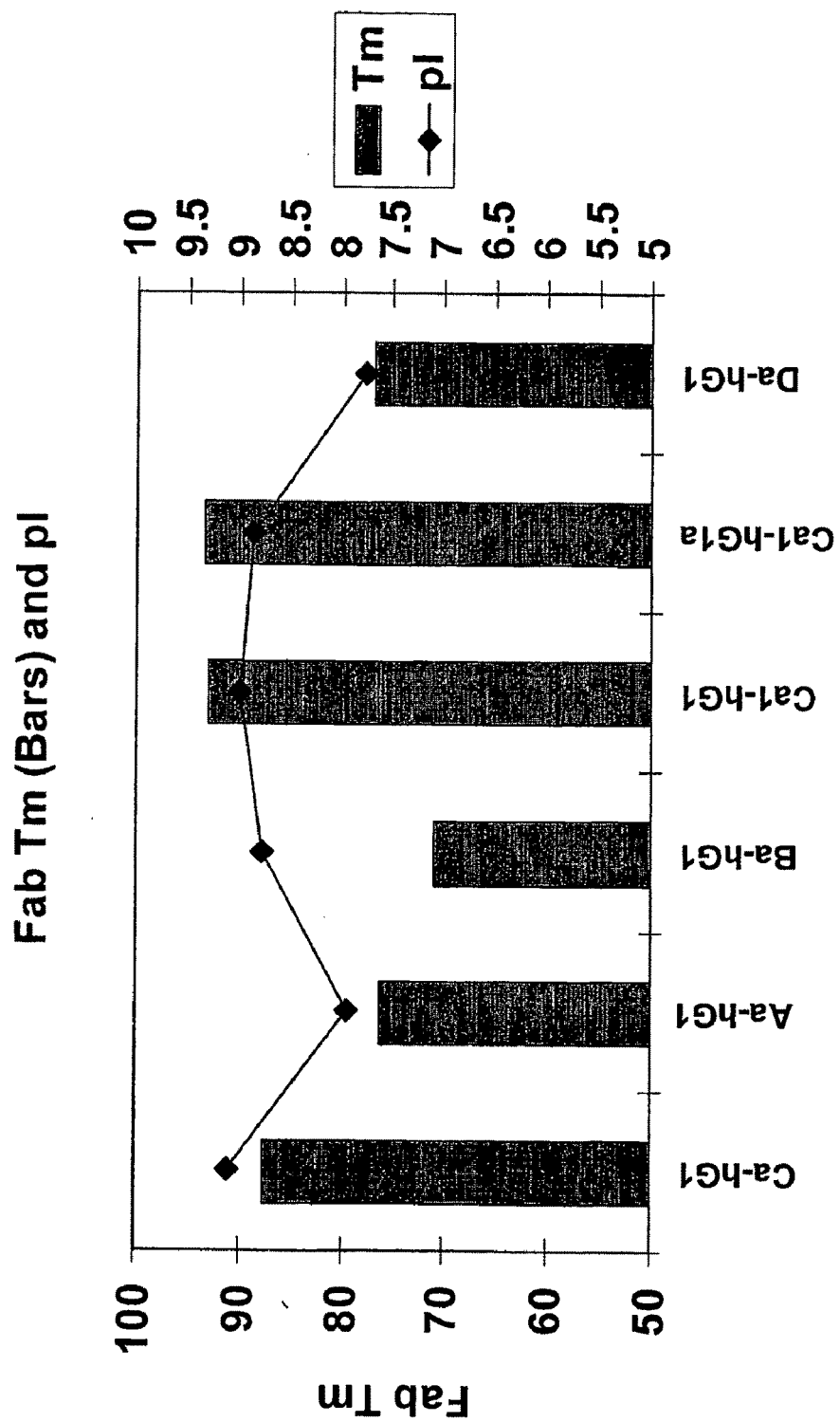

FIG. 17. Graphical representation of the IEF and DSC analysis for a different panel of antibodies. Antibodies Ca-hG1, Ca1-hG1 and Ca1-hG1a are highly related, recognizing the same protein epitope and differing by only a few amino acids. The remaining antibodies, As-hG1, Ba-hG1 and Da-hG1 are unrelated.

FIG. 18. Analysis of a panel of different antibodies which bind to a variety of epitopes present on a single protein. These antibodies have a common Fc domain and vary only in their Fab regions A) Isoelectric focusing (IEF) demonstrate that there is a wide range of pI values (e.g., ~7.8 to ~9.2) for the different antibodies. B) Differential scanning calorimetry (DSC) analysis indicates that there is a wide range of Tm values (e.g., ~66° C. to ~90° C.) for the different antibodies. C) Graphical representation of the IEF and DSC analysis for the panel of antibodies.

Figure 19:
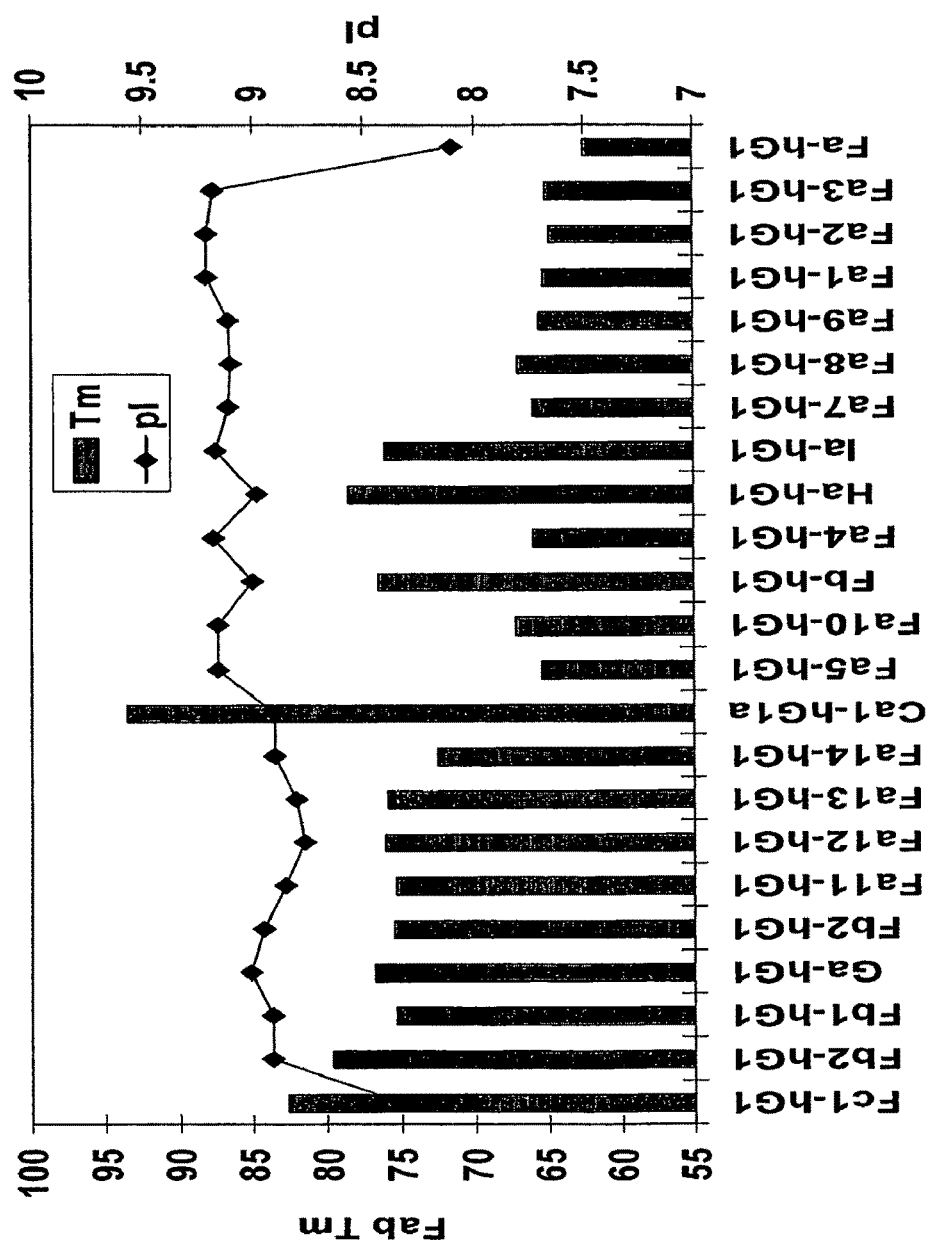

FIG. 19. Graphical representation of the IEF and DSC analysis for a different panel of antibodies which bind to a variety of epitopes present on a single protein. Also plotted are several antibodies used in earlier studies and two chimeric antibodies generated by combining the heavy and light chains from two different antibodies. All of these antibodies have a common Fc domain and vary only in their Fab regions.

Figure 20:
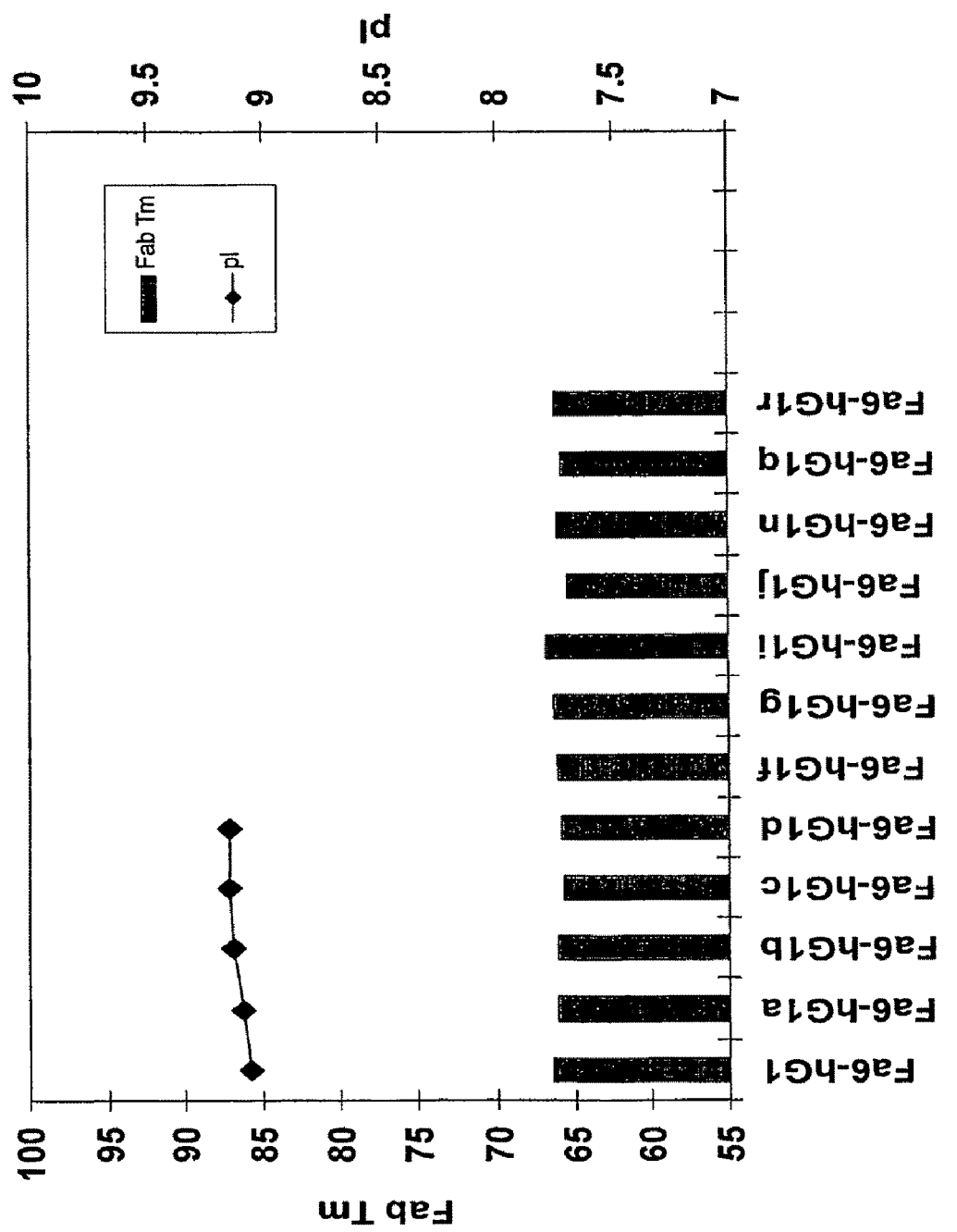

FIG. 20. Graphical representation of the IEF and DSC analysis of a panel of antibodies which are identical except for mutations in their hinge region.

Figure 21:
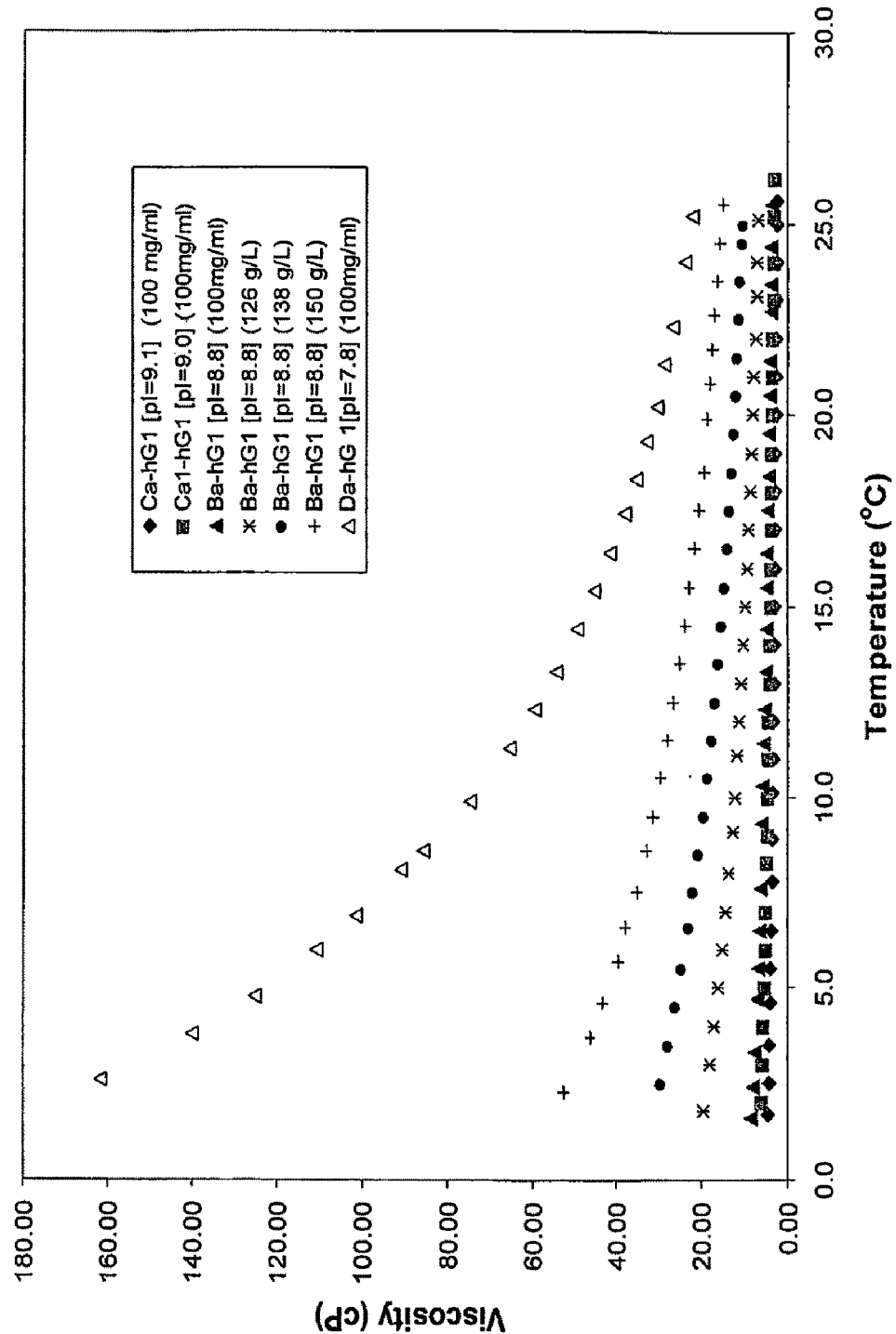

FIG. 21. Viscosity analysis for several of the antibodies analyzed in FIG. 17. Each antibody was analyzed at 100 mg/ml, in addition Ba-hG1 was analyzed at 126 mg/ml, 138 mg/ml and 150 mg/ml.

FIG. 22. Aggregation rate vs. Fab Tm. Panel A plots the aggregation rate of several Ba-hG1, Da-hG1, Ca-hG1 and Ca1-hG1 in relation to the Tm of the Fab region. Panel B plots the aggregation over time for the isolated Fc region and Fab domains of Ca-hG1 and Ba-hG1.

Figure 23:
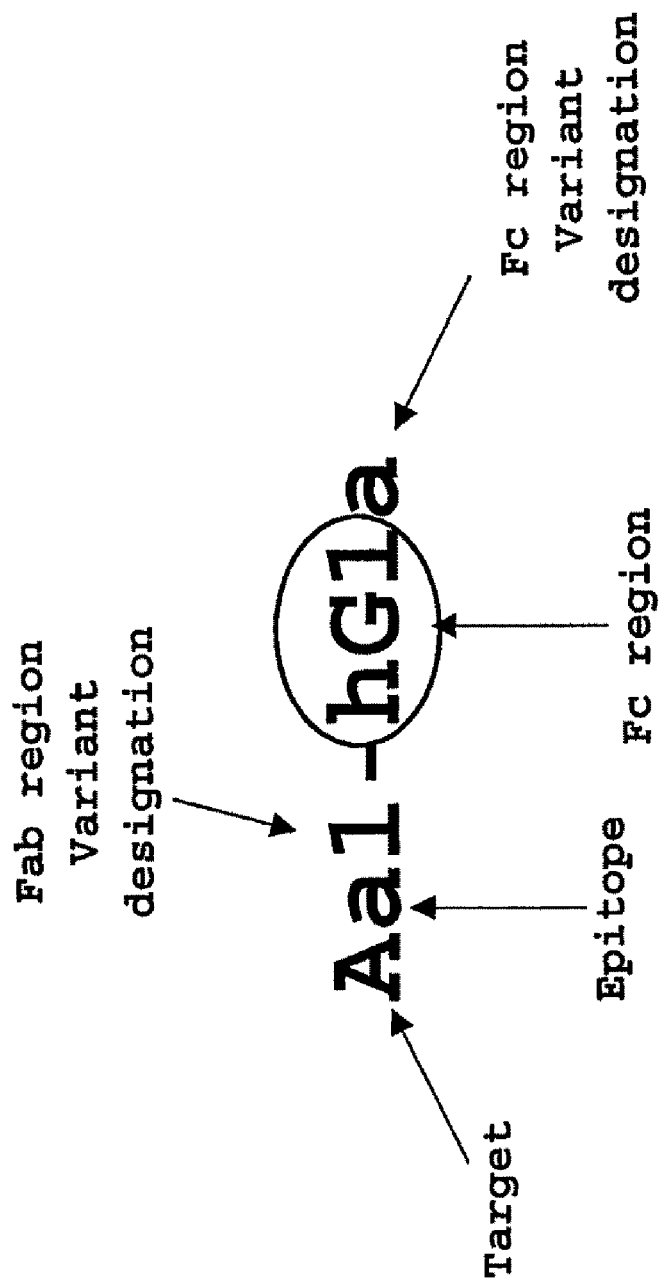

FIG. 23. Antibody naming scheme used in this application. First 3 characters identify the antigen binding domain: the capital letter designates the target, the lower case letter designates a particular epitope of the target, the number designates the variant of the antibody (for simplicity reasons, 0 is often omitted). The last 4 characters identify the Fe domain: the first 3 characters identify the Fc domain, the last lower case letter designates the Fc variant. The example in FIG. 23, Aa1-hG1a, thus identifies variant "1" of an antibody that binds epitope "a" of target "A" and has variant "a" of a human gamma-1 (hG1) as its Fc domain.

Figure 24:
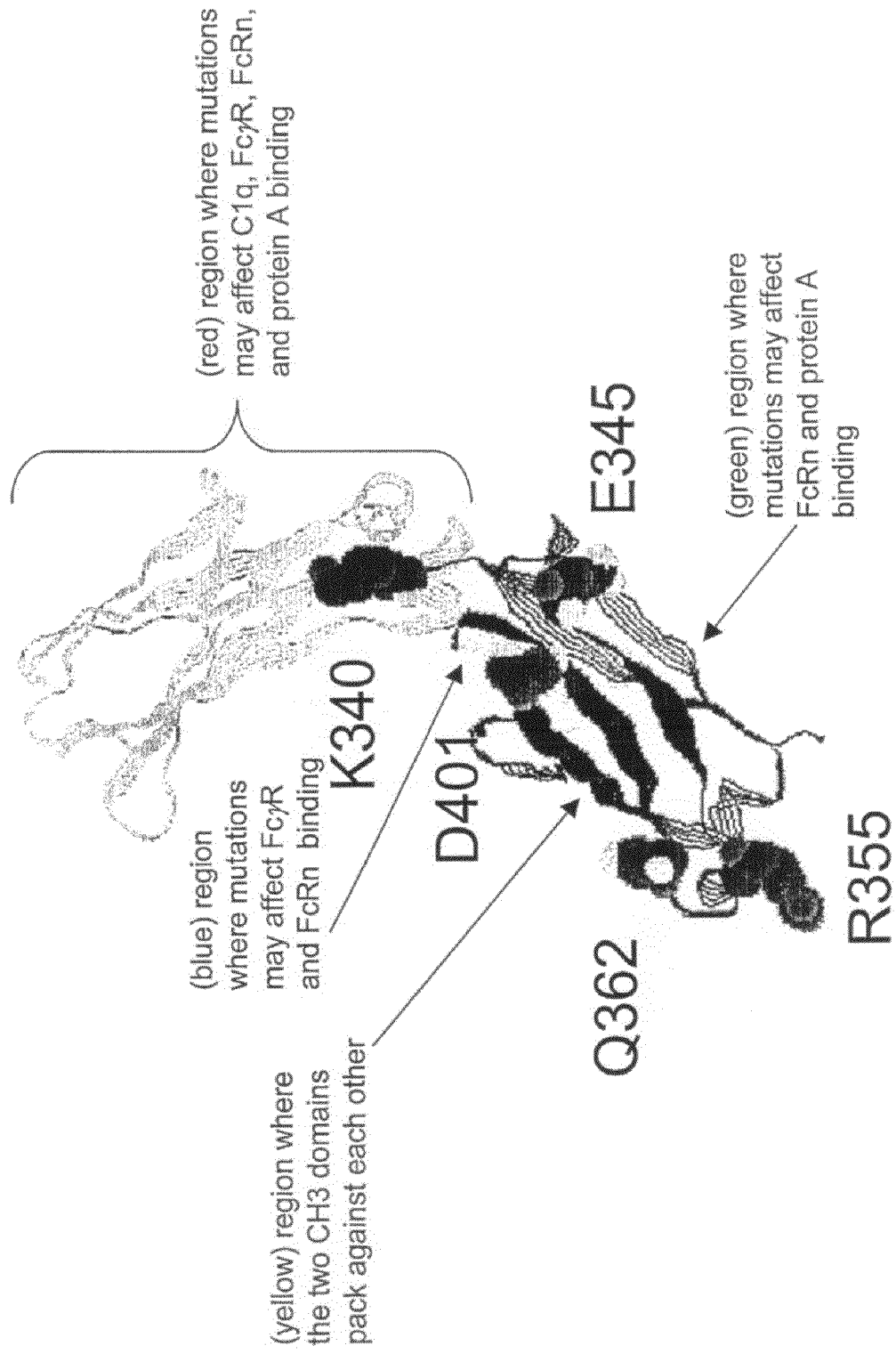

FIG. 24. Ribbon diagram of CH2 and CH3 of the human Fc showing the location of the initial five residues where substitutions were made. This illustration is a side view of a human Fc showing only one CH2 domain (top) and one CH3 domain (bottom). Residues that were substituted are spacefilled. The red indicates a region where mutations may affect C1q, FcγR, FcRn, and protein A binding, the blue indicates a region where mutations may affect FcγR and FcRn binding, and the green indicates a region where mutations may affect FcRn and protein A binding. The yellow region is where the two CH3 domains pack against each other.

Figure 25:
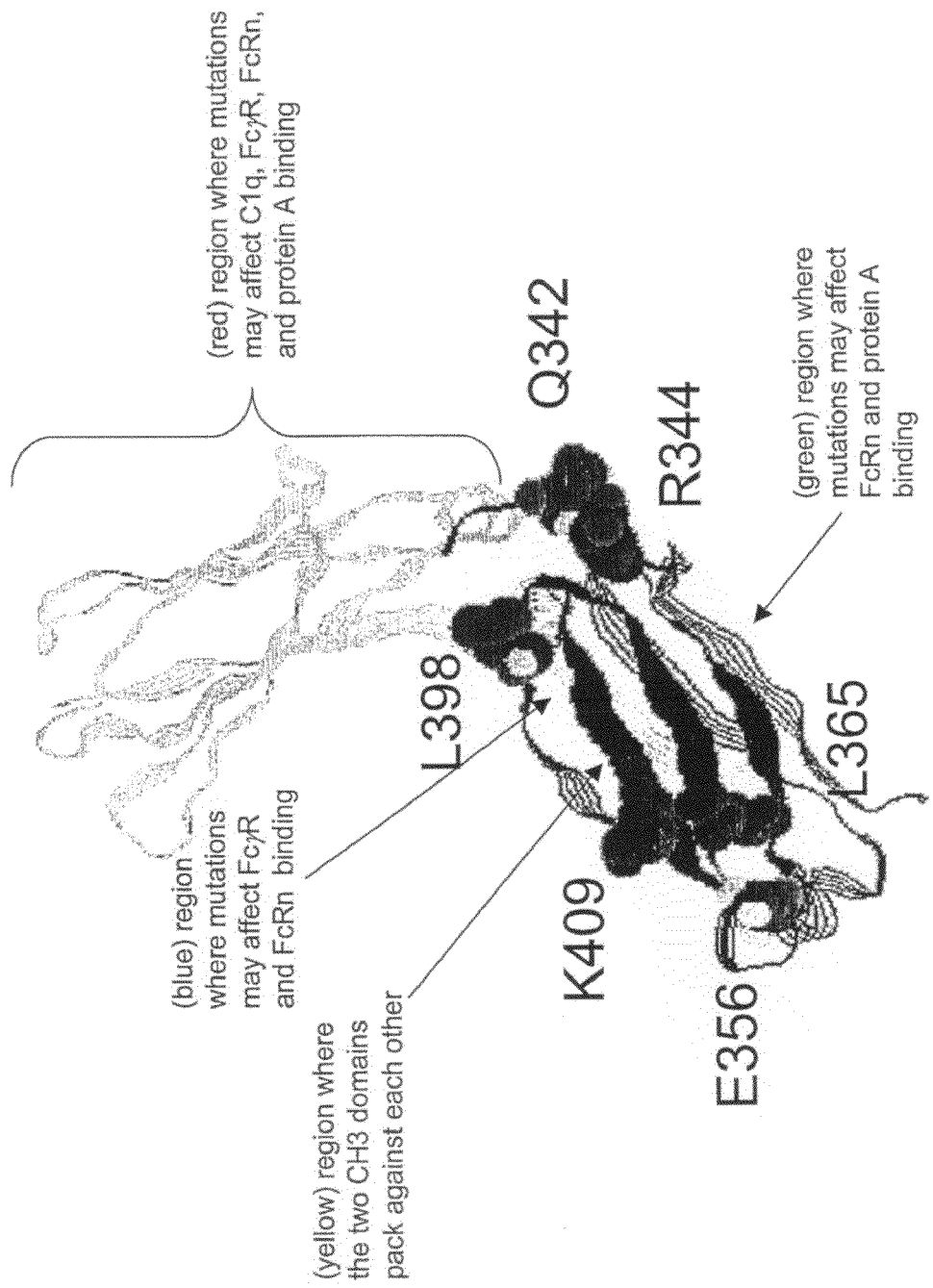

FIG. 25. Ribbon diagram of CH2 and CH3 of the human Fc showing the location of six additional residues where substitutions were made. The orientation is the same as in FIG. 1 and the coloration conveys the same meaning as described in FIG. 1. Substituted residues are spacefilled.

Figure 26:
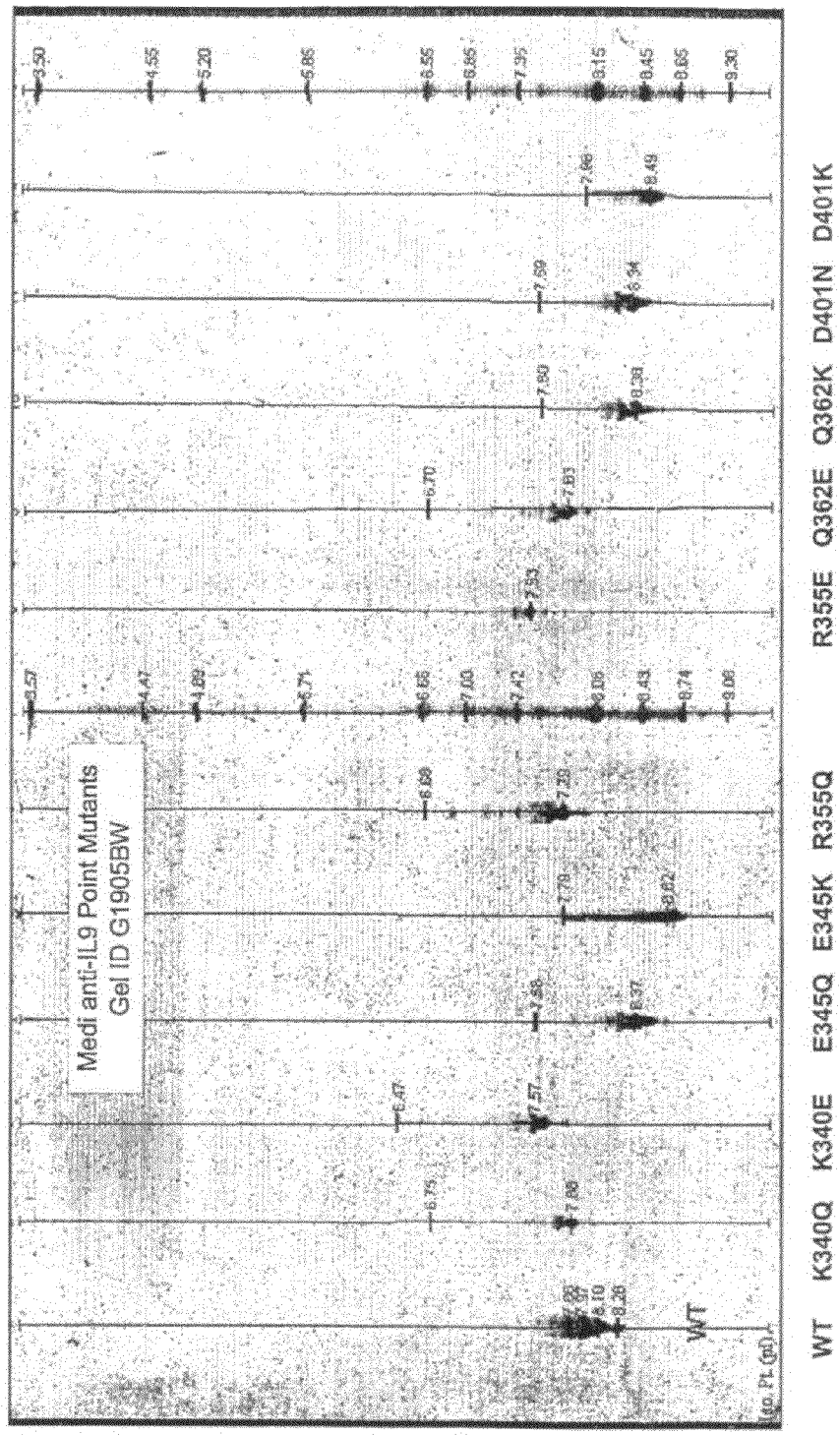

FIG. 26. IEF gel of the first ten single substitutions made. The pI was determined by measuring the migration of the band with the highest intensity in a given lane. The wild type antibody control (WT) was produced in NSO cells.

Figure 27:
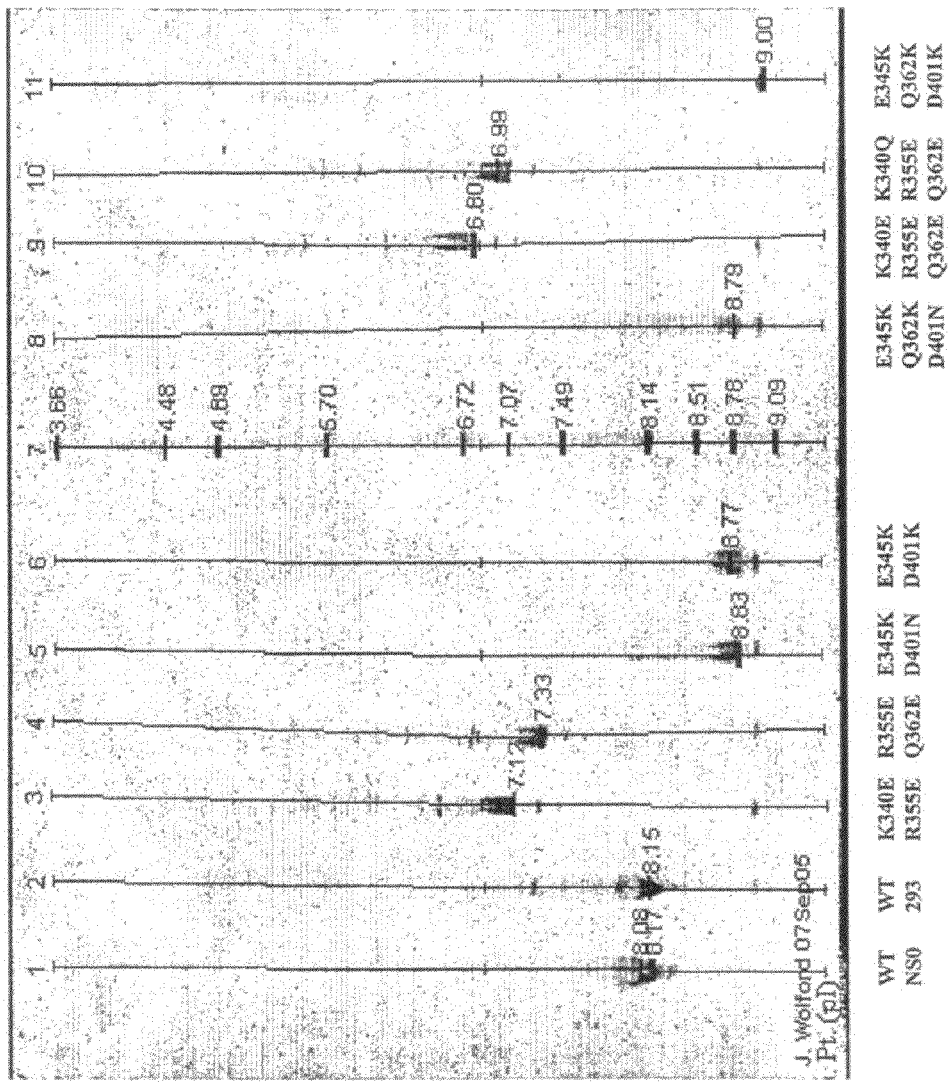

FIG. 27. IEF gel of the double and triple substitutions. The triple substitutions E345K Q362K D401N and E345K Q362K D401K probably have too high of a pI to be resolved on this gel and ran off. WT antibody produced both in 293H and NSO cells were run for comparison.

Figure 28:
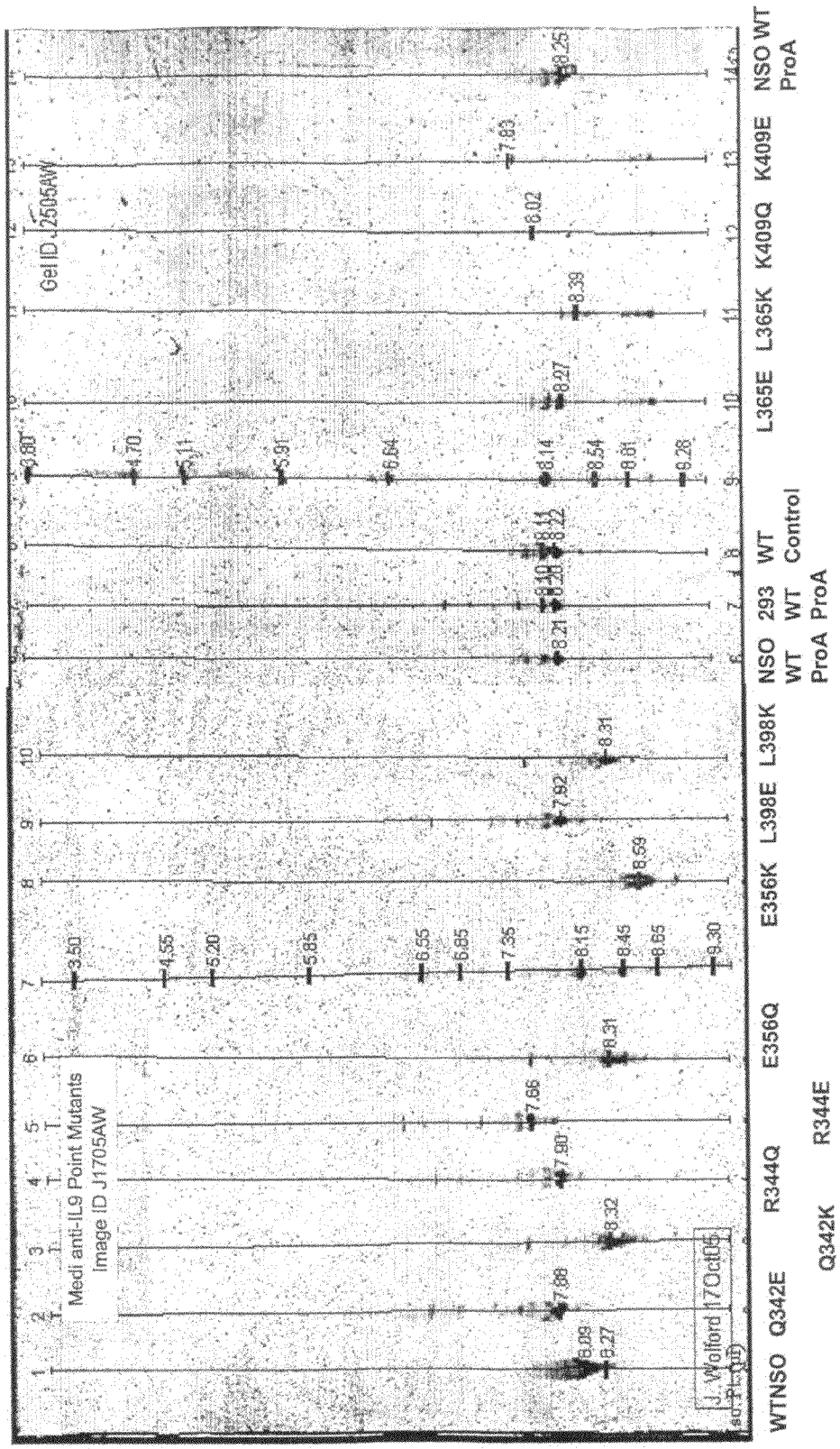

FIG. 28. IEF gel of the second 12 single substitutions made. The pI was determined by measuring the migration of the band with the highest intensity in a given lane. wild type (WT) antibody produced both in 293H and NSO cells were run for comparison.

Figure 29:
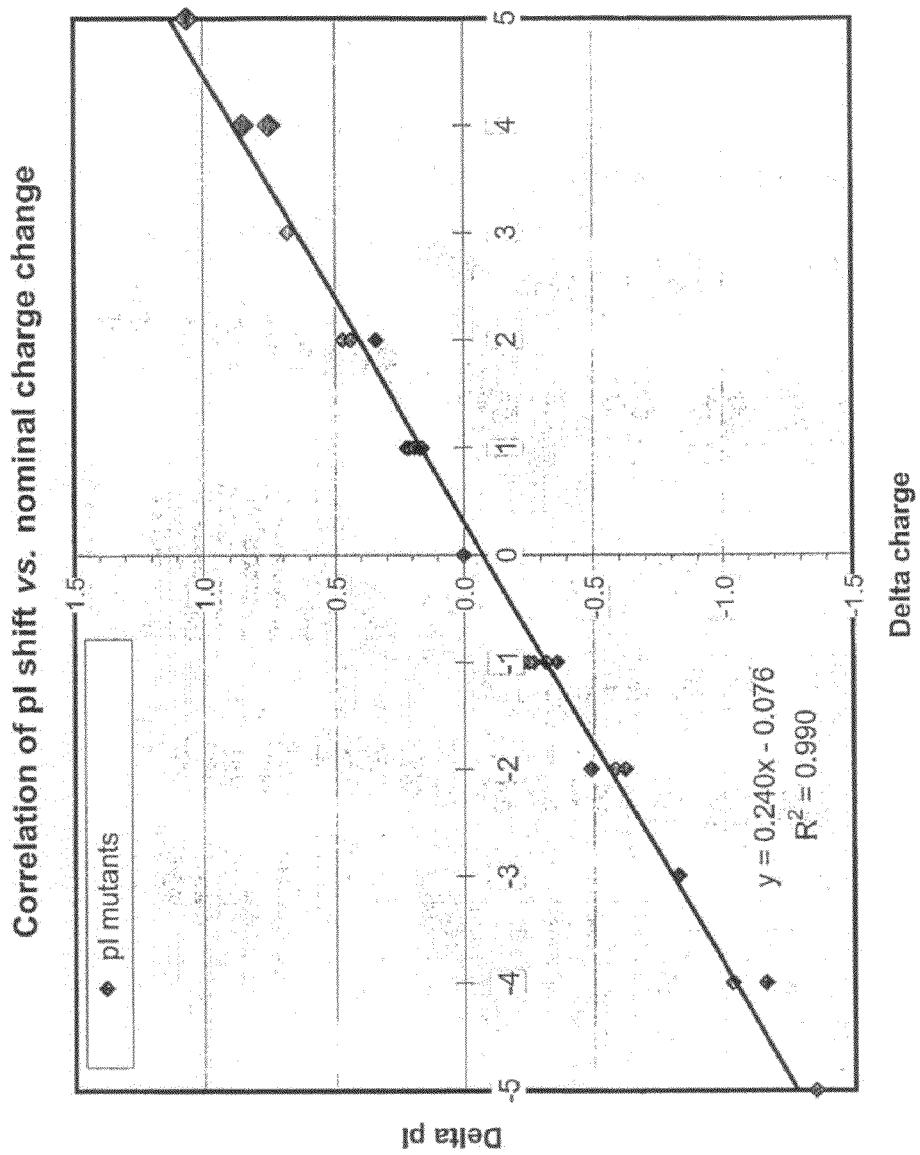

FIG. 29. Correlation of pI shift vs. nominal charge change. Plotted are the values for the delta change in pI vs. the delta change in the charge for each of the substituted antibodies. The correlation is largely linear.

Figure 30:
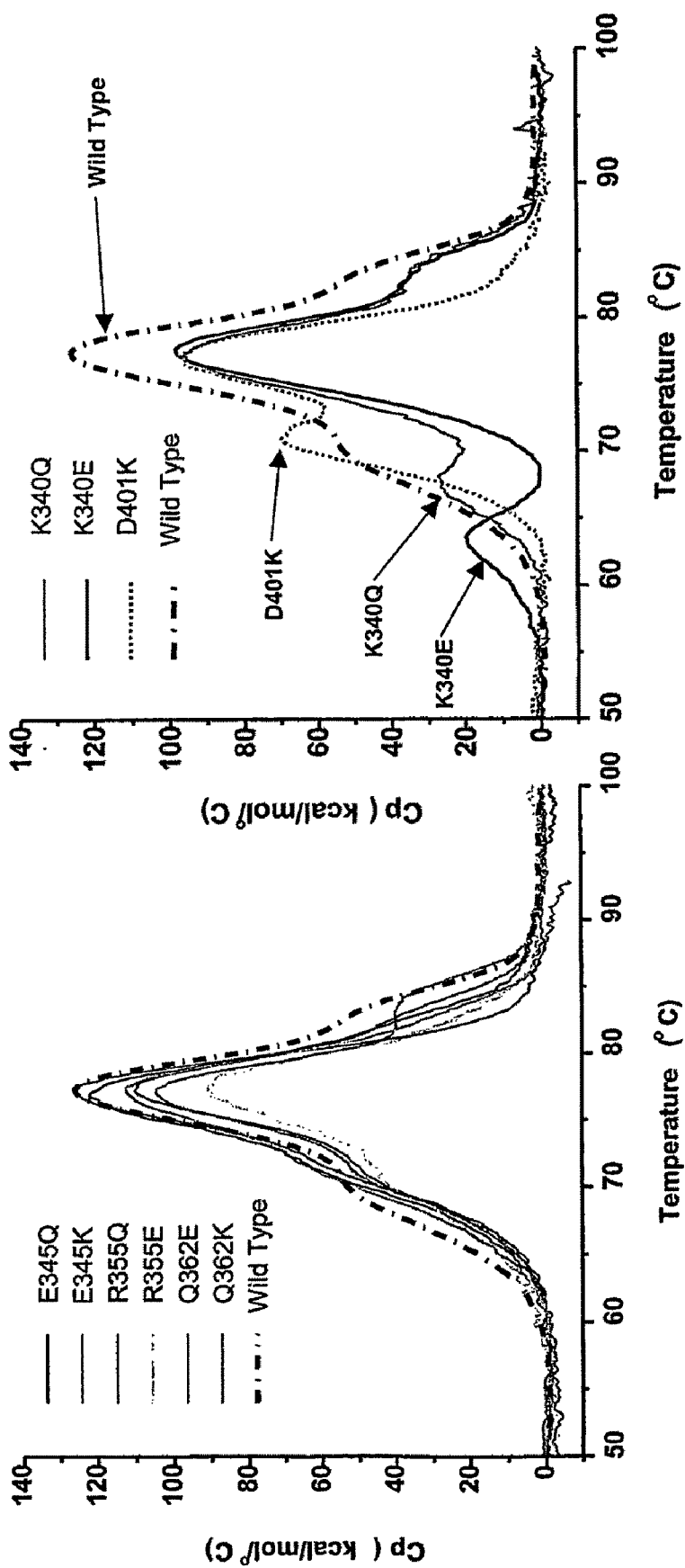

FIG. 30. Overlay of DSC thermograms of the wild type and single substituted anti-IL9 antibodies with altered pI. The Tm profiles of E345Q, E345K, R355Q, R355E, Q362E and Q362K (in the left panel) are very similar to that of the wild type antibody each having one major peak at ~76° C. The Tm profiles of K340Q, K340E and D401K have a distinct peak between about 62° C. and ~70° C. in addition to the major peak at ~76° C.

Figure 31:
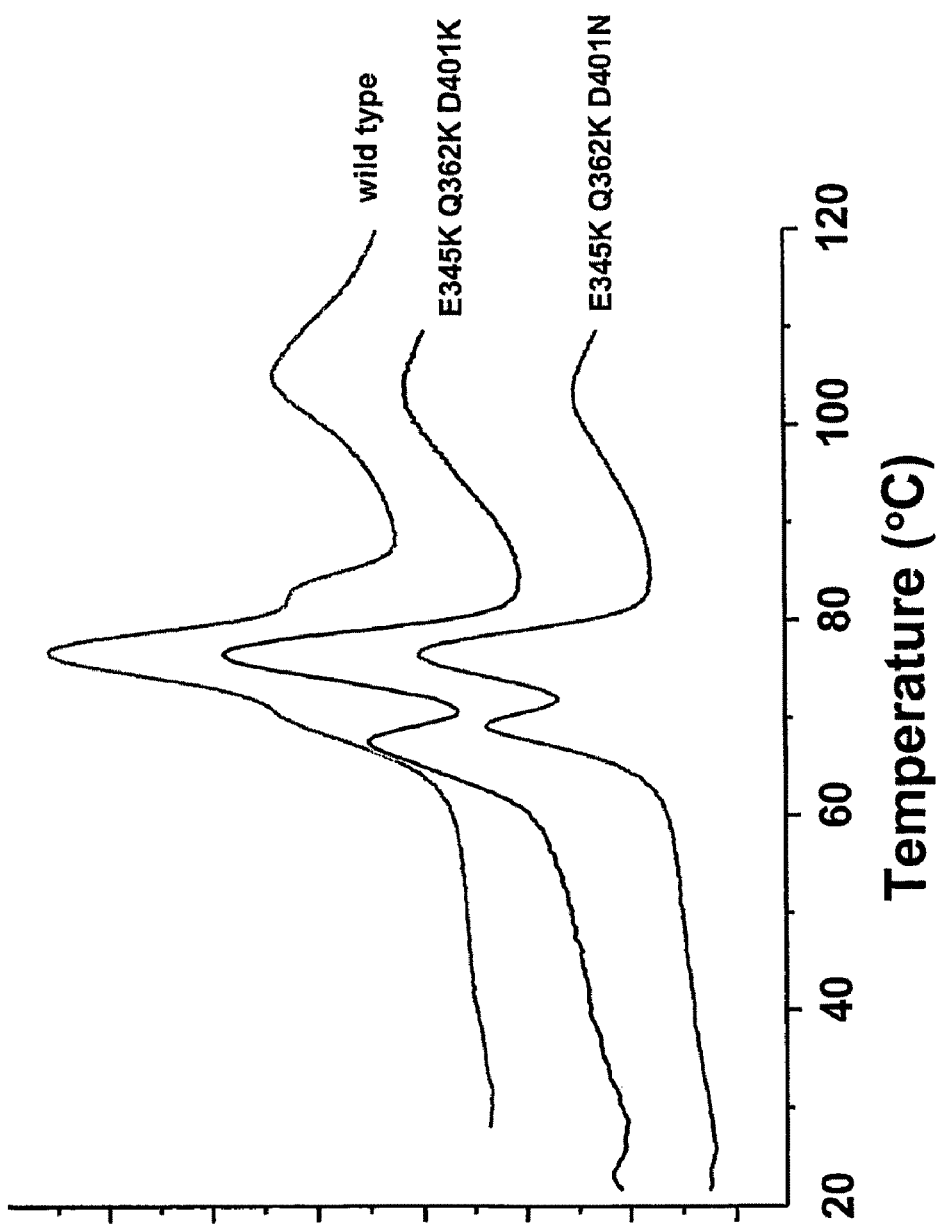

FIG. 31. Overlay of DSC thermograms of the wild type and triple substituted anti-IL9 antibodies with altered pI.

Figure 32:
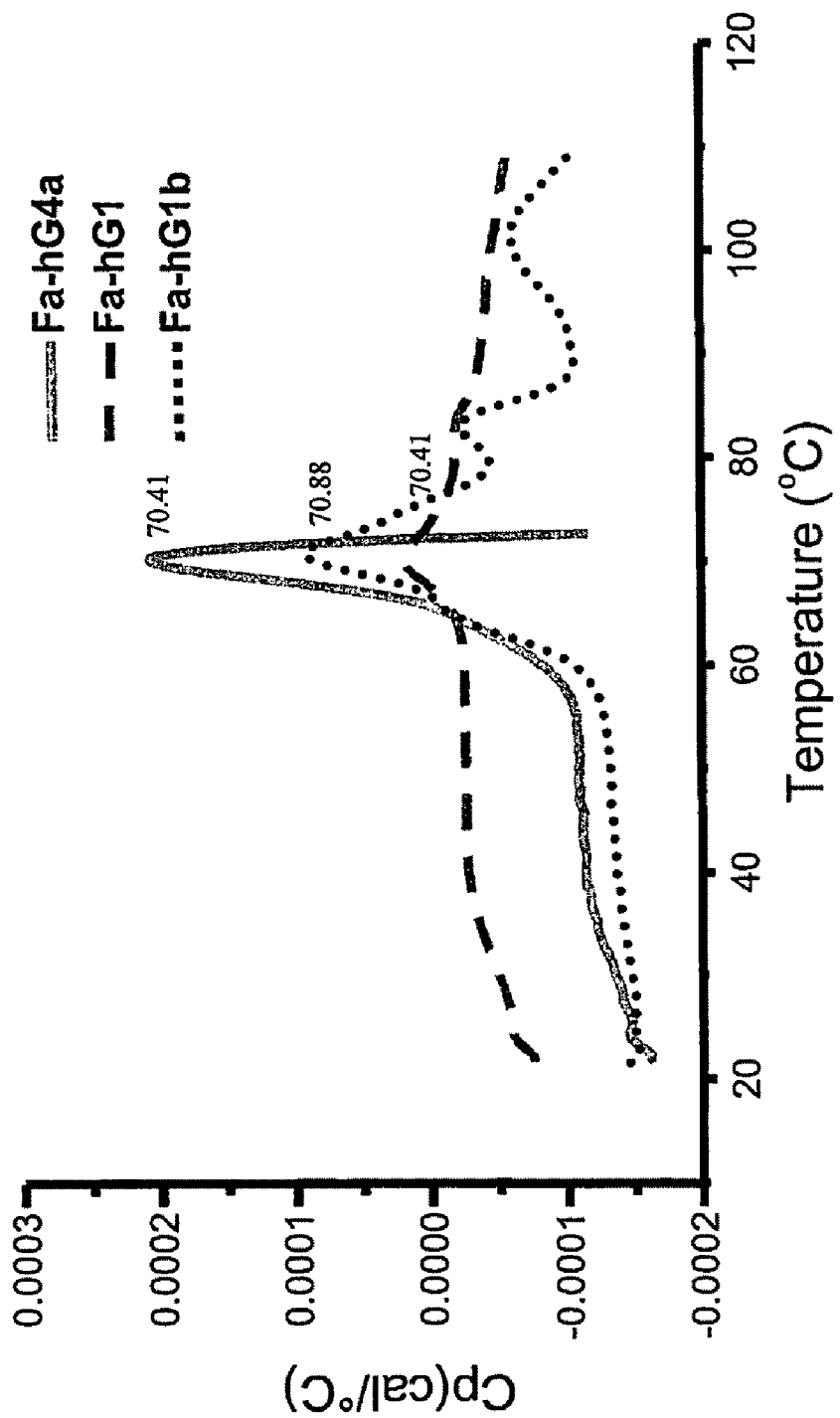

FIG. 32. Overlay of DSC thermograms of the wild type Fa-hG1 antibody and the two variants Fa-hG1b and Fa-hG4a. The major peak representing the Tm of the Fab domain is at 70.4° C. for both Fa-hG1 and Fa-hG4a and at 70.9° C. for Fa-hG1b.

Figure 33:
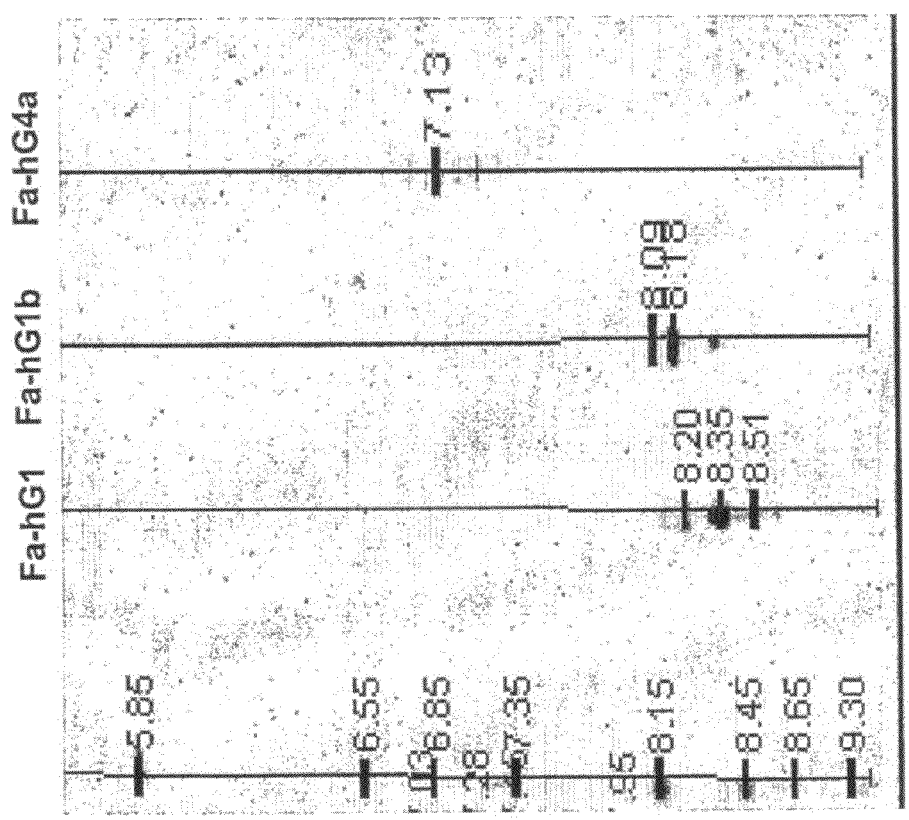

FIG. 33. IEF gel of the wild type Fa-hG1 antibody and the two variants Fa-hG1b and Fa-hG4a. The pI of the major protein bands are 8.35, 8.18 and 713 for Fa-hG1, Fa-hG1b and Fa-hG4a, respectively.

5. DETAILED DESCRIPTION OF THE INVENTION

The invention is based in part on the discovery of the inventors that certain therapeutic and/or formulation and/or manufacturing characteristics of a multidomain protein (e.g., antibody) can be evaluated by examining individual domains that form the protein. One or more metrics representing the physical and/or chemical and/or structural characteristics of protein domains are determined and individual domains are then selected based on their metrics. The individual domains may be examined in the context of the intact multidomain protein or as isolated domains. For example, the physical/chemical (including structural) characteristics of a Fab or an Fc domain in an antibody may determine the biodistribution and/or non-specific toxicity and/or stability and/or solubility and/or viscosity of the antibody. An approach incorporating selecting appropriate domains having optimal therapeutic and/or formulation characteristics prior to or concurrently with the generation of the full protein improves the overall drug development efficiency. This approach thus allows generation of proteins of both high therapeutic efficacy and optimal formulation characteristics, e.g., high solubility and long shelf life.

The invention provides an integrated approach to therapeutic protein development which incorporates therapeutic and/or formulation and/or manufacturing considerations in the early screening and development process. The approach involves evaluating one or more individual candidate domains of a protein to identify domains that have both the desired biological activity and desired therapeutic and/or formulation characteristics. For example, a plurality of different variants of a domain (also encompassed by the terms "domain variant(s)," "variant domain(s)" and "candidate domain(s)") that have been determined to have the desired biological activity can be screened to identify one or more variants that have certain desired therapeutic and/or formulation characteristics based on certain metrics (e.g., Tm and/or pI). The identified domain variants are then used in the construction of the full multidomain proteins. For example, in therapeutic antibody development, after affinity screening of an expression library (e.g., a phage display library), candidate Fab domains having high binding affinity can be screened for their formulation characteristics, e.g., solubility and/or stability. One or more Fab domains having desired formulation characteristics, e.g., having high solubility and/or stability, are selected and each used with an appropriate Fc domain in the construction of the full antibodies. Different candidate Fc domains can also be screened for formulation characteristics, e.g., solubility and stability, to select an Fc domain that has the desired formulation characteristics. The constructed antibodies are then submitted for further formulation development.

The invention further provides methods for the development of a therapeutic multidomain protein by engineering one or more domains of the multidomain protein to have the desired therapeutic and/or formulation characteristics such as for example, biodistribution, non-specific toxicity, solubility and/or stability. For example, a domain having a desired biological activity can be modified by replacing one or more amino acid residues in said domain to generated a modified domain (also encompassed by the terms "domain variant(s)," "variant domain(s)" and "candidate domain(s)") or a population of modified domains which are then screened for their therapeutic characteristics, e.g., biodistribution and/or non-specific toxicity by comparing certain metrics (e.g., Tm and/or pI) of the modified domains to those of the unmodified domain. One or more modified domains having desired therapeutic characteristics based on their metrics (e.g., having a desired Tm and/or pI) are selected and each used in the construction of the full multidomain protein.

The present invention also provides a method for evaluating the shelf life, i.e., the long term stability, of a protein preparation comprising a multidomain protein based on a thermal denaturation and/or renaturation behavior of a multidomain protein in a liquid protein preparation. It is contemplated that the multidomain protein may comprise a domain whose unfolding leads to aggregation of the multidomain protein in the liquid protein preparation. The liquid protein preparation can be a solution of the multidomain protein of a particular concentration, e.g., a concentration from about 5 to 300 mg/ml. The liquid protein preparation can also comprise other substances, including but not limited to, salts, ligands, co-factors, and so on. The method thus can also be used for determining the optimal conditions, e.g., the constituents and the optimal concentration of each such constituent.

The inventor has discovered that the aggregation of a multidomain protein in a solution is the result of thermal unfolding (also referred to herein as "thermal denaturation" or simply "denaturation") of a particular domain or domains in the protein, and that thermal denaturation and/or renaturation behavior of a multidomain protein comprising the particular domain or domains provides an indication of the long term stability and, thus, the shelf life, of a liquid formulation of the multidomain protein.

The pI of certain therapeutic multidomain proteins is known to affect their biodistribution and/or their non-specific toxicity profiles. The inventor has further discovered that the viscosity and solubility of a multidomain protein in a solution correlates with the pI of the multidomain protein and/or a particular domain or domains in the protein, relative to the pH of the solution. Thus, the pI of a multidomain protein and/or one or more individual domains provides an indication of viscosity and solubility of a liquid formulation of the multidomain protein in addition to other therapeutic characteristics. Additionally, the inventor has discovered that the pI of multidomain proteins can be modified to alter those characteristics which are governed by the pI of a protein.

5.1. Methods for Development of Multidomain Protein Therapeutics

The invention provides a method for protein drug development that incorporates therapeutic and/or formulation and/or manufacturing considerations in the early screening process. A protein drug is a formulated drug form of a therapeutic protein which can be used in the treatment or prevention of a disease. The formulation of the drug aids and/or optimizes the clinical effect of the protein, i.e., the pharmacological effect of the protein. The development of a therapeutic protein depends on the physical, chemical, and pharmacokinetic properties of the protein. The manufacturing process of a protein drug, including production, purification, storage, and any downstream processing of the protein, also depends on the physical and chemical properties of the protein.

As used herein, the "therapeutic characteristics" of a protein include physical, chemical, and pharmacokinetic properties of the protein which affect the pharmacological effect of the protein drug form. Examples of therapeutic characteristics of a protein include, but are not limited to, biodistribution, non-specific toxicity and clearance profiles of the protein.

As used herein, the formulation and/or manufacturing characteristics of a protein include physical, chemical, and pharmacokinetic properties of the protein which affect the pharmacological effect of the protein drug form and/or the production, purification, storage and any downstream processing of the protein. For simplicity reasons, the formulation and/or manufacturing characteristics of a protein are often referred to herein jointly as simply the "formulation characteristics." Examples of formulation characteristics of a protein include, but are not limited to, stability (e.g., thermal stability and/or storage stability, also termed shelf life), solubility and viscosity of the protein.

The invention provides a method for the generation of multidomain proteins having both high biological activities and optimal therapeutic and/or formulation and/or manufacturing characteristics. The method comprises evaluating the biological activities and the therapeutic and/or formulation and/or manufacturing characteristics of individual domains of a multidomain protein, and identifying domains that exhibit both desired biological activities, e.g., desired level of target binding affinity and/or desired serum half-life, etc., and desired therapeutic and/or formulation and/or manufacturing characteristics, e.g., desired level of solubility and/or stability. In certain embodiments, the therapeutic and/or formulation and/or manufacturing characteristics of individual domains of a multidomain protein are evaluated by metrics of the invention which include one or more parameters characterizing therapeutic and/or formulation characteristics including but not limited to stability, solubility, biodistribution and non-specific toxicity. In certain embodiments, individual domains that exhibits an optimal combination of biological activities and therapeutic and/or formulation and/or manufacturing characteristics are identified. In certain other embodiments, different domains which when combined in a protein exhibit an optimal combination of biological activities and therapeutic and/or formulation and/or manufacturing characteristics are identified. The identified domains are then used to construct the full protein.

In one embodiment, the method of generating one or more multidomain proteins for therapeutic uses, comprises (a) evaluating for each of a plurality of candidate domains one or more metrics representing one or more therapeutic and/or formulation and/or manufacturing characteristics of the first domain, wherein the plurality of candidate domains exhibits a biological activity above a predetermined threshold level; (b) selecting one or more domains from the plurality based on the metrics; and (c) optionally, constructing a full multidomain protein using each domain selected in step (b) and one or more other domains. In one embodiment, the metrics include one or more parameters characterizing stability of the candidate domain. In another embodiment, the metrics include one or more parameters characterizing solubility, biodistribution or non-specific toxicity of the candidate domain.

Thus, the present invention provides a method comprising screening a plurality of candidate domains to identify one or more domains that have both the desired biological activities, e.g., desired target binding affinity, and desired therapeutic and/or formulation characteristics, e.g., biodistribution, non-specific toxicity, stability, solubility and viscosity. Each of the candidate domains is also referred to as a variant of the domain. The method comprises evaluating the candidate domains for both their biological activities and their therapeutic and/or formulation properties. One or more candidate domains which exhibit an optimal combination of biological activities and therapeutic and/or formulation characteristics are selected for constructing the full multidomain proteins.

In one embodiment, the method of generating one or more multidomain proteins for therapeutic uses further comprises, before using the selected domain to construct a full multidomain protein (prior to said step (c)), the steps of (i) evaluating for each of a plurality of other candidate domains one or more metrics; and (ii) selecting a another domain from the plurality of other candidate domains based on the metrics. In one embodiment, the metrics include one or more parameters characterizing stability of the other candidate domain. In another embodiment, the metrics include one or more parameters characterizing solubility, biodistribution or non-specific toxicity of the other candidate domain.

The present invention also provides a method for screening a plurality of candidate domains to identify one or more domains that have both the desired biological activities, e.g., desired target binding affinity, and desired metrics representing their therapeutic and/or formulation characteristics. in the context of the full multidomain protein. Thus, the present invention provides a method to evaluate one or more domains of a multidomain protein in an intact multidomain protein. By screening a plurality of intact multidomain proteins for one or more candidate domains which exhibit an optimal combination of biological activities therapeutic and/or formulation characteristics, the need to construct the full multidomain protein is eliminated. In one embodiment, the method comprises screening a plurality of antigen binding domains that bind a given target antigen in the context of an intact full length antibody molecule, to identify one or more antigen binding domains that have desired therapeutic and/or formulation characteristics.

The present invention further provides a method to engineer a domain to improve one or more therapeutic and/or formulation characteristic. In one embodiment, specific modifications (e.g., amino acids substitutions, additions or deletions) are engineered into a domain to modify one or more desired therapeutic and/or formulation characteristics.

In one embodiment, the formulation characteristics of a candidate protein domain is evaluated by evaluating one or more metrics of the invention (also referred to herein as simply "metrics") characterizing the formulation characteristics of the candidate domain. In one embodiment, the metrics include one or more parameters characterizing the stability of a domain. In another embodiment, the metrics include one or more parameters characterizing the solubility, biodistribution or non-specific toxicity of a domain. In a specific embodiment, the one or more parameters characterizing stability of the domain include a Thermal melting temperature (Tm) value of the domain. The Tm of a candidate domain, e.g., a Fab domain, can be a good indicator of the thermal stability of a protein containing the domain and may further provide an indication of the shelf-life of a protein containing the domain. A lower Tm indicates more aggregation/less stability, whereas a higher Tm indicates less aggregation/more stability. Thus, candidate domains having higher Tm are preferable for incorporation into a full multidomain protein (e.g., an antibody). In one embodiment, candidate domains having a Tm greater than a predetermined threshold value are selected. In some embodiments, one or more candidate domains that have a Tm value higher than at least 50° C., 55° C., 60° C., 65° C., 70° C., 75° C., 80° C., 85° C., 90° C., 95° C., 100° C., 105° C., 110° C., 115° C. or 120° C. are selected for construction of the full multidomain protein. In specific embodiments, the candidate domains are antigen binding domains (e.g., Fab domain, scFv, etc.).

Thermal melting temperatures (Tm) of a protein domain can be measured using any standard method known in the art. For example, Vermeer et al. studied the unfolding and denaturation of a monoclonal mouse anti-rat IgG of isotype 2b by differential scanning calorimetry (DSC) and circular dichroism (CD) spectroscopy (Vermeer et al., 2000, Biophys. J. 78:394-404; Vermeer et al., 2000, Colloids Surfaces A: Physicochem. Eng. Aspects. 161:139-150; Vermeer et al., 2000, J. Colloid Interface Sci. 225:394-397; Vermeer et al., 2000, Biophys. J. 79:2150-2154). They showed that the folding/unfolding of the IgG can be characterized by two main transitions that are themselves superpositions of various steps. The bimodal distribution observed in both DSC and CD experiments did not depend on the scan rate in the experiments. The two transitions appeared to be independent, and the unfolding was irreversible. The IgG was then digested into isolated Fab and Fc fragments (Vermeer et al., 2000, Biophys. J. 79: 2150-2154). The secondary structure as well as the thermodynamic stability of the two isolated fragments were studied and compared with those of the intact immunoglobulin. It was shown that the two peaks observed for intact IgG can be assigned to the Fab and Fc fragments, respectively. Vermeer et al. also showed that, in addition to induction by heat, the structural perturbation of IgG in general could also be triggered by changing the pH (Vermeer et al., 2000, Biophys. J. 78:394-404) or by interaction with a hydrophobic environment, e.g., adsorption onto Teflon surfaces or interaction with surfactants (Vermeer et al., 1998, Biochim. Biophys. Acta. 1425:1-12; Vermeer et al., 2000, Colloids Surfaces A: Physicochem. Eng. Aspects. 161:139-150; Vermeer et al., 2000, J. Colloid Interface Sci. 225:394-397).

In one embodiment, the Tm of a protein domain is measured using a sample containing isolated protein domain molecules. In another embodiment, the Tm of a protein domain is measured using a sample containing an intact multidomain protein that contains the domain to be analyzed. In the latter case, the Tm of the domain is deduced from the data of the protein by analyzing only those data points corresponding to the domain of interest. In one embodiment, the Tm of a protein or protein domain is measured with a VP-DSC (MicroCal, LLC) using a scan rate of 1.0° C./min and a temperature range of 25-120° C. A filter period of 8 seconds is used along with a 5 minute pre-scan thermostating. In a specific example, samples are prepared by dialysis into 25 mM Histidine-HCl, pH 6 using Pierce dialysis cups (3.5 kD). Average Mab concentrations are 50 μg/mL as determined by A280. Melting temperatures are determined following manufacturer procedures using Origin software supplied with the system. Briefly, multiple baselines are run with buffer in both the sample and reference cell to establish thermal equilibrium. After the baseline is subtracted from the sample thermogram, the data are concentration normalized and fitted using the deconvolution function. In another embodiment, stability of the candidate domains are evaluated using a method described in Section 5.2. The one or more metrics may further include metrics characterizing stability of the domain under one or more different conditions selected from the group consisting of different pH values, different temperatures, different shear stresses, and different freeze/thaw cycles.

In another specific embodiment, the one or more parameters characterizing the solubility, biodistribution or non-specific toxicity of the domain includes an Isoelectric Point (pI) value of the domain. The pI of a protein is defined as the pH at which a polypeptide carries no net charge. It is known in the art that protein solubility is typically lowest when the pH of the solution is equal to the isoelectric point (pI) of the protein. It is thus possible to evaluate the solubility of a protein for a given pH, e.g., pH 6, based on its pI. The pI of a protein is also a good indicator of the viscosity of the protein in a liquid formulation. High pI indicates high solubility and low viscosity (especially important for high concentration formulations). In one embodiment, candidate domains having a pI greater than a predetermined threshold value are selected. As described above, the pI of a protein also plays a role in biodistribution and non-specific toxicity of multidomain proteins. For example, it is known in the art that reducing the pI of recombinant toxins results in lower non-specific toxicity and renal accumulation. Alternatively, increases the pI of antibodies is known to increase their intracellular and/or extravascular localization. One of skill in the art can readily determine which therapeutic characteristics are most desirable for a particular multidomain protein. In some embodiments, one or more candidate domains that have a pI value higher than about 5.0, 5.5, 6.0, 6.5, 7.0, 7.5, 8.0, 8.5, or 9.0 are selected for construction of the full multidomain protein. In other embodiments, one or more candidate domains that have a pI value less than about 9.0, 8.5, 8.0, 7.5, 7.0, 6.5, 6.0, 5.5, or 5.0 are selected for construction of the full multidomain protein. It will be understood by one skilled in the art that a single protein will have multiple charge forms. Without wishing to be bound by any particular theory, the charge of a protein can be modified by a number of different mechanisms including but not limited to, amino acid substitution, cationization, deamination, carboxyl-terminal amino acid heterogeneity, phosphorylation and glycosylation. As used herein the pI value is defined as the pI of the predominant charge form.

The pI of a protein may be determined by a variety of methods including but not limited to, isoelectric focusing and various computer algorithms (see for example Bjellqvist et al., 1993, *Electrophoresis* 14:1023). In one embodiment, pI is determined using a Pharmacia Biotech Multiphor 2 electrophoresis system with a multi temp 3 refrigerated bath recirculation unit and an EPS 3501 XL power supply. Pre-cast ampholine gels (Amersham Biosciences, pI range 2.5-10) are loaded with 5 μg of protein. Broad range pI marker standards (Amersham, pI range 3-10, 8 μL) are used to determine relative pI for the Mabs. Electrophoresis is performed at 1500 V, 50 mA for 105 minutes. The gel is fixed using a Sigma fixing solution (5×) diluted with purified water to 1×. Staining is performed overnight at room temperature using Simply Blue stain (Invitrogen). Destaining is carried out with a solution that consisted of 25% ethanol, 8% acetic acid and 67% purified water. Isoelectric points are determined using a Bio-Rad Densitometer relative to calibration curves of the standards. The one or more metrics may further include metrics characterizing stability of the domain under one or more different conditions selected from the group consisting of different pH values, different temperatures, different shear stresses, and different freeze/thaw cycles.

It will be understood by one skilled in the art that the evaluation of candidate domains may be performed on isolated domains or alternatively, each domain may be evaluated in the context of the intact multidomain protein. The latter approach is particularly useful when a plurality of multidomain proteins differ from each other in a single domain. It will be further understood, that an intact multidomain protein comprising a modified domain may be evaluated to determine the effect of a modified domain on one or more metrics of the invention representing one or more therapeutic and/or formulation and/or manufacturing characteristics. It will also be understood by one skilled in the art that the selected domains, whether evaluated as isolated domains or in the context of an intact multidomain protein, may be incorporated into multidomain proteins. For example, a Fab fragment evaluated and selected in the context of an intact antibody may be utilized in the generation of a chimeric protein comprising a toxin. As used herein, the term "evaluate candidate domains" and grammatical variations thereof, specifically encompass the evaluation of both isolated candidate domains and the evaluation of candidate domains in the context of an intact multidomain protein or fragment thereof.

Thus, the invention provides a method of screening a plurality of multidomain proteins to identify one or more multidomain proteins that have both the desired biological activities and the desired therapeutic and/or formulation characteristics comprising (a) evaluating for each of a plurality of different multidomain proteins one or more metrics representing one or more therapeutic and/or formulation and/or manufacturing characteristics of candidate domains of the multidomain proteins, wherein the plurality of different multidomain proteins exhibits a biological activity above a predetermined threshold level; and (b) selecting one or more multidomain proteins from the plurality based on the metrics of the candidate domains. In one embodiment, the method further comprises generating the population of different multidomain proteins. In certain embodiments, the multidomain protein is an antibody. In other embodiments the modified domain is an antigen binding domain. In still other embodiments, the modified domain is an Fc domain or fragment thereof.

The invention also provides a method for engineering a multidomain protein for preferred therapeutic and/or formulation properties. In one embodiment, the method comprises engineering one or more domains to improve the protein's formulation characteristics. In another embodiment, the method comprises engineering one or more domains to improve the multidomain protein's therapeutic characteristics. In still another embodiment, the method comprises engineering one or more domains to improve both the multidomain protein's therapeutic and formulation characteristics. In specific embodiments, the engineered domain exhibits improved therapeutic and/or formulation characteristics without reducing significantly the protein's pharmacological characteristics. In another specific embodiment, the engineered domain exhibits improved therapeutic and/or formulation characteristics without substantially affecting the protein's pharmacological characteristics. Accordingly, the invention also provides engineered multidomain proteins having preferred therapeutic and/or formulation properties. In certain embodiments, the engineered multidomain proteins having preferred therapeutic and/or formulation properties comprise a modified domain. In specific embodiment, the engineered multidomain proteins having preferred therapeutic and/or formulation properties comprise a modified antibody domain (e.g., antigen binding domain, Fc domain).

In a specific embodiment, the invention provides a method of engineering a multidomain protein to have improved stability. In certain embodiments, the multidomain protein comprises a domain which either has a low Tm or contributes to the multidomain protein having a low Tm. In one embodiment, a domain of a multidomain protein is modified by substituting one or more amino acid residues in the domain such that the stability of the domain is increased. In another embodiment, a domain is modified such that its Tm value is increased. The method comprises (a) modifying a domain of a multidomain protein by replacing one or more amino acid residues in the domain to generated a modified domain; (b) determining the Tm of the modified domain; and (c) classifying a multidomain protein containing the modified domain as having improved stability if the modified domain is determined to have a higher Tm in step (b). In some embodiments a domain is modified such that it has a Tm greater, than the Tm of the domain prior to modification. In certain embodiments, the Tm of the modified domain is increased by at least 2° C., at least 4° C., at least 6° C., at least 8° C., at least 10° C., at least 15° C., at least 20° C., at least 25° C., at least 30° C., or at least 40° C. In some embodiments, a domain is engineered such that it has a Tm greater than a predetermined threshold value. In certain embodiments, the predetermined Tm threshold value is at least 50° C., 55° C., 60° C., 65° C., 70° C., 75° C., 80° C., 85° C., 90° C., 95° C., 100° C., 105° C., 110° C., 115° C., or 120° C. In certain embodiments, the multidomain protein is an antibody. In other embodiments said modified domain is an antigen binding domain. In still other embodiments, said modified domain is an Fc domain or fragment thereof.

As described above, the Tm of a domain may be evaluated in an intact multidomain protein. Accordingly, the present invention provides method of engineering a multidomain protein to have improved stability in which the Tm of intact multidomain protein comprising a modified domain is determined. Optionally, or alternatively, the method of engineering a multidomain protein to have improved stability comprises (a) modifying the domain by replacing one or more amino acid residues in the domain to generated a modified domain; (b) determining the Tm of the multidomain protein containing the modified domain; and (c) classifying a multidomain protein containing the modified domain based on the Tm of the multidomain protein containing the modified domain determined in step (b).

The non-specific toxicity and/or biodistribution and/or solubility and/or viscosity of a protein may be optimized by altering the number and location of ionizable residues in the protein to adjust the pI. For example the pI of a polypeptide can be manipulated by making the appropriate amino acid substitutions. For example, at each amino acid residue of a protein, there are several possible changes that can be made: charged residues can be changed to uncharged residues or residues with the opposite charge and uncharged residues can be changed to residues with either a positive or negative charge. The maximum change in charge that can occur is where a charged amino acid is substituted with another amino acid of opposite charge (e.g., by substituting an aspartic acid for a lysine or arginine). Replacing a charged residue with an uncharged residue (e.g., by substituting a charged amino acid such as a lysine, for an uncharged residue such as alanine) serves will remove a charge but not add opposite charge and thus will result in a smaller pI change. The acidic amino acids aspartic acid (D) and glutamic acid (E) are deprotonated at or near physiological pH and carry a negative charge. The basic amino acids lysine (K) and arginine (R) are protonated at or near physiological pH and carry a positive charge. Substitutions of D and E with either K or R, or vice versa, are likely to have the greatest impact on pI. Specific amino acid substitutions are described below and detailed in Example 4.

Without wishing to be bound by any particular theory, amino acid substitutions of a protein that result in changes of the pI of said protein may improve non-specific toxicity and/or biodistribution and/or solubility and/or the viscosity of the protein. One skilled in the art would be able to determine amino acid substitutions that is most appropriate for a particular protein to achieve a desired pI. The pI of a protein may be determined by a variety of methods including but not limited to isoelectric focusing. It can also be estimated using any one of the various computer algorithms (see for example Bjellqvist et al., 1993, *Electrophoresis* 14:1023). In certain embodiments, the invention provides engineered multidomain proteins that have improved non-specific toxicity and/or biodistribution and/or solubility and/or lower viscosity. In a specific embodiment, the engineered multidomain proteins that have improved non-specific toxicity and/or biodistribution solubility and/or lower viscosity comprise a modified domain having different pI than the same domain prior to modification.

In a specific embodiment, the invention provides a method of engineering a multidomain protein to have improved solubility and/or lower viscosity. In certain embodiments, the multidomain protein comprises a domain which either has a low pI or contributes to the multidomain protein having a low pI. The method comprises (a) modifying a domain of the multidomain protein by replacing one or more amino acid residues in the domain to generated a modified domain; (b) determining the pI of the modified domain; and (c) classifying a multidomain protein containing the modified domain as having improved solubility and/or viscosity if the modified domain is determined to have a higher pI in step (b). In one embodiment a domain is engineered such that it has a pI greater than the pI of the domain prior to modification. In some specific embodiments, the pI of the modified domain is increased by at least 0.5, at least 1.0, at least 2.0, at least 3.0, at least 4.0, at least 5.0, or at least 10.0. In one embodiment, a domain is engineered such that it has a pI greater than a predetermined threshold value. In some specific embodiments, the predetermined pI threshold value is about 5.0, 5.5, 6.0, 6.5, 7.0, 7.5, 8.0, 8.5, or 9.0.

In certain embodiments, the invention provides engineered multidomain proteins that have improved solubility and/or lower viscosity. In a specific embodiment, the engineered multidomain proteins that have improved solubility and/or lower viscosity comprise a modified domain having a higher pI than the same domain prior to modification. In certain embodiments, the multidomain protein is an antibody. In other embodiments said modified domain is an antigen binding domain. In still other embodiments, said modified domain is an Fc domain or fragment thereof.

In other specific embodiments, the invention provides a method of engineering a multidomain protein to have reduced non-specific toxicity. In certain embodiments, the multidomain protein comprises a domain which either has a pI or contributes to the multidomain protein having a pI which results in non-specific toxicity. The method comprises (a) modifying a domain of a multidomain protein by replacing one or more amino acid residues in the domain to generated a modified domain; (b) determining the pI of the modified domain; and (c) classifying the multidomain protein containing the modified domain as having reduced non-specific toxicity if the modified domain is determined to have a lower pI in step (b). In one embodiment a domain is engineered such that it has a pI less than the pI of the domain prior to modification. In some specific embodiments, the pI of the modified domain is decreased by at least 0.5, at least 1.0, at least 2.0, at least 3.0, at least 4.0, at least 5.0, or at least 10.0. In one embodiment, a domain is engineered such that it has a pI less than a predetermined threshold value. In some specific embodiments, the predetermined pI threshold value is about 9.0, 8.5, 8.0, 7.5, 7.0, 6.5, 6.0, 5.5 or 5.0.

In certain embodiments, the invention provides engineered multidomain proteins that have reduced non-specific toxicity. In a specific embodiment, the engineered multidomain proteins that have reduced non-specific toxicity comprises a modified domain having a lower pI than the same domain prior to modification. In certain embodiments, the multidomain protein is an antibody. In other embodiments said modified domain is an antigen binding domain. In still other embodiments, said modified domain is an Fc domain or fragment thereof.

In additional embodiments, the invention provides a method of engineering a multidomain protein to have a specific biodistribution (e.g., intracellular, extravascular, extracellular). In certain embodiments, the multidomain protein comprises a domain which either has a pI or contributes to the multidomain protein having a pI which determines the biodistribution. The method comprises (a) modifying a domain of a multidomain protein by replacing one or more amino acid residues in the domain to generated a modified domain; (b) determining the pI of the modified domain; and (c) classifying a multidomain protein containing the modified domain as having reduced intracellular localization if the modified domain is determined to have a lower pI in step (b) or as having increased intracellular and/or extravascular localization if the modified domain is determined to have a higher pI in step (b). In one embodiment a domain is modified such that it has a pI greater than the pI of the domain prior to modification. In some specific embodiments, the pI of the modified domain is increased by at least 0.5, at least 1.0, at least 2.0, at least 3.0, at least 4.0, at least 5.0, or at least 10.0. In one embodiment, a domain is modified such that it has a pI greater than a predetermined threshold value. In another embodiment a domain is modified such that it has a pI less than the pI of the domain prior to modification. In some specific embodiments, the pI of the modified domain is decreased by at least 0.5, at least 1.0, at least 2.0, at least 3.0, at least 4.0, at least 5.0, or at least 10.0. In another embodiment, a domain is engineered such that it has a pI less than a predetermined threshold value. In some specific embodiments, the predetermined pI threshold value is about 9.0, 8.5, 8.0, 7.5, 7.0, 6.5, 6.0, 5.5 or 5.0.

In certain embodiments, the invention provides engineered multidomain proteins that have increased intracellular and/or extravascular localization. In a specific embodiment, the engineered multidomain proteins that have increased intracellular and/or extravascular localization comprise a modified domain having a higher pI than the same domain prior to modification. In other embodiments, the invention provides engineered multidomain proteins that have reduced intracellular localization. In a specific embodiment, the engineered multidomain proteins that have reduced intracellular localization comprise a modified domain having a lower pI than the same domain prior to modification. In certain embodiments, the multidomain protein is an antibody. In other embodiments said modified domain is an antigen binding domain. In still other embodiments, said modified domain is an Fc domain or fragment thereof.

As described above, the pI of a domain may be evaluated in an intact multidomain protein. Accordingly, the present invention provides methods of engineering a multidomain protein to have improved non-specific toxicity and/or biodistribution solubility and/or lower viscosity in which the pI of intact multidomain protein comprising a modified domain is determined. Optionally, or alternatively, the methods of engineering a multidomain protein to have improved non-specific toxicity and/or biodistribution solubility and/or lower viscosity described above comprise: (a) modifying a domain of a multidomain protein by replacing one or more amino acid residues in the domain to generated a modified domain; (b) determining the pI of the multidomain protein containing the modified domain; and (c) classifying a multidomain protein containing the modified domain based on the pI of the multidomain protein containing the modified domain determined in step (b).

In certain embodiments, the modified Fc domain comprises a replacement at one or more amino acid residues selected from the group consisting of K338, A339, K340, G341, Q342, R344, E345, R355, E356, E357, M358, T359, K360, N361, Q362, L365, T366, K370, N390, Y391, K392, T393, T394, V397, L398, D399, S400, D401, F405, K409, L410, D413 and K414 as numbered by the EU index as set forth in Kabat. In specific embodiments, the modified Fc domain comprises one or more amino acid replacements from the group consisting of K338 to any uncharged residue (e.g., Q but generally not P or C), K338D, K338E, A339D, A339E, A339K, A339R, K340 to any uncharged residue (e.g., Q but generally not P or C), K340D, K340E, G314D, G314E, G314K, G314R, Q342D, Q342E, Q342K, Q342R, R344 to any uncharged residue (e.g., Q but generally not P or C), R344D, R344E, E345 to any uncharged residue (e.g., Q but generally not P or C), E345K, E345R, R355 to any uncharged residue (e.g., Q but generally not P or C), R355D, R355E, E356 to any uncharged residue (e.g., Q but generally not P or C), E356K, E356R, E357 to any uncharged residue (e.g., Q but generally not P or C), E357K, E357R, M358D, M358E, M358K, M358R, T359D, T359E, T359K, T359R, K360 to any uncharged residue (e.g., Q but generally not P or C), K360D, K360E, N361D, N361E, N361K, N361R, Q362D, Q362E, Q362K, Q362R, L365D, L365E, L365K, L365R, T366D, T366E, T366K, T366R, K370 to any uncharged residue (e.g., Q but generally not P or C), K370D, K370E, N390D, N390E, N390K, N390R, Y391D, Y391E, Y391K, Y391R, K392 to any uncharged residue (e.g., Q but generally not P or C), K392D, K392E, T393D, T393E, T393K, T393R, T394D, T394E, T394K, T394R, V397D, V397E, V397K, V397R, L398D, L398E, L398K, L398R, D399 to any uncharged residue (e.g., Q but generally not P or C), D399K, D399R, S400D, S400E, S400K, S400R, D401 to any uncharged residue (e.g., Q but generally not P or C), D401K, D401R, F405D, F405E, F405K, F405R, K409 to any uncharged residue (e.g., Q but generally not P or C), K409D, K409E, L410D, L410E, L410K, L410R, D413 to any uncharged residue (e.g., Q but generally not P or C), D413K, D413R, K414 to any uncharged residue (e.g., Q but generally not P or C), K414D and K414E as numbered by the EU index as set forth in Kabat.

In certain embodiments, the engineered Fc domain with a higher pI comprises a replacement at one or more amino acid residues selected from the group consisting of A339, G341, Q342, E345, E356, E357, M358, T359, N361, Q362, L365, T366, N390, Y391, T393, T394, V397, L398, D399, S400, D401, F405, L410 and D413 as numbered by the EU index as set forth in Kabat. In specific embodiments, the engineered Fc domain with a higher pI comprises one or more amino acid replacements selected from the group consisting of A339K, A339R, G314K, G314R, Q342K, Q342R, E345 to any uncharged residue (e.g., Q but generally not P or C), E345K, E345R, E356 to any uncharged residue (e.g., Q but generally not P or C), E356K, E356R, E357 to any uncharged residue (e.g., Q but generally not P or C), E357K, E357R, M358K, M358R, T359K, T359R, N361K, N361R, Q362K, Q362R, L365K, L365R, T366K, T366R, N390K, N390R, Y391K, Y391R, T393K, T393R, T394K, T394R, V397K, V397R, L398K, L398R, D399 to any uncharged residue (e.g., Q but generally not P or C), D399K, D399R, S400K, S400R, D401 to any uncharged residue (e.g., Q but generally not P or C), D401K, D401R, F405K, F405R, L410K, L410R, D413 to any uncharged residue (e.g., Q but generally not P or C), D413K and D413R as numbered by the EU index as set forth in Kabat.

In certain embodiments, the engineered Fc domain with a lower pI comprises a replacement at one or more amino acid residues selected from the group consisting of K338, A339, K340, G341, Q342, R344, R355, M358, T359, K360, N361, Q362, L365, T366, K370, N390, Y391, K392, T393, T394, V397, L398, 5400, F405, K409, L410, and K414 as numbered by the EU index as set forth in Kabat. In specific embodiments, the engineered Fc domain with a lower pI comprises one or more amino acid replacements selected from the group consisting of K338 to any uncharged residue (e.g., Q but generally not P or C), K338D, K338E, A339D, A339E, K340 to any uncharged residue (e.g., Q but generally not P or C), K340D, K340E, G314D, G314E, Q342D, Q342E, R344 to any uncharged residue (e.g., Q but generally not P or C), R344D, R344E, R355 to any uncharged residue (e.g., Q but generally not P or C), R355D, R355E, M358D, M358E, T359D, T359E, K360 to any uncharged residue (e.g., Q but generally not P or C), K360D, K360E, N361D, N361E, Q362D, Q362E, L365D, L365E, T366D, K370 to any uncharged residue (e.g., Q but generally not P or C), K370D, K370E, N390D, N390E, Y391D, Y391E, K392 to any uncharged residue (e.g., Q but generally not P or C), K392D, K392E, T393D, T393E, T394D, T394E, V397D, V397E, L398D, L398E, S400D, S400E, F405D, F405E, K409 to any uncharged residue (e.g., Q but generally not P or C), K409D, K409E, L410D, L410E, K414 to any uncharged residue (e.g., Q but generally not P or C), K414D and K414E as numbered by the EU index as set forth in Kabat.

It is contemplated that evaluation of candidate domains is generally to be performed under substantially similar conditions. For example, each candidate domain, evaluated as an intact multidomain protein or as an isolated domain thereof, is preferably at a similar or identical concentration and is in a similar or identical buffer. Furthermore, all manipulations (e.g., pipetting, mixing, heating, cooling, etc.) are to be performed in a substantially similar manner for each candidate domain being evaluated whenever possible.

In another embodiment, candidate domains are further evaluated under one or more particular biochemical conditions, e.g., conditions under which the formulated drug is stored and/or used. For example, pH affects the shelf life of a protein. The composition of the solvent, e.g., water, also affects the shelf life of a protein. Glycerol alters the solvation properties of water to favor the native conformation of proteins. Ligands and cofactors in the solution may also affect the shelf life of a protein. Other biochemical parameters that have been shown to affect protein shelf life are: protein concentration, temperature, glutathione redox buffers (GSH, GSSG), the presence of detergents, and the presence of other additives, such as glycerol, arginine-HCl, polyethylene glycol (PEG), and organic solvents. Thus, the candidate domains can be evaluated under various conditions to gain more insights into the domains formulation characteristics, such pH dependence, ionic strength dependence, concentration of salts of the Hofmeister series, glycerol concentration, sucrose concentration, arginine concentration, dithiothreitol concentration, metal ion concentration, shear stress, and freeze/thaw stress, etc. For example, the stability of the candidate domains can be determined under a plurality of different biochemical conditions, either different levels of a particular type of conditions, such as different pH values, different temperatures, different sucrose concentrations, or a combination of different types and levels of conditions.

Some exemplary biochemical conditions described below are of particular interest. In some embodiments, the formulation may contain histidine with a concentration ranging from about 1 mM to about 100 mM, about 10 mM to about 50 mM, or about 20 mM to about 30 mM. Histidine can be in the form of L-histidine, D-histidine, or a mixture thereof, but L-histidine is the most preferable. Histidine can be also in the form of hydrates. Histidine may be used in a form of pharmaceutically acceptable salt, such as hydrochloride (e.g., monohydrochloride and dihydrochloride), hydrobromide, sulfate, acetate, etc. The purity of histidine should be at least 98%, or at least 99%, or at least 99.5%.

The pH of the formulation should not be equal to the isoelectric point of the particular multidomain protein (e.g., antibody) to be used in the formulation and may range from about 5.0 to about 7, or about 5.5 to about 6.5, or about 5.8 to about 6.2, and or about 6.0.

In addition to histidine and a multidomain protein (e.g., an antibody), the formulations may further comprise one or more amino acids (e.g., glycine) at a concentration of less than 100 mM, less than 50 mM, less than 3.0 mM, less than 2.0 mM, or less than 1.8 mM, and most preferably 1.6 mM. The amount of amino acid in the formulation should not cause a significant buffering effect so that protein precipitation at its isoelectric point can be avoided. An amino acid may be also used in a form of pharmaceutically acceptable salt, such as hydrochloride, hydrobromide, sulfate, acetate, etc. The purity of the amino acid should be at least 98%, or at least 99%, or 99.5%. In a specific embodiment, glycine is included in the formulations of the present invention.

Optionally, the formulations may further comprise other excipients, such as saccharides (e.g., sucrose, mannose, trehalose, etc.), polyols (e.g., Tween) and sugar alcohols (e.g., mannitol, sorbitol, etc.). In one embodiment, the other excipient is a saccharide. In a specific embodiment, the saccharide is sucrose, which is at a concentration ranging from between about 1% to about 20%, or about 5% to about 15%, or about 8% to 10%. In another embodiment, the other excipient is a polyol. Preferably, however, the formulations of the present invention do not contain mannitol. In a specific embodiment, the polyol is polysorbate (e.g., Tween 20), which is at a concentration ranging from between about 0.001% to about 1%, or about 0.01 to about 0.1.

In one embodiment, candidate domains are evaluated by one or more particular physical manipulations. For example candidate domains can be repeatedly subjected to shearing forces such as pumping, shaking, vortexing and the like to determine their ability to withstand shear stress such as those encountered during manufacture and shipping.

In a specific embodiment, the present invention provides a method for therapeutic antibody development. As used herein, the terms "antibody" and "antibodies" refer to monoclonal antibodies, multispecific antibodies, human antibodies, humanized antibodies, camelised antibodies, chimeric antibodies and anti-idiotypic (anti-Id) antibodies. The terms "antibody fragment" and "antibody domain" refer to any distinct region of antibody including but not limited to, "antigen binding domains" which bind an epitope, such as, Fab fragments, F(ab') fragments, Fv domains, Fd domain, "constant region domains" such as, CH1, hinge domain and Fc domains and any portions thereof, including for example, CH2 and CH3 domains. Single-chain Fvs (scFv), disulfide-linked Fvs (sdFv), and similar recombinantly generated antigen binding domains are also encompassed by the terms "antibody fragment" and "antibody domain". In particular, antibodies include immunoglobulin molecules and immunologically active fragments of immunoglobulin molecules, as well as antibody domain fusion proteins i.e., molecules that contain an antigen binding site or other antibody domain, fused to another protein domain including but not limited to non-immunoglobulin proteins, an Fc domain or fragment thereof. As outlined herein, the terms "antibody" and "antibodies" specifically include the Fc variants described herein, full length antibodies and variant Fc-Fusions comprising Fc domains, or fragments thereof, comprising at least one novel amino acid residue described herein fused to an immunologically active fragment of an immunoglobulin or to other proteins as described herein. Such variant Fc fusions include but are not limited to, scFv-Fc fusions, variable region (e.g., VL and VH)-Fc fusions, scFv-scFv-Fc fusions. Immunoglobulin molecules can be of any type (e.g., IgG, IgE, IgM, IgD, IgA and IgY), class (e.g., IgG1, IgG2, IgG3, IgG4, IgA1 and IgA2) or subclass.

The present invention also specifically encompasses antibodies with multiple specificities (e.g., an antibody with specificity for two or more discrete antigens (reviewed in Cao et al., 2003, *Adv Drug Deliv Rev* 55:171; Hudson et al., 2003, *Nat Med* 1:129)). For example, bispecific antibodies contain two different binding specificities fused together. In the simplest case a bispecific antibody would bind to two adjacent epitopes on a single target antigen, such an antibody would not cross-react with other antigens. Alternatively, bispecific antibodies can bind to two different antigens, such an antibody specifically binds to two different molecules such as a heterologous polypeptide or solid support material, but not to other unrelated molecules (e.g., BSA). See, e.g., PCT publications WO 93/17715; WO 92/08802; WO91/00360; WO 92/05793; Tutt, et al., J. Immunol. 147:60-69 (1991); U.S. Pat. Nos. 4,474,893; 4,714,681; 4,925,648; 5,573,920; 5,601, 819; Kostelny et al., J. Immunol. 148:1547-1553 (1992). While such molecules normally will only bind two antigens (i.e. bispecific antibodies), antibodies with additional specificities such as trispecific antibodies are encompassed by the instant invention. Accordingly, the multidomain proteins of the present invention may be antibodies that are monospecific, bispecific, trispecific or of greater multispecificity.

It will be understood that Fc domain as used herein includes the polypeptides comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM Fc may include the J chain. For IgG, the Fc domain comprises immunoglobulin domains Cgamma2 and Cgamma3 (C$\gamma$2 and C$\gamma$3) and the hinge between Cgamma1 (C$\gamma$1) and Cgamma2 (C$\gamma$2). Although the boundaries of the Fc domain may vary, the human IgG heavy chain Fc domain is usually defined to comprise residues C226 or P230 to its carboxyl-terminus, wherein the numbering is according to the EU index as in Kabat et al. (1991, NIH Publication 91-3242, National Technical Information Service, Springfield, Va.). The "EU index as set forth in Kabat" refers to the residue numbering of the human IgG1 EU antibody as described in Kabat et al. supra. Fc may refer to this domain in isolation, or this region in the context of an antibody, antibody fragment, or Fc fusion protein. An Fc containing protein may be an antibody, Fc fusion, or any protein or protein domain that comprises an Fc domain. The present invention also encompasses proteins comprising variant Fc domains, which are non naturally occurring variants of an Fc. Note: Polymorphisms have been observed at a number of Fc positions, including but not limited to Kabat 270, 272, 312, 315, 356, and 358, and thus slight differences between the presented sequence and sequences in the prior art may exist.

The method for therapeutic antibody development comprises screening a plurality of candidate antibody domains (e.g., Fab, Fc and Fv) that have high biological activity (e.g., binding affinity to a target antigen (e.g., antigen, Fc-receptor), effector function (e.g., ADCC, CDC)) for one or more metrics characterizing the therapeutic and/or formulation characteristics. In one embodiment, the metrics include one or more parameters characterizing stability of said antibody domain. In another embodiment, the metrics include one or more parameters characterizing solubility, biodistribution or non-specific toxicity of said antibody domain. In a specific embodiment, said one or more parameters characterizing stability of said antibody domain comprise a Tm value of said antibody domain, and said one or more parameters characterizing solubility, biodistribution or non-specific toxicity of said antibody domain comprise a pI value of said antibody domain.

The present invention also provides a method of generating one or more antibodies for therapeutic uses. In one embodiment, the method of generating one or more antibodies for therapeutic uses, comprises (a) evaluating for each of a plurality of candidate antibody domains one or more metrics representing one or more therapeutic and/or formulation and/or manufacturing characteristics of the antibody domain, wherein the plurality of candidate antibody domains exhibits a biological activity above a predetermined threshold level; (b) selecting one or more antibody domains from the plurality based on the metrics; and (c) optionally, constructing an antibody using each antibody domain selected in step (b) and one or more other domains.

In another embodiment, the method of generating one or more antibodies for therapeutic uses further comprises, before using the selected antibody domain to construct an antibody (prior to step (c)), the steps of (i) evaluating for each of a plurality of candidate other antibody domains one or more metrics; and (ii) selecting another antibody domain from the plurality of candidate other antibody domains based on the metrics.

In one embodiment, the plurality of candidate antibody domains can be an antigen binding domains (e.g., Fab domains). In such cases, the biological activity may be the antigen binding domain's binding affinity to a target antigen. In certain embodiments, at least some of the antigen binding domains bind different epitopes of the target antigen. In a specific embodiment, the plurality of antigen binding domains are obtained by screening an expression library (e.g., a phage display library) with the target antigen. In another specific embodiment, the plurality of antigen binding domains are obtained by digesting a plurality of monoclonal antibodies. Each selected antigen binding domain is then combined with another protein domain (e.g., Fc domain) to generate one or more multidomain proteins. In a specific embodiment, each selected antigen binding domain is combined with another antigen binding domain which may bind to the same or a different target antigen. In another specific embodiment, each selected antigen binding domain is combined with an antibody constant domain.

In another embodiment, the plurality of candidate antibody domains can be Fc domains. In such cases, the biological activity may be the Fc domain's binding affinity to constant region domain receptors an/or ligands (e.g., FcRn, C1q, FcγRs) and/or ability to mediate effector functions (e.g., ADCC, CDC). In a specific embodiment, the plurality of Fc domains are obtained by screening an expression library (e.g., a phage display library) with one or more of the constant region domain receptors an/or ligands. Each selected Fc is then combined with another protein domain (e.g., a Fab domain, a cellular receptor domain) to generate one or more multidomain proteins.

The methods described above for screening and/or engineering protein domains for their non-specific toxicity, biodistribution, solubility and thermal stability can be used. One or more antibody domains having reduced non-specific toxicity and/or desired biodistribution and/or high solubility and/or thermal stability are selected and used for constructing the full antibodies by combining them with the appropriate domain(s) to generate a full antibody. In one embodiment, one or more candidate antibody domains that have a Tm value higher than at least 50° C., 55° C., 60° C., 65° C., 70° C., 75° C., 80° C., 85° C., 90° C., 95° C., 100° C., 105° C., 110° C., 115° C., or 120° C. are selected for construction of the full antibody. In another embodiment, one or more candidate antibody domains that have a pI value higher than about 5.0, 5.5, 6.0, 6.5, 7.0, 7.5, 8.0, 8.5 or 9.0 are selected for construction of the full antibody domain containing multidomain protein. In another embodiment, one or more candidate antibody domains that have a pI value less than about 9.0, 8.5, 8.0, 7.5, 7.0, 6.5, 6.0, 5.5 or 5.0 are selected for construction of the full antibody domain containing multidomain protein.

In a specific embodiment, a plurality of antigen binding domains (e.g., Fab, scFv, etc.) that bind a given target antigen with an affinity above a chosen threshold level are obtained by affinity screening of an expression library (e.g., a phage display library). One or more metrics characterizing the antigen binding domains' therapeutic and/or formulation properties are then evaluated for each of the antigen binding domains. The plurality of antigen binding domains are ranked according to the one or more metrics. In one embodiment, the plurality of antigen binding domains are ranked according to their Tm values, and one or more antigen binding domains are selected from the top of the ranked list. In another embodiment, the plurality of antigen binding domains are ranked according to their pI values, and one or more antigen binding domains are selected from the top of the ranked list. In still another embodiment, the plurality of antigen binding domains are ranked according to a combined Tm and pI rank, and one or more antigen binding domains are selected from the top of the ranked list. The selected antigen binding domains are then used for construction of the full antigen binding domain containing multidomain proteins (e.g., antibodies, diabodies, etc.).

In another specific embodiment, a plurality of antibody constant region domains (e.g., Fc, CH2, CH3, etc) are evaluated for one or more metrics characterizing the constant region domains' therapeutic and/or formulation properties (e.g., solubility and thermal stability). The plurality of antigen binding domains are ranked according to the one or more metrics. In one embodiment, the plurality of constant region domains are ranked according to their Tm values, and one or more constant region domains are selected from the top of the ranked list. In another embodiment, the plurality of constant region domains are ranked according to their pI values, and one or more constant region domains are selected from the top of the ranked list. In still another embodiment, the plurality of constant region domains are ranked according to a combined Tm and pI rank, and one or more constant region domains are selected from the top of the ranked list. The selected constant region domains are then used for construction of the full antigen binding domain containing multidomain proteins (e.g., antibodies, diabodies, etc.). In certain embodiments, one or more candidate antibody constant region domains that have a Tm value higher than at least 50° C., 55° C., 60° C., 65° C., 70° C., 75° C., 80° C., 85° C., 90° C., 95° C., 100° C., 105° C., 110° C., 115° C., or 120° C. are selected for construction of the full antibody constant region domain containing multidomain protein (e.g., antibody). In other embodiments, one or more candidate antibody constant region domains that have a pI value higher than about 5.0, 5.5, 6.0, 6.5, 7.0, 7.5, 8.0, 8.5 or 9.0 are selected for construction of the full antibody constant region domain containing multidomain protein (e.g., antibody, Fc-fusion protein, etc.). In still other embodiments, one or more candidate antibody constant region domains that have a pI value lower than about 9.0, 8.5, 8.0, 7.5, 7.0, 6.5, 6.0, 5.5, or 5.0 are selected for construction of the full antibody constant region domain containing multidomain protein.

In a specific embodiment, the invention provides a method for engineering an antibody for preferred therapeutic and/or formulation properties. In one embodiment, the method comprises engineering the antigen binding (e.g., Fab) and/or constant region (e.g., Fc) domains to improve the protein's therapeutic and/or formulation characteristics. The method comprises making one or more modification (e.g., amino acid substitutions), the modifications are such that they improve one or more of the characteristics of said antibody.

In addition to binding antigen, antibodies are known to bind to a number of ligands via their constant region domain including, Fc receptors (e.g., FcRn, FcγRs) and the complement protein C1q. The binding interactions of the constant region domain are essential for a variety of effector functions and downstream signaling events such as antibody dependent cell-mediated cytotoxicity (ADCC) activity and complement dependent cytotoxicity (CDC). In certain embodiments, the engineered antibody exhibits improved therapeutic and/or formulation characteristics without reducing significantly the antibody's pharmacological characteristics, e.g., the antibody's binding specificity, binding affinity and/or avidity to its target, or the antibody's effector functions, e.g., Fc-receptor (FcR) and/or C1q binding, antibody dependent cellular cytotoxicity (ADCC), complement dependent cytotoxicity (CDC), and/or serum half life. In another embodiment, the engineered antibody exhibits improved therapeutic and/or formulation characteristics and improved pharmacological characteristics, e.g., the antibody's binding specificity, binding affinity and/or avidity to its target, or the antibody's Fc effector functions, e.g., FcR binding, ADCC, CDC, and/or serum half life.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enables these cytotoxic effector cells to bind specifically to an antigen-bearing target cell and subsequently kill the target cell with cytotoxins. Specific high-affinity IgG antibodies directed to the surface of target cells "arm" the cytotoxic cells and are absolutely required for such killing. Lysis of the target cell is extracellular, requires direct cell-to-cell contact, and does not involve complement. It is contemplated that, in addition to antibodies, other proteins comprising Fc domain, specifically Fc fusion proteins, having the capacity to bind specifically to an antigen-bearing target cell will be able to effect cell-mediated cytotoxicity. For simplicity, the cell-mediated cytotoxicity resulting from the activity of an Fc fusion protein is also referred to herein as ADCC activity.

The ability of any particular protein comprising an Fc to mediate lysis of the target cell by ADCC can be assayed. To assess ADCC activity a protein comprising an Fc is added to target cells in combination with immune effector cells, which may be activated by the antigen antibody complexes resulting in cytolysis of the target cell. Cytolysis is generally detected by the release of label (e.g. radioactive substrates, fluorescent dyes or natural intracellular proteins) from the lysed cells. Useful effector cells for such assays include peripheral blood mononuclear cells (PBMC) and Natural Killer (NK) cells. Specific examples of in vitro ADCC assays are described in Wisecarver et al., 1985 79:277-282; Bruggemann et al., 1987, *J Exp Med* 166:1351-1361; Wilkinson et al., 2001, *J Immunol Methods* 258:183-191; Patel et al., 1995 *J Immunol Methods* 184:29-38 and herein (see Example 3). Alternatively, or additionally, ADCC activity of the protein comprising an Fc may be assessed in vivo, e.g., in an animal model such as that disclosed in Clynes et al., 1998, PNAS USA 95:652-656.

"Complement dependent cytotoxicity" and "CDC" refer to the lysing of a target cell in the presence of complement. The complement activation pathway is initiated by the binding of the first component of the complement system (C1q) to a molecule, an antibody for example, complexed with a cognate antigen. To assess complement activation, a CDC assay, e.g. as described in Gazzano-Santoro et al., 1996, *J. Immunol. Methods,* 202:163, may be performed.

In one embodiment, the pI of an engineered antibody binding domain is between pH 5.0 and pH 10.0. In one embodiment, substitutions resulting in alterations in the pI of the antigen binding domain will not significantly diminish its binding affinity for an antigen. In one embodiment, the pI of an engineered antibody constant region domain is between pH 5.0 and pH 10.0. In still another embodiment, substitutions resulting in alterations in the pI of the constant region domain will not significantly diminish its effector binding and/or function. It is also contemplated that substitutions resulting in alterations in the pI in an antibody domain may be selected such that both the pI and other pharmacological characteristics of the antibody domain, e.g., the antibody's binding specificity, binding affinity and/or avidity to its target, or the antibody's Fc effector functions are improved. The inventors have found that certain modifications of the hinge region do not change the pI and Tm of the antibody significantly. Thus, in one embodiment, the invention provides a method for engineering an antibody to improve the antibody's biological activity without reducing the antibody's therapeutic and/or formulation properties.

In one embodiment, the modifications of an antibody domain as described herein may be combined with known modifications of the Fc domain such as those disclosed in Duncan et al, 1988, *Nature* 332:563-564; Lund et al., 1991, *J. Immunol* 147:2657-2662; Lund et al, 1992, *Mol Immunol* 29:53-59; Alegre et al, 1994, *Transplantation* 57:1537-1543; Hutchins et al., 1995, *Proc Natl. Acad Sci USA* 92:11980-11984; Jefferis et al, 1995, *Immunol Lett.* 44:111-117; Lund et at, 1995, *Faseb J* 9:115-119; Jefferis et al, 1996, *Immunol Lett* 54:101-104; Lund et al, 1996, *Immunol* 157:4963-4969; Armour et al., 1999, *Eur J Immunol* 29:2613-2624; Idusogie et al, 2000, *J Immunol* 164:4178-4184; Reddy et al, 2000, *J Immunol* 164:1925-1933; Xu et al., 2000, *Cell Immunol* 200:16-26; Idusogie et al, 2001, *J Immunol* 166:2571-2575; Shields et al., 2001, *J Biol Chem* 276:6591-6604; Jefferis et al, 2002, *Immunol Lett* 82:57-65; Presta et al., 2002, *Biochem Soc Trans* 30:487-490); U.S. Pat. Nos. 5,624,821; 5,885,573; 5,677,425; 6,165,745; 6,277,375; 5,869,046; 6,121,022; 5,624,821; 5,648,260; 6,528,624; 6,194,551; 6,737,056; 6,821,505; 6,277,375; U.S. Patent Publication No. 2004/0002587; PCT Publication Nos. WO 00/42072 and WO 99/58572; WO 94/29351; WO 02/060919; WO 04/029207; WO 04/099249; WO 04/063351. Also encompassed by the present invention are Fc domains which comprise deletions, additions and/or modifications. Still other modifications/substitutions/additions/deletions of the Fc domain will be readily apparent to one skilled in the art.

In one embodiment, the antibodies may be engineered to include modifications in the Fc domain, typically to alter one or more functional properties of the antibody, such as serum half-life, complement fixation, Fc receptor binding, and/or antigen-dependent cellular cytotoxicity, without reducing the antibodies' pI and Tm. Furthermore, an antibody may be chemically modified (e.g., one or more chemical moieties can be attached to the antibody) or be modified to alter its glycosylation, again to alter one or more functional properties of the antibody.

In one embodiment, the amino acid sequence of the Fc domain is modified by deleting, adding and/or substituting at least amino acid residue to alter one or more of the functional properties of the antibody described above. This approach is described further in Duncan et al, 1988, *Nature* 332:563-564; Lund et al., 1991, *J. Immunol* 147:2657-2662; Lund et al, 1992, *Mol Immunol* 29:53-59; Alegre et al, 1994, *Transplan-* tation 57:1537-1543; Hutchins et al., 1995, *Proc Natl. Acad Sci USA* 92:11980-11984; Jefferis et al, 1995, *Immunol Lett.* 44:111-117; Lund et al., 1995, *Faseb J* 9:115-119; Jefferis et al, 1996, *Immunol Lett* 54:101-104; Lund et al, 1996, *J Immunol* 157:4963-4969; Armour et al., 1999, *Eur J Immunol* 29:2613-2624; Idusogie et al, 2000, *J Immunol* 164:4178-4184; Reddy et al, 2000, *J Immunol* 164:1925-1933; Xu et al., 2000, *Cell Immunol* 200:16-26; Idusogie et al, 2001, *J Immunol* 166:2571-2575; Shields et al., 2001, *J Biol Chem* 276: 6591-6604; Jefferis et al, 2002, *Immunol Lett* 82:57-65; Presta et al., 2002, *Biochem Soc Trans* 30:487-490); U.S. Pat. Nos. 5,624,821; 5,885,573; 5,677,425; 6,165,745; 6,277,375; 5,869,046; 6,121,022; 5,624,821; 5,648,260; 6,194,551; 6,737,056 U.S. patent application Ser. No. 10/370,749 and PCT Publications WO 94/2935; WO 99/58572; WO 00/42072; WO 04/029207.

In still another embodiment, the glycosylation of antibodies is modified. For example, an aglycoslated antibody can be made (i.e., the antibody lacks glycosylation). Glycosylation can be altered to, for example, increase the affinity of the antibody for a target antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861.

Additionally or alternatively, an antibody can be made that has an altered type of glycosylation, such as a hypofucosylated antibody having reduced amounts of fucosyl residues or an antibody having increased bisecting GlcNAc structures. Such altered glycosylation patterns have been demonstrated to increase the ADCC ability of antibodies. Such carbohydrate modifications can be engineered by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. See, for example, Shields, R. L. et al. (2002) *J. Biol. Chem.* 277: 26733-26740; Umana et al. (1999) *Nat. Biotech.* 17:176-1, as well as, European Patent No: EP 1,176,195; PCT Publications WO 03/035835; WO 99/54342. Additional, methods for generating engineered glycoforms are known in the art, and include but are not limited to those described in Davies et al., 20017 *Biotechnol Bioeng* 74:288-294; Shields et al, 2002, *J Biol Chem* 277:26733-26740; Shinkawa et al., 2003, *J Biol Chem* 278:3466-3473) U.S. Pat. No. 6,602,684; U.S. Ser. No. 10/277,370; U.S. Ser. No. 10/113,929; PCT WO 00/61739A1; PCT WO 01/292246A1; PCT WO 02/311140A1; PCT WO 02/30954A1; Potillegent™ technology (Biowa, Inc. Princeton, N.J.); GlycoMAb™ glycosylation engineering technology (GLYCART biotechnology AG, Zurich, Switzerland). See, e.g., WO 00061739; EA01229125; US 20030115614; Okazaki et al., 2004, *JMB,* 336: 1239-49.

In another embodiment, the antibodies may be engineered to include modifications in the antigen binding domain to alter the therapeutic and/or formulation characteristics of the antibody, without reducing the binding characteristics of the antibody for its antigen. The method comprises making one or more modification (e.g., amino acid substitutions), said modifications are such that they improve said one or more of the therapeutic and/or formulation characteristics of said antibody. One skilled in the art will understand that amino acid substitutions and other modifications of an antibody may alter its binding characteristics (examples of binding characteristics include but are not limited to, binding specificity, equilibrium dissociation constant ($K_D$), dissociation and association rates ($K_{off}$ and $K_{on}$ respectively), binding affinity and/or avidity) and that certain alterations are more or less desirable. For example a modification that preserves or enhances antigen binding would generally be more preferable then one that diminished or altered antigen binding. It will be further understood, that antibodies may be engineered to include modifications in the constant region domain to alter the therapeutic and/or formulation characteristics of the antibody, without reducing the binding characteristics of the constant region to its receptors or ligands (e.g., FcRs, C1q). The binding characteristics of an antibody for a target antigen or constant region domain ligand may be determined by a variety of methods including but not limited it, equilibrium methods (e.g., enzyme-linked immunoabsorbent assay (ELISA) or radioimmunoassay (RIA)), or kinetics (e.g., BIACORE® analysis; see Example 2), for example. Other commonly used methods to examine the binding characteristics of antibodies are described in *Using Antibodies: A Laboratory Manual,* Cold Spring Harbor Laboratory Press, NY, Harrow et al., 1999 and *Antibodies: A Laboratory Manual,* Cold Spring Harbor Laboratory Press, NY; Harlow et al., 1989.

It is well known in the art that the affinity constant ($K_a$) is defined as $k_{on}/k_{off}$ and that the equilibrium dissociation constant ($K_D$) is defined as $k_{off}/k_{on}$. It is generally understood that an antibody with a high $K_a$ is preferable to an antibody with a low $K_a$ and that an antibody with a low $K_D$ is preferable to an antibody with a high $K_D$. However, in some instances the value of the $k_{on}$ or $k_{off}$ may be more relevant than the value of the $K_D$. One skilled in the art can determine which kinetic parameter is most important for a given antigen binding domain and application. In one embodiment, the methods of the invention will result in modified antigen binding and/or constant region domains with improved therapeutic and/or formulation characteristics and one or more binding characteristics (e.g., binding specificity, $K_D$, $K_{off}$, $K_{on}$, binding affinity and/or avidity) that are improved by at least 2%, or by at least 5%, or by at least 10%, or by at least 20%, or by at least 30%, or by at least 40%, or by at least 50%, or by at least 60%, or by at least 70%, or by at least 80% when compared to kinetic parameters of the antigen binding and/or constant region domain without said modification.

In another embodiment, the methods of the invention will result in modified antigen binding and/or constant region domains that have improved therapeutic and/or formulation characteristics, but do not have substantially diminished binding characteristics. For example, the methods of the invention will generate antigen binding and/or constant region domains that exhibit improved formulation characteristics, but preferably have no reduction in any binding characteristic (e.g., binding specificity, $K_D$, $K_{off}$, $K_{on}$, binding affinity and/or avidity), or have one or more antigen binding characteristics that are reduced by less than 1%, or by less than 5%, or by less than 10%, or by less than 20%, or by less than 30%, or by less than 40%, or by less than 50%, or by less than 60%, or by less than 70%, or by less than 80% when compared to antigen binding of the antibody without said substitution.

In yet another embodiment, the methods of the invention will result in the selection of antigen binding and/or constant region domains with a binding activity above a predetermined threshold having improved therapeutic and/or formulation characteristics. In certain embodiments, the binding activity is the affinity constant or $K_a$ ($k_{on}/k_{off}$) of the domain for a particular target/ligand/receptor. In a specific embodiment, the $K_a$ is at least $10^2 M^{-1}$, at least $5 \times 10^2 M^{-1}$, at least $10^3 M^{-1}$, at least $5 \times 10^3 M^{-1}$, at least $10^4 M^{-1}$, at least $5 \times 10^4 M^{-1}$, at least $10^5 M^{-1}$, at least $5 \times 10^5 M^{-1}$, at least $10^6 M^{-1}$, at least $5 \times 10^6 M^{-1}$, at least $10^7 M^{-1}$, at least $5 \times 10^7 M^{-1}$, at least $10^8 M^{-1}$, at least $5 \times 10^8 M^{-1}$, at least $10^9 M^{-1}$, at least $5 \times 10^9 M^{-1}$, at least $10^{10} M^{-1}$, at least $5 \times 10^1 M^{-1}$, at least $10^{11} M^{-1}$, at least $5 \times 10^{11} M^{-1}$, at least $10^{12} M^{-1}$, at least $5 \times 10^{12} M$, at least $10^{13} M^{-1}$, at least $5 \times 10^{13} M^{-1}$, at least $10^{14} M^{-1}$, at least $5 \times 10^{14} M^{-1}$, at least $10^{15} M^{-1}$, or at least $5 \times 10^{15} M^{-1}$. In other embodiments, the binding activity is the equilibrium dissociation constant ($K_D$) of the domain for a particular target/ligand/receptor. As described above, one of skill in the art will recognize that a molecule having a higher binding affinity will generally have a lower $K_D$ value. Accordingly, in a specific embodiment the $K_D$ is less than $10^{-5}$ M, or less than $10^{-6}$ M, or less than $10^{-7}$ M, or less than $10^{-8}$ M, or less than $10^{-9}$ M, or less than $10^{-10}$ M, or less than $10^{-11}$ M, or less than $10^{-12}$ M, or less than $10^{-13}$ M.

In one embodiment, selected or engineered antigen binding and/or constant region domains are then used to construct a full antigen binding and/or antibody constant domain containing multidomain protein (e.g., antibody) using methods known in the art. Such multidomain proteins can then be submitted to formulation development to determine the optimal formulations.

There are various methods available for assessing the stability of protein drug formulations (e.g., multidomain protein formulations), based on the physical and chemical structures of the proteins (e.g., antibodies or fragments thereof) as well as on their biological activities. For example, to study denaturation of proteins, methods such as charge-transfer absorption, thermal analysis, fluorescence spectroscopy, circular dichroism, NMR, and HPSEC, are available. See, for example, Wang et al., 1988, J. of Parenteral Science & Technology 42 (Suppl):S4-S26.

The rCGE and HPSEC are the most common and simplest methods to assess the formation of protein aggregates, protein degradation, and protein fragmentation. Accordingly, the stability of the formulations may be assessed by these methods.

In certain embodiments, the concentration of the multidomain protein formulations is at least 15 mg/ml, at least 20 mg/ml, at least 25 mg/ml, at least 30 mg/ml, at least 35 mg/ml, at least 40 mg/ml, at least 45 mg/ml, at least 50 mg/ml, at least 55 mg/ml, at least 60 mg/ml, at least 65 mg/ml, at least 70 mg/ml, at least 75 mg/ml, at least 80 mg/ml, at least 85 mg/ml, at least 90 mg/ml, at least 95 mg/ml, at least 100 mg/ml, at least 105 mg/ml, at least 110 mg/ml, at least 115 mg/ml, at least 120 mg/ml, at least 125 mg/ml, at least 130 mg/ml, at least 135 mg/ml, at least 140 mg/ml, at least 150 mg/ml, at least 200 mg/ml, at least 250 mg/ml, or at least 300 mg/ml.

In certain embodiments, the formulations of the multidomain protein exhibit stability at the temperature ranges of 38° C.-42° C. for at least 30 days, at least 45 days, or at least 60 days and, in some embodiments, not more than 120 days, of 20° C.-24° C. for at least 6 months, or at least 1 year, of 2° C.-8° C. (in particular, at 4° C.) for at least 6 months, at least 1 year, at least 2 years, at least 3 years, at least 4 years, or at least 5 years and at −20° C. for at least 1 year, at least 2 years, at least 3 years, at least 4 years, or at least 5 years, as assessed by high performance size exclusion chromatography (HPSEC). Namely, the formulations have low to undetectable levels of aggregation and/or fragmentation, as defined herein, after the storage for the defined periods as set forth above. Preferably, no more than 5%, no more than 4%, no more than 3%, no more than 2%, no more than 1%, no more than 0.5% of the protein or protein fragment forms an aggregate as measured by HPSEC, after the storage for the defined periods as set forth above. In specific embodiments, formulations of the multidomain protein exhibit almost no loss in biological activities of the multidomain protein during the prolonged storage under the condition described above, as assessed by various assays including, but not limited to, enzyme-linked immunosorbent assay (ELISA) and radioimmunoassay to measure the ability of, for example, an antibody or antibody fragment to specifically bind to a target antigen, by a C3a/C4a assay to measure the complement activating ability of the antibody and by chromium release assay to measure the ADCC activity of the antibody. The formulations retain after the storage for the above-defined periods more than 80%, more than 85%, more than 90%, more than 95%, more than 98%, more than 99%, or more than 99.5% of the initial biological activities of the formulation prior to the storage.

For example, the stability of the formulations may be evaluated by HPSEC or rCGE, wherein the percent area of the peaks represents the non-degraded protein. In particular, approximately 250 μg of, for example, the antibody or antibody fragment that specifically binds to a target antigen (approximately 25 μl of a liquid formulation comprising 10 mg/ml said antibody or antibody fragment) is injected onto a TosoH Biosep TSK G3000SWXL column (7.8 mm×30 cm) fitted with a TSK SW x1 guard column (6.0 mm CX 4.0 cm). The antibody or antibody fragment is eluted isocratically with 0.1 M disodium phosphate containing 0.1 M sodium sulfate and 0.05% sodium azide, at a flow rate of 0.8 to 1.0 ml/min. Eluted protein is detected using UV absorbance at 280 nm. A suitable reference standard is run in the assay as a control, and the results are reported as the area percent of the product monomer peak compared to all other peaks excluding the included volume peak observed at approximately 12 to 14 minutes. Peaks eluting earlier than the monomer peak are recorded as percent aggregate.

In certain embodiments, the formulations of the multidomain protein exhibit low to undetectable levels of aggregation as measured by HPSEC or rCGE, that is, no more than 5%, no more than 4%, no more than 3%, no more than 2%, no more than 1%, or no more than 0.5% aggregate by weight protein, and low to undetectable levels of fragmentation, that is, 80% or higher, 85% or higher, 90% or higher, 95% or higher, 98% or higher, or 99% or higher, or 99.5% or higher of the total peak area in the peak(s) representing intact protein. In the case of SDS-PAGE, the density or the radioactivity of each band stained or labeled with radioisotope can be measured and the % density or % radioactivity of the band representing non-degraded multidomain protein can be obtained.

The stability of the formulations can be also assessed by any assays that measure the biological activity of the multidomain protein in the formulation. For example, the biological activities of antibodies include, but are not limited to, antigen-binding activity, complement-activation activity, Fc-receptor binding activity, and so forth. Antigen-binding activity of the antibodies can be measured by any method known to those skilled in the art, including but not limited to ELISA, radioimmunoassay, Western blot, BlAcore, and the like. Complement-activation activity can be measured by a C3a/C4a assay in the system where the antibody which specifically binds to an antigen is reacted in the presence of the complement components with the cells expressing the antigen. Also see Harlow et al., Antibodies: A Laboratory Manual, (Cold Spring Harbor Laboratory Press, 2nd ed. 1988). An ELISA based assay, e.g., may be used to compare the ability of an antibody or fragment thereof to specifically bind to a target antigen to a suitable reference standard. In this assay, plates are coated with the target antigen and the binding signal of a set concentration of a suitable reference standard is compared to the binding signal of the same concentration of a test antibody or antibody fragment.

The purity of the multidomain protein formulations may be measured by any method well-known to one of skill in the art such as, e.g., HPSEC. The sterility of the multidomain protein formulations may be assessed by methods well known in the art. For example, sterile soybean-casein digest medium and fluid thioglycollate medium are inoculated with a test protein formulation by filtering a liquid protein formulation through a sterile filter having a nominal porosity of 0.45 µm. When using the Sterisure™ or Steritest™ method, each filter device is aseptically filled with approximately 100 ml of sterile soybean-casein digest medium or fluid thioglycollate medium. When using the conventional method, the challenged filter is aseptically transferred to 100 ml of sterile soybean-casein digest medium or fluid thioglycollate medium. The media are incubated at appropriate temperatures and observed three times over a 14 day period for evidence of bacterial or fungal growth.

The methods described above can be used to generate antibody therapeutics targeting any infectious organisms, including but not limited to any viruses and bacteria.

The methods described above can also be used to generate antibody therapeutics targeting other antigens, including but not limited to 17-1A, $\alpha 4\beta 7$ integrin receptor, AFP, CBL, CD11, CD11a, CD14, CD147, CD18, CD20, CD22, CD23, CD25, CD3, CD33, CD4, CD40, CD40L, CD44, CD52, CD64 (FcR), CD80, CEA, Complement (C5), CTLA-4, EGF receptor, Ep-CAM, E-selectin, Factor VII, FcRI receptors, Gamma Interferon, GD2-ganglioside, gp IIIb/IIIa, gp72, HER-2, HLA-DR 10 beta, HLA-DR antigen, ICAM-3, IgE, IL-4, IL5, IL-5, IL-8, inhibitor of P38MAP kinase, inosine monophosphate dehydrogenase, ganglioside GD3, MUC-1, nuC242, PEM antigen, SK-1 antigen, TNF alpha, VEGF, VEGF-receptor, and VLA-4.

In certain specific embodiments, the methods described above can also be used to generate antibody therapeutics that specifically binds to an antigen of RSV, an antigen of human metapneumovirus (hMPV), integrin $\alpha_v\beta_3$, CD2, CD19, EphA2, EphA4, or IL-9. Additional nonlimiting therapeutic targets are described in section 5.3 below.

5.2. Methods for Evaluating and/or Improving the Shelf Life of a Formulations Comprising a Multidomain Protein The invention also provides a method for evaluating the shelf-life of a multidomain protein formulation. The methods of the invention involves evaluating the thermal denaturation and/or renaturation behavior of a multidomain protein in a liquid preparation, which comprises a multidomain protein of interest having a domain the unfolding of which leads to aggregation of the multidomain protein in the liquid protein preparation. In one embodiment, the denaturation/renaturation behavior of the liquid protein preparation is determined by measuring a thermal denaturation/renaturation curve. The method then provides an indicator for the shelf life of the preparation based on the thermal denaturation and/or renaturation curve. For example, if the domain does not refold upon cooling or denatures at a low temperature, the multidomain protein is likely to have a short shelf life.

The invention also provides a method of evaluating long term stability of a multidomain protein in a solution, wherein the long term stability is defined as less than 5%, less than 10%, or less than 20% aggregation upon storage for a predetermined period of time at a predetermined temperature. The method comprises (a) providing a solution of a multidomain protein; (b) denaturing one or more domains of the multidomain protein by heating the solution of the multidomain protein; (c) determining if the domains refold upon cooling; and (d) classifying the multidomain protein as having long term stability in the solution if the domains are determined to refold in step (c). It is contemplated that the stability of a multidomain protein may be evaluated in a number of different solutions thereby identifying a particular solution useful for stabilizing a multidomain protein. Alternatively, or optionally, the method may be utilized to compare several different multidomain proteins having a desired biological activity above a predetermined threshold level, wherein each multidomain protein is formulated in a solution having identical components with the exception of the multidomain protein.

It is contemplated that a multidomain protein may comprise a domain the unfolding of which causes aggregation of the multidomain protein. Accordingly, the invention also provides a method for identifying a domain in a multidomain protein, which domain is responsible for aggregation of the protein. In one embodiment, the method of identifying one or more domain in a multidomain protein, which is responsible for aggregation comprises (a) denaturing one or more domains of the multidomain protein by heating said solution; (b) determining if one or more of said domains refold upon cooling; and (c) identifying one or more domains that do not refold upon cooling in step (b), thereby identifying a domain or domains, the unfolding of which causes aggregation of said multidomain protein in said solution.

The invention also provides a method of engineering a multidomain protein to have improved long term stability in a solution, wherein said long term stability is defined as less than 5%, less than 10%, or less than 20% aggregation upon storage for a predetermined period of time at a predetermined temperature. The method of engineering a multidomain protein to have improved long term stability in a solution comprises (a) modifying a domain of the multidomain protein by replacing one or more amino acid residues in the domain to generated a modified domain; (b) denaturing the modified domain by heating a solution of a multidomain protein comprising the modified domain; (c) determining if said modified domain in the multidomain protein refolds upon cooling; and (d) classifying the multidomain protein containing the modified domain as having improved long term stability if the modified domain is determined to refold in step (c). In one embodiment, the multidomain protein is an antibody. It is contemplated that steps (a) to (d) may be performed on an isolated domain. For example, a Fab domain, the unfolding of which causes aggregation of an antibody, may be isolated, modified denatured, renatured and classified. In one embodiment, the identified domain having improved long term stability is used in the generation of a multidomain protein. In one embodiment, the multidomain protein is an antibody. In another embodiment, the domain is an antigen binding domain. In yet another embodiment, the domain is a constant region domain. In certain embodiments, the multidomain protein comprises a domain the unfolding of which causes aggregation of the multidomain protein in the solution.

The invention further provides a method of screening for a multidomain protein which has improved long term stability in a solution, wherein the long term stability is defined as less than 5%, less than 10%, or less than 20% aggregation upon storage for a predetermined period of time at a predetermined temperature. In certain embodiments, a multidomain protein comprises a domain the unfolding of which causes aggregation of the multidomain protein in a solution. In one embodiment, the method comprises (a) denaturing respectively two or more multidomain proteins that are members of a population multidomain proteins, wherein each multidomain proteins comprises a different modified domain, the modified domain having one or more amino acid residues substituted, wherein the denaturing is accomplished by heating a solution of one of the multidomain proteins comprising the modified domain; (b) determining if the different modified domains in each multidomain protein denatured in step (a) refolds upon cooling; and (c) identifying the multidomain proteins containing a modified domain that is determined to refold in step (b) as having improved long term stability. In one embodiment, the method further comprises generating the population of different multidomain proteins. It is contemplated that steps (a) to (c) may be performed on isolated domains. For example, a Fab domain, the unfolding of which causes aggregation of an antibody, may be isolated and modified to generate a population of different modified domains two or more of which may then be screened by the method. In one embodiment, the identified domain having improved long term stability is used in the generation of a multidomain protein. In a specific embodiment the multidomain protein is an antibody. In one embodiment, the domain is an antigen binding domain (e.g., a Fab domain). In another embodiment, the domain is a constant region domain.

In certain embodiments, the denaturation and renaturation (i.e., refolding upon cooling) steps are carried out by generating a thermal denaturation/renaturation curve, e.g., using differential scanning calorimetry. The magnitude of the change in a physical property associated with the thermal denaturation of the multidomain protein as a result of heating is measured over a range of temperatures to generate a thermal denaturation/renaturation curve. It is contemplated that the temperature range encompasses the desired storage temperature range.

As used herein, a "thermal denaturation/renaturation curve" is a plot of a change in a physical property associated with the denaturation or renaturation of a protein as a function of temperature. See, for example, Davidson et al., Nature Structure Biology 2:859 (1995); Clegg, R. M. et al., Proc. Natl. Acad. Sci. U.S.A. 90:2994-2998 (1993). Any physical property of the protein which changes during denaturation, e.g., the emission of light or heat, the absorption of light or heat, scattering of light, and dichroism, may be used for monitoring the structural change of the protein. Examples of such physical properties include fluorescent emission, fluorescent energy transfer, absorption of ultraviolet or visible light, changes in polarization of light, and light scattering. Fluorescence emission can be intrinsic to a protein or can be due to a fluorescence reporter molecule.

As used herein, "aggregation" refers to a physical interaction between the protein or polypeptide molecules that result in formation of multimers. The multimers may remain soluble, or precipitate out of solution.

The multidomain protein formulation can be a solution of the multidomain protein of a suitable concentration, e.g., a concentration of 20, 30, 40, 50, 100 mg/ml or higher. The liquid multidomain protein formulation can also comprise other constituents, including but are not limited to, salts, ligands, co-factors, etc. The concentration and constituents of the liquid multidomain protein formulation are selected such that the thermal denaturation/renaturation behavior of the multidomain protein in the liquid multidomain protein formulation reflects the long term stability of the liquid multidomain protein formulation whose shelf life is to be evaluated. In one embodiment, the concentration of the multidomain protein in the liquid multidomain protein formulation being analyzed differs from the concentration of the multidomain protein in a liquid protein formulation by no more than 50%, 20%, 10%, 5% or 1%. In a specific embodiment, the concentration of the multidomain protein in the liquid multidomain protein formulation being analyzed is substantially the same as the concentration of the multidomain protein in a multidomain protein formulation.

The multidomain protein can comprise other amino acid residues or domains in addition to the aggregation-causing domain.

The concentration of a multidomain protein in a liquid formulation is at least 15 mg/ml, at least 20 mg/ml, at least 25 mg/ml, at least 30 mg/ml, at least 35 mg/ml, at least 40 mg/ml, at least 45 mg/ml, at least 50 mg/ml, at least 55 mg/ml, at least 60 mg/ml, at least 65 mg/ml, at least 70 mg/ml, at least 75 mg/ml, at least 80 mg/ml, at least 85 mg/ml, at least 90 mg/ml, at least 95 mg/ml, at least 100 mg/ml, at least 105 mg/ml, at least 110 mg/ml, at least 115 mg/ml, at least 120 mg/ml, at least 125 mg/ml, at least 130 mg/ml, at least 135 mg/ml, at least 140 mg/ml, at least 150 mg/ml, at least 200 mg/ml, at least 250 mg/ml, or at least 300 mg/ml.

The formulations may also comprise other substances, e.g., histidine, glycine, saccharides (e.g., sucrose, mannose, trehalose, etc.), polyols, (e.g., Tween) and sugar alcohols (e.g., mannitol, sorbitol, etc.). The concentration of histidine which is included in the formulations ranges from 1 mM to 100 mM, or from 5 mM to 50 mM. Histidine can be in the form of L-histidine, D-histidine, or a mixture thereof, but L-histidine is generally preferred. Histidine can be also in the form of hydrates. Histidine may be used in a form of pharmaceutically acceptable salt, such as hydrochloride (e.g., monohydrochloride and dihydrochloride), hydrobromide, sulfate, acetate, etc. The purity of histidine should be at least 98%, preferably at least 99%, and most preferably at least 99.5%.

The concentration of an amino acid to be used in a formulation can be at a concentration of less than 150 mM, less than 100 mM, less than 75 mM, less than 50 mM, less than 25 mM, less than 10 mM, less than 5.0 mM, or less than 2.0 mM. The amount of amino acid in the formulation should not cause a significant buffering effect so that protein precipitation at its isoelectric point can be avoided. An amino acid may be also used in a form of pharmaceutically acceptable salt, such as hydrochloride, hydrobromide, sulfate, acetate, etc. The purity of the amino acid should be at least 98%, or at least 99%, or at least 99.5%.

The saccharide can be sucrose at a concentration ranging from between about 1% to about 20%, preferably about 5% to about 15%, and more preferably about 8% to 10%. The polyol can be polysorbate (e.g., Tween 20) at a concentration ranging from between about 0.001% to about 1%, or about 0.01% to about 0.1%.

The pH of the formulation should not be equal to the isoelectric point of the particular multidomain protein to be used in the formulation and may range from about 5.0 to about 8.0, or about 5.5 to about 6.5, or about 6.0 to about 7.0, or about 6.5 to about 7.5, or about 7.0 to about 8.0, or about 5.8 to about 6.2, and or about 6.0.

Liquid formulations preferably exhibit stability at the temperature ranges of 38° C.-42° C. for at least 15 days and, in some embodiments, not more than 25 days, of 20° C.-24° C. for at least 1 month, at least 2 months, at least 4 months, or at least 6 months, of 2° C.-8° C. (in particular, at 4° C.) for at least 6 months, at least 1 year, at least 1.5 years, at least 2 years, at least 3 years or at least 4 years and at −20° C. for at least 1 year, at least 2 years, at least 3 years, at least 4 years, or at least 5 years, as assessed by high performance size exclusion chromatography (HPSEC). Namely, the formulations, more specifically liquid formulations, have low to undetectable levels of aggregation and/or fragmentation, as defined herein, after the storage for the defined periods as set forth above. In certain embodiments, no more than 5%, no more than 4%, no more than 3%, no more than 2%, no more than 1%, and or no more than 0.5% of the multidomain protein forms an aggregate as measured by HPSEC, after the storage for the defined periods as set forth above.

In one embodiment, a suitable solution of a multidomain protein that comprises a domain whose unfolding leads to aggregation of the multidomain protein whose shelf life is of interest is provided, wherein the solution stabilizes the domain. In another embodiment, a suitable solution of a multidomain protein comprising an engineered domain having improved long term stability is provided.

A lyophilized formulation preferably exhibits no significant changes observed at a refrigerated temperature (2-8° C.) for at least 12 months, preferably 2 years, and more preferably 3 years; or at room temperature (23-27° C.) for at least 3 months, preferably 6 months, and more preferably 1 year. The criteria for stability are as follows: No more than 10%, or no more than 5%, of the protein domain is degraded as measured by HPSEC. The rehydrated solution is colorless, or clear to slightly opalescent by visual analysis. The concentration, pH and osmolality of the formulation have no more than ±10% change. Potency is within 70-130, preferably 80-120% of the control. No more than 10%, preferably 5% of clipping is observed. No more than 10%, or no more than 5% of aggregation is formed.

The methods of screening and/or evaluating the long term stability of a multidomain protein in a solution of the invention can provide an indicator of the shelf life of a plurality of formulations of different multidomain proteins, e.g., a plurality of different monoclonal antibodies. In one embodiment, a suitable solution of a multidomain protein is provided for each multidomain protein. Alternatively, the methods of screening and/or evaluating the long term stability of a multidomain protein in a solution of the invention can provide an indicator of the shelf life of a plurality of different solutions comprising the same multidomain protein. In another embodiment, a multidomain protein is formulated in a number of different solutions. In certain embodiments, each multidomain protein comprises a domain whose unfolding leads to aggregation of the corresponding multidomain protein. In other embodiments, each multidomain protein comprises a variant of a domain whose unfolding leads to aggregation of the corresponding multidomain protein. A thermal denaturation curve is measured for each of such multidomain proteins. The multidomain proteins are then ranked based on the denaturation temperatures of the multidomain proteins. The lower denaturation temperature corresponds to lower stability, and thus is indicative of a shorter shelf life.

In one embodiment, the methods of screening and/or evaluating the long term stability of a multidomain protein in a solution is used as an indicator of the shelf life of a plurality of formulations of different modified multidomain proteins. Each of the plurality of modified multidomain proteins comprises a domain in a modified form, e.g., having one or more amino acid residues in the domain substituted. A suitable solution of a multidomain protein comprising a modified domain is provided for each modified multidomain protein. A thermal denaturation curve is measured for each of such multidomain proteins. The modified multidomain proteins are then ranked based on the denaturation temperatures of the multidomain proteins. One or more modified monoclonal multidomain protein may be selected based on the rank order. In a specific embodiment, the multidomain protein is an antibody.

The methods of screening and/or evaluating the long term stability of a multidomain protein in a solution can also be used for identifying biochemical conditions that optimize the stability of, and hence the shelf life of, a formulation of a multidomain protein. For example, pH affects the shelf life of a protein. For a liquid formulation the composition of the solvent, e.g., water, also affect the shelf life of a protein. For example, glycerol alters the solvation properties of water to favor the native conformation of proteins. Ligands and cofactors in the solution may also affect the shelf life of a protein. Other biochemical parameters that have been shown to affect protein folding are: protein concentration, temperature, glutathione redox buffers (GSH, GSSG), the presence of detergents, and the presence of other additives, such as glycerol, arginine-HCl, polyethylene glycol (PEG), and organic solvents. Various conditions can be optimized, including pH optimum, ionic strength dependence, concentration of salts of the Hofmeister series, glycerol concentration, sucrose concentration, arginine concentration, dithiothreitol concentration, metal ion concentration, etc. Such biological conditions can be evaluated based on the thermal denaturation curve of the multidomain protein under the conditions. In one embodiment, a plurality of different conditions are ranked, and the optimal one is selected.

In one embodiment, the thermal denaturation/renaturation curve is obtained using differential scanning calorimetry (DSC). In this embodiment, a DSC thermogram of the denaturation/renaturation of the multidomain protein is obtained. Methods of using DSC to study the denaturation of proteins are well known in the art (see, e.g., Vermeer et al., 2000, Biophys. J. 78:394-404; Vermeer et al., 2000, Biophys. J. 79: 2150-2154). DSC can detect fine-tuning of interactions between the individual domains of a protein (Privalov et al., 1986, Methods Enzymol. 131:4-51).

In one embodiment, DSC measurements are performed using a Setaram Micro-DSC III (Setaram, Caluire, France). The samples are placed in the calorimeter in a 1 ml sample cell against a 1 ml reference cell containing the appropriate blank solution. The cells are stabilized for 4 h at 25° C. inside the calorimeter before heating up to the final temperature at a selected heating rate. The transition temperature and enthalpy are determined using the Setaram software (Setaram, Version 1.3).

In another embodiment, DSC measurements are performed using a VP-DSC (MicroCal, LLC). In one embodiment, a scan rate of 1.0° C./min and a temperature range of 25-120° C. are employed. A filter period of 8 seconds is used along with a 5 minute pre-scan thermostating. Multiple baselines are run with buffer in both the sample and reference cell to establish thermal equilibrium. After the baseline is subtracted from the sample thermogram, the data are concentration normalized and fitted using the deconvolution function. Melting temperatures are determined following manufacturer procedures using Origin software supplied with the system.

In another embodiment, the thermal denaturation/renaturation curve is obtained using circular dichroism (CD) spectroscopy. Changes in the secondary structure of IgG as a function of temperature and/or, e.g., pH, can be studied by CD spectroscopy (Fasman, 1996, Circular Dichroism and the Conformational Analysis of Biomolecules. Plenum Press, New York). The advantage of this technique are that the spectroscopic signal is not affected by the presence of the surrounding solution and that well-defined procedures are available to elucidate the secondary structure based on reference spectra of the different structure elements (de Jongh et al., 1994, Biochemistry. 33:14521-14528). The fractions of the secondary structural elements can be obtained from the CD spectra.

In one embodiment, the CD spectra are measured with a JASCO spectropolarimeter, model J-715 (JASCO International Co., Tokyo, Japan). A quartz cuvette of 0.1 cm light path length is used. Temperature regulation is carried out using a JASCO PTC-348WI (JASCO International) thermocouple. Temperature scans are recorded at a selected heating rate using the Peltier thermocouple with a resolution of 0.2° C. and a time constant of 16 s. Wavelength scans, in the far-UV region (0.2 nm resolution) are obtained by accumulation of a plurality of scans with a suitable scan rate.

The thermal denaturation/renaturation curve can also be measured by light spectrophotometry. When a protein in a solution denatures in response to heating, the molecules aggregate and the solution scatters light more strongly. Aggregation leads to changes in the optical transparency of the sample, and can be measured by monitoring the change in absorbance of visible or ultraviolet light of a defined wavelength.

In still another embodiment, fluorescence spectroscopy is used to obtain the thermal denaturation/renaturation curve. In one embodiment, intrinsic protein fluorescence, e.g., intrinsic tryptophan fluorescence, is monitored. In another embodiment, fluorescence probe molecules are monitored. Methods of performing fluorescence spectroscopy experiments are well known to those skilled in the art. See, for example, Bashford, C. L. et al., Spectrophotometry and Spectrofluorometry: A Practical Approach, pp. 91-114, IRL Press Ltd. (1987); Bell, J. E., Spectroscopy in Biochemistry, Vol. I, pp. 155-194, CRC Press (1981); Brand, L. et al., Ann. Rev. Biochem. 41:843 (1972).

The methods of the invention can be practiced using an array format, in which a plurality of different liquid multidomain protein preparations is evaluated simultaneously (see, U.S. Pat. No. 6,232,085). The array format is particular useful for evaluating the potential shelf life of a plurality of formulations of different multidomain proteins, e.g., a plurality of modified monoclonal antibodies, or the shelf life of a multidomain protein under a plurality of different biochemical conditions.

5.3. Multidomain Proteins

In one embodiment the methods of the present invention are useful for the generation of multidomain proteins with improved manufacturing characteristics (referred to herein as "multidomain proteins of the invention") that specifically bind to a target molecule. Such multidomain proteins include but are not limited to antibodies including antibody domain fusion proteins. In one embodiment, a multidomain protein of the invention specifically binds a nonpolypeptide target. In another embodiment, a multidomain protein of the invention specifically binds a polypeptide target. In another embodiment, administration of a multidomain protein of the invention to a mammal suffering from a disease or disorder can result in a therapeutic benefit in that mammal.

Antibody domain fusion proteins include Fc fusion proteins, which combines an Fc domain or fragment thereof, with a fusion partner, which in general can be any protein, polypeptide, peptide, including, but not limited to, the target-binding region of a receptor, an adhesion molecule, a ligand, an enzyme, or some other protein or protein domain. Antibody domain fusion proteins also include antigen binding domain fusion proteins, which combines an antigen binding domain or fragment thereof, with a fusion partner, which in general can be any protein, polypeptide, peptide, including, but not limited to, another antigen binding domain, the target-binding region of a receptor, an adhesion molecule, a ligand, an enzyme, a toxin or some other protein or protein domain. It will be understood that the role of the fusion partner is determined by the therapeutic goal. For example the role of the non-Fc part of an Fc fusion is generally to mediate target binding, and thus it is functionally analogous to the variable regions of an antibody while the role of the fusion partner of an antigen binding domain fusion protein may be to mediate binding to a second target in the case of a second antigen binding domain or to provide a cytotoxic agent in the case of a toxin.

Virtually any molecule may be targeted by and/or incorporated into a multidomain protein of the invention including, but not limited to, following list of proteins, subunits, domains, motifs, and epitopes belonging to the following list of cellular proteins: renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VII, factor VIIIC, factor DC, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor (TNF) proteins such as TNF-alpha, TNF-beta, TNFbeta2, TNFc, TNFalphabeta, 4-1BBL as well as members of the TNF superfamily members such as, TNF-like weak inducer of apoptosis (TWEAK), and LIGHT, B lymphocyte stimulator (BlyS); members of the TNF receptor superfamily including TNF-RI, TNF-RII, TRAIL receptor-1, Transmembrane activator and CAML interactor (TACI) and OX40L; Fas ligand (FasL); enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors such as, for example, EGFR (ErbB-1), VGFR; interferons such as alpha interferon (α-IFN), beta interferon (β-IFN) and gamma interferon (γ-IFN); interferon alpha receptor (IFNAR) subunits 1 and/or 2 and other receptors such as, A1, Adenosine Receptor, Lymphotoxin Beta Receptor, BAFF-R, endothelin receptor; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor; platelet-derived growth factor (PDGF); fibroblast growth factor such as αFGF and βFGF; epidermal growth factor (EGF); transforming growth factor (TGF) such as TGF-alpha and TGF-beta, including TGF-1, TGF-2, TGF-3, TGF-4, or TGF-5; insulin-like growth factor-I and -II (IGF-I and IGF-II); des (1-3)-IGF-I (brain IGF-I), insulin-like growth factor binding proteins, keratinocyte growth factor; growth factor receptors such as, FGFR-3, IGFR; CD proteins such as CD2, CD3, CD3E, CD4, CD 8, CD11, CD11a, CD14, CD16, CD18, CD19, CD20, CD22, CD23, CD25, CD27, CD27L, CD28, CD29, CD30, CD30L, CD32, CD33 (p67 protein), CD34, CD38, CD40, CD40L, CD52, CD54, CD56, CD63, CD64, CD80 and CD147; erythropoietin; osteoinductive factors; immunotoxins; a bone morphogenetic protein (BMP); an interferon such as interferon-alpha, -beta, and -gamma; colony stimulating factors (CSFs), such as M-CSF, GM-CSF, and G-CSF; interleukins (ILs), e.g., IL-1 to IL-13 and IL-15, IL-18, IL-23; EPO; superoxide dismutase; T-cell receptors alpha/beta; surface membrane proteins; decay accelerating factor; transport proteins; homing receptors; addressins; regulatory proteins; chemokine family members such as the eotaxins, the MIPs, MCP-1, RANTES; cell adhesion molecules such as selectins (L-selectin, P-selectin, E-selectin) LFA-1, LFA-3, Mac 1, p150.95, VLA-1, VLA-4, ICAM-1, ICAM-3, EpCAM and VCAM, a4/p7 integrin, and Xv/p3 integrin, integrin alpha subunits such as CD49a, CD49b, CD49c, CD49d, CD49e, CD49f, alpha7, alpha8, alpha9, alphaD, CD11a, CD11b, CD51, CD11c, CD41, alphaIIb, alphaIELb; integrin beta subunits such as, CD29, CD 18, CD61, CD104, beta5, beta6, beta7 and beta8; Integrin subunit combinations including but not limited to, αVβ3, αVβ5 and α4β7; cellular ligands such as, TNF-related apoptosis-inducing ligand (TRAIL), A proliferation-inducing ligand (APRIL), B Cell Activating Factor (BAFF), a member of an apoptosis pathway; IgE; blood group antigens; flk2/flt3 receptor; obesity (OB) receptor; mpl receptor; CTLA-4; protein C; an Eph receptor such as EphA2, EphA4, EphB2, etc.; immune system markers, receptors and ligands such as CTLA-4, T cell receptor, B7-1, B7-2, IgE, Human Leukocyte Antigen (HLA) such as HLA-DR, CBL; complement proteins such as complement receptor CR1, C1Rq and other complement factors such as C3, and C5; blood factors including tissue factor, factor VII; a glycoprotein receptor such as GpIbα, GPIIb/IIIa and CD200; and fragments of any of the above-listed polypeptides.

Also contemplated are multidomain proteins of the invention that specifically bind cancer antigens including, but not limited to, ALK receptor (pleiotrophin receptor), pleiotrophin; KS 1/4 pan-carcinoma antigen; ovarian carcinoma antigen (CA125); prostatic acid phosphate; prostate specific antigen (PSA); melanoma-associated antigen p97; melanoma antigen gp75; high molecular weight melanoma antigen (HMW-MAA); prostate specific membrane antigen; carcinoembryonic antigen (CEA); carcinoembryonic antigen-related cell adhesion molecule (CEACAMI); cytokeratin tumor-associated antigen; human milk fat globule (HMFG) antigen; tumor-associated antigen expressing Lewis Y related carbohydrate; colorectal tumor-associated antigens such as: CEA, tumor-associated glycoprotein-72 (TAG-72), CO17-1A, GICA 19-9, CTA-1 and LEA; Burkitt's lymphoma antigen-38.13; CD19; human B-lymphoma antigen-CD20; CD33; melanoma specific antigens such as ganglioside GD2, ganglioside GD3, ganglioside GM2 and ganglioside GM3; tumor-specific transplantation type cell-surface antigen (TSTA); virally-induced tumor antigens including T-antigen, DNA tumor viruses and Envelope antigens of RNA tumor viruses; oncofetal antigen-alpha-fetoprotein such as CEA of colon, 5T4 oncofetal trophoblast glycoprotein and bladder tumor oncofetal antigen; differentiation antigen such as human lung carcinoma antigens L6 and L20; antigens of fibrosarcoma; human leukemia T cell antigen-Gp37; neoglycoprotein; sphingolipids; breast cancer antigens such as EGFR (Epidermal growth factor receptor); NY-BR-16; NY-BR-16 and HER2 antigen (p185HER2); Her2/neu (ErbB-2), Her3 (ErbB-3), Her4 (ErbB-4), polymorphic epithelial mucin (PEM) antigen; epithelial membrane antigen (EMA); Melanoma-associated antigen MUC18; MUC1; malignant human lymphocyte antigen-APO-1; differentiation antigen such as I antigen found in fetal erythrocytes; primary endoderm I antigen found in adult erythrocytes; preimplantation embryos; I(Ma) found in gastric adenocarcinomas; M18, M39 found in breast epithelium; SSEA-1 found in myeloid cells; VEP8; VEP9; Myl; VIM-D5; D156-22 found in colorectal cancer; TRA-1-85 (blood group H); SCP-1 found in testis and ovarian cancer; C14 found in colonic adenocarcinoma; F3 found in lung adenocarcinoma; AH6 found in gastric cancer; Y hapten; Ley found in embryonal carcinoma cells; TL5 (blood group A); EGF receptor found in A431 cells; E1 series (blood group B) found in pancreatic cancer; FC10.2 found in embryonal carcinoma cells; gastric adenocarcinoma antigen; CO-514 (blood group Lea) found in Adenocarcinoma; NS-10 found in adenocarcinomas; CO-43 (blood group Leb); G49 found in EGF receptor of A431 cells; MH2 (blood group ALeb/Ley) found in colonic adenocarcinoma; 19.9 found in colon cancer; gastric cancer mucins; T5A7 found in myeloid cells; R24 found in melanoma; 4.2, GD3, D1.1, OFA-1, GM2, OFA-2, GD2, and M1:22:25:8 found in embryonal carcinoma cells and SSEA-3 and SSEA-4 found in 4 to 8-cell stage embryos; Cutaneous T cell Lymphoma antigen; MART-1 antigen; Sialy Tn (STn) antigen; Anaplastic lymphoma kinase (ALK) found in large cell lymphoma; Colon cancer antigen NY-CO-45; Lung cancer antigen NY-LU-12 variant A; Adenocarcinoma antigen ART1; Paraneoplastic associated brain-testis-cancer antigen (onconeuronal antigen MA2; paraneoplastic neuronal antigen); Neuro-oncological ventral antigen 2 (NOVA2); Hepatocellular carcinoma antigen gene 520; TUMOR-ASSOCIATED ANTIGEN CO-029; Tumor-associated antigens MAGE-C1 (cancer/testis antigen CT7), MAGE-B1 (MAGE-XP antigen), MAGE-B2 (DAM6), MAGE-2, MAGE-4a, MAGE-4b and MAGE-X2; Cancer-Testis Antigen (NY-EOS-1); placental alkaline phosphatase (PLAP) and testicular PLAP-like alkaline phosphatase, transferrin receptor; Heparanase I; EphA2 associated with numerous cancers and fragments of any of the above-listed polypeptides.

Other exemplary polypeptide targets include but not limited to the following list of proteins, subunits, domains, motifs, and epitopes belonging to the following list of microbial proteins: human cytomegalovirus (HCMV) proteins such as, envelope glycoprotein, gB, internal matrix proteins of the virus, pp65 and pp150, immediate early (IE) proteins; human immunodeficiency virus (HIV) proteins such as, Gag, Pol, Vif and Nef (Vogt et al., 1995, Vaccine 13: 202-208); HIV antigens gp120 and gp160 (Achour et al., 1995, Cell. Mol. Biol. 41: 395-400; Hone et al., 1994, Dev. Biol. Stand. 82: 159-162); gp41 epitope of human immunodeficiency virus (Eckhart et al., 1996, J. Gen. Virol. 77: 2001-2008); hepatitis C virus (HCV) proteins such as, nucleocapsid protein in a secreted or a nonsecreted form, core protein (pC); E1 (pE1), E2 (pE2) (Saito et al., 1997, Gastroenterology 112: 1321-1330), NS3, NS4a, NS4b and NS5 (Chen et al., 1992, Virology 188:102-113); severe acute respiratory syndrome (SARS) corona virus proteins include but are not limited to, the S (spike) glycoprotein, small envelope protein E (the E protein), the membrane glycoprotein M (the M protein), the hemagglutinin esterase protein (the HE protein), and the nucleocapsid protein (the N-protein) See, e.g., Marra et al., "The Genome Sequence of the SARS-Associated Coronavirus," Science Express, May 2003); *Mycobacterium tuberculosis* proteins such as the 30-35 kDa (a.k.a. antigen 85, alpha-antigen) that is normally a lipoglycoprotein on the cell surface, a 65-kDa heat shock protein, and a 36-kDa proline-rich antigen (Tascon et al. (1996) Nat. Med. 2: 888-92), Ag85A, Ag85b (Huygen et al., 1996, Nat. Med. 2: 893-898), 65-kDa heat shock protein, hsp65 (Tascon et al., 1996, Nat. Med. 2: 888-892), MPB/MPT51 (Mild et al., 2004, Infect.

Immun. 72:2014-21), MTSP11, MTSP17 (Lim et al., 2004, FEMS Microbiol. Lett. 232:51-9 and supra); Herpes simplex virus (HSV) proteins such as gD glycoprotein, gB glycoprotein; proteins from intracellular parasites such as *Leishmania* include LPG, gp63 (Xu and Liew, 1994, Vaccine 12: 1534-1536; Xu and Liew, 1995, Immunology 84: 173-176), P-2 (Nylen et al., 2004, Scand. J. Immunol. 59:294-304), P-4 (Kar et al. 2000, J Biol. Chem. 275:37789-97), LACK (Kelly et al., 2003, J Exp. Med. 198:1689-98); microbial toxin proteins such as *Clostridium perfringens* toxin; in addition, exemplary antigen peptides of human respiratory syncytial virus (hRSV), human metapneumovirus (HMPV) and Parainfluenza virus (PIV) are detailed in: Young et al., in Patent publication WO04010935A2.

One skilled in the art will appreciate that the aforementioned lists of targets refers not only to specific proteins and biomolecules, but the biochemical pathway or pathways that comprise them. For example, reference to CTLA-4 as a target antigen implies that the ligands and receptors that make up the T cell co-stimulatory pathway, including CTLA-4, B7-1, B7-2, CD28, and any other undiscovered ligands or receptors that bind these proteins, are also targets. Thus target, as used herein, refers not only to a specific biomolecule, but the set of proteins that interact with the target and the members of the biochemical pathway to which the target belongs. One skilled in the art will further appreciate that any of the aforementioned target antigens, the ligands or receptors that bind them, or other members of their corresponding biochemical pathway, may be operably linked to the multidomain proteins or a portion thereof of the present invention in order to generate a fusion protein. Thus for example, a multidomain fusion that targets EGFR could be constructed by operably linking a multidomain protein or portion thereof to EGF, TGFα, or any other ligand, discovered or undiscovered, that binds EGFR. Accordingly, a multidomain protein or portion thereof of the present invention could be operably linked to EGFR in order to generate an fusion that binds EGF, TGFα, or any other ligand, discovered or undiscovered, that binds EGFR. Thus virtually any polypeptide, whether a ligand, receptor, or some other protein or protein domain, including but not limited to the aforementioned targets and the proteins that compose their corresponding biochemical pathways, may be operably linked to the multidomain proteins of the present invention or a portion thereof to develop a fusion.

In one embodiment the multidomain protein of the invention is an antibody or an antibody domain fusion protein. Numerous methods useful for the generation of antibodies or antibody domain fusion proteins are well known in the art. Several nonlimiting examples are described below in section 5.4. In a specific embodiment the methods of the present invention are utilized to generate and/or screen antibody or antibody domain fusion proteins which have preferred/improved manufacturing characteristics.

A number of specific multidomain proteins, namely antibodies and antibody domain fusion proteins (e.g., Fc fusions) that are approved for use, in clinical trials, or in development may benefit from the methods of the present invention. Said antibodies and antibody domain fusion proteins (e.g., Fc fusions) are herein referred to as "clinical products and candidates". Thus in specific embodiments, the methods of the present invention may find use in a range of clinical products and candidates. For example the engineering and screening methods of the present invention may find use developing an antibody with improved manufacturing characteristics that has binding and functional characteristics substantially similar to rituximab (Rituxan®, IDEC/Genentech/Roche) (see for example U.S. Pat. No. 5,736,137), a chimeric anti-CD20 IgG1 antibody approved to treat Non-Hodgkin's lymphoma; HuMax-CD20 (Genmab), an anti-CD20 (see for example PCT WO 04/035607); an anti-CD20 antibody described in U.S. Pat. No. 5,500,362; AME-I33 (Applied Molecular Evolution) humanized and optimized anti-CD20 Mab; hA20 (Immunomedics, Inc.) a humanized anti-CD20 Mab; HumaLYM™ (Intracel) a fully human anti-CD20 Mab; trastuzumab (Herceptin®, Genentech) a humanized anti-Her2/neu antibody approved to treat breast cancer (see for example U.S. Pat. No. 5,677,171); pertuzumab (rhuMab-2C4, Omnitarg™, Genentech); an anti-Her2 antibody described in U.S. Pat. No. 4,753,894; cetuximab (Erbitux®, Imclone) (U.S. Pat. No. 4,943,533; PCT WO 96/40210), a chimeric anti-EGFR antibody in clinical trials for a variety of cancers; ABX-EGF (Abgenix/Immunex/Amgen) described in U.S. Pat. No. 6,235,883; HuMax-EGFr (Genmab) described in U.S. patent application Ser. No. 10/172,317; 425, EMD55900, EMD62000, and EMD72000 (Merck KGaA) (U.S. Pat. No. 5,558,864); ICR62 (Institute of Cancer Research) (PCT WO 95/20045); TheraCIM hR3 (YM Biosciences, Canada and Centro de Immunologia Molecular, Cuba) (U.S. Pat. Nos. 5,891,996; 6,506,883); mAb-806 (Ludwig Institute for Cancer Research, Memorial Sloan-Kettering) (Jungbluth et al. 2003, Proc Natl Acad Sci USA. 100(2): 639-44); KSB-102 (KS Biomedix); MR1-1 (IVAX, National Cancer Institute) (PCT WO 01/62931); and SC100 (Scancell) (PCT WO 01/88138); alemtuzumab (Campath®, Genzyme), a humanized monoclonal anti CD52 IgG1 antibody currently approved for treatment of B-cell chronic lymphocytic leukemia; muromonab-CD3 (Orthoclone OKT3®, Ortho Biotech/Johnson & Johnson), an anti-CD3 antibody; OrthoClone OKT4A (Ortho Biotech), a humanized anti-CD4 IgG antibody; ibritumomab tiuxetan (Zevalin®, IDEC/Schering AG), a radiolabeled anti-CD20 antibody; gemtuzumab ozogamicin (Mylotarg®, Celltech/Wyeth), an anti-CD33 (p67 protein) antibody; alefacept (Amevive®, Biogen), an anti-LFA-3 Fc fusion; abciximab (ReoPro®, Centocor/Lilly), a anti-glycoprotein IIb/IIIa receptor on the platelets for the prevention of clot formation; basiliximab (Simulect®, Novartis) an anti-CD25 antibody; infliximab (Remicade®, Centocor), an anti-TNFalpha antibody; adalimumab (Humira®, Abbott), an anti-TNFalpha antibody; Humicade™ (CellTech), an anti-TNFalpha antibody; etanercept (Enbrel®, Immunex/Amgen), an anti-TNFalpha Fc fusion; ABX-CBL (Abgenix), an anti-CD147 antibody; ABX-IL8 (Abgenix), an anti-1L8 antibody; ABX-MA1 (Abgenix), an anti-MUC18 antibody; Pemtumomab (R1549, 90Y-muHMFG1, Antisoma), an anti-MUC1 antibody; Therex (R1550, Antisoma), an anti-MUC1 antibody; AngioMab (AS1405, Antisoma), HuBC-1 and Thioplatin (AS1407) being developed by Antisoma; natalizumab (Antegren®, Biogen), an anti-alpha-4-beta-1 (VLA-4) and alpha-4-beta-7 antibody; ANTOVA™ (Biogen). a humanized anti-CD40L IgG antibody; VLA-1 mAb (Biogen), an anti-VLA-1 integrin antibody; LTBR mAb (Biogen), an anti-lymphotoxin beta receptor (LTBR) antibody; CAT-152 (Cambridge Antibody Technology), an anti-TGFβ2 antibody; J695 (Cambridge Antibody Technology/Abbott), an anti-IL-12 antibody; CAT-192 (Cambridge Antibody Technology/Genzyme); an anti-TGFβ1 antibody; CAT-213 (Cambridge Antibody Technology), an anti-Eotaxin1 antibody; LymphoStat-B™ an anti-Blys antibody and TRAIL-R1mAb, an anti-TRAIL-R1 antibody both being developed by Cambridge Antibody Technology and Human Genome Sciences, Inc.; bevacizumab (Avastin™, rhuMAb-VEGF, Genentech) an anti-VEGF antibody; an anti-HER receptor family antibody (Genentech); Anti-Tissue Factor antibody (Genentech); Omalizumab (Xolair™, Genentech) an anti-IgE antibody;

Efalizumab (Raptiva™, Genentech/Xoma), an anti-CD11a antibody; MLN-02 Antibody (formerly LDP-02, Genentech/Millenium Pharmaceuticals), a humanized anti-α4β7 antibody; HuMax CD4 (Genmab), an anti-CD4 antibody being; HuMax-IL 15 (Genmab and Amgen), an anti-IL15 antibody; HuMax-Inflam (Genmab/Medarex); HuMax-Cancer (Genmab/Medarex/Oxford GcoSciences), an anti-Heparanase I antibody; HuMax-Lymphoma (Genmab/Amgen); HuMax-TAC (Genmab); IDEC-131 (IDEC Pharmaceuticals), an anti-CD40L antibody; Clenoliximab (IDEC-151, IDEC Pharmaceuticals), an anti-CD4 antibody; IDEC-114 (IDEC Pharmaceuticals), an anti-CD80 antibody; IDEC-152 (IDEC Pharmaceuticals), an anti-CD23; anti-macrophage migration factor (MIF) antibodies being developed by IDEC Pharmaceuticals; BEC2 (Imclone), an anti-idiotypic antibody; IMC-1C11 (Imclone), an anti-KDR antibody; DC101 (Imclone), an anti-flk-1 antibody; anti-VE cadherin antibodies being developed by Imclone; labetuzumab (CEA-Cide™, Immunomedics), an anti-carcinoembryonic antigen (CEA) antibody; Epratuzumab (LymphoCide™, Immunomedics), an anti-CD22 antibody; AFP-Cide (Immunomedics); MyelomaCide (Immunomedics); LkoCide (Immunomedics); ProstaCide (Immunomedics); MDX-010 (Medarex), an anti-CTLA4 antibody; MDX-060 (Medarex), an anti-CD30 antibody; MDX-070 (Medarex); MDX-018 (Medarex); MDX-CD4 (Medarex/Eisai/Genmab), a human anti-CD4 IgG antibody; Osidem™ (IDM-1, Medarex/Immuno-Designed Molecules), an anti-Her2 antibody; HuMax™-CD4 (Medarex/Genmab), an anti-CD4 antibody; HuMax-IL15 (Medarex/Genmab); CNTO 148 (Medarex/Centocor/J&J), an anti-TNFα antibody; CNTO 1275 (Centocor/J&J), an anti-cytokine antibody; CNTO 95 (Centocor/J&J), a human Integrin αv antibody (PCT publication WO 02/12501); MOR101 and MOR102 (MorphoSys), anti-intercellular adhesion molecule-1 (ICAM-1) (CD54) antibodies; MOR201 (MorphoSys), an anti-fibroblast growth factor receptor 3 (FGFR-3) antibody; visilizumab (Nuvion®, Protein Design Labs), an anti-CD3 antibody; HuZAF™ (Protein Design Labs), an anti-gamma interferon antibody; Anti-α5β1 Integrin (Protein Design Labs); anti-IL-12 (Protein Design Labs); ING-1 (Xoma), an anti-Ep-CAM antibody; MLN01 (Xoma), an anti-Beta2 integrin antibody; ZENAPAX® (daclizumab, Roche Pharmaceuticals) an immunosuppressive, humanized anti-CD25 monoclonal antibody for the prevention of acute renal allograft rejection; CDP860 (Celltech, UK), a humanized, PEGylated anti-CD18 F(ab')2; PRO542 (Progenics/Genzyme Transgenics), an anti-HIV gp120 antibody fused with CD4; C14 (ICOS Pharm), an anti-CD14 antibody; OVAREX™ (Altarex), a murine anti-CA 125 antibody; PANOREX™ (Glaxo Wellcome/Centocor), a murine anti-17-IA cell surface antigen IgG2a antibody; VITAXIN™ (MedImmune, PCT publication No. WO 2003/075957), a humanized anti-αVβ3 integrin antibody; siplizumab (MEDI-507, MedImmune, WO 99/03502), a humanized form of the murine monoclonal anti-CD2 antibody, BTI-322; palivizumab (Synagis®, MedImmune), a humanized neutralizing anti-RSV antibody; MEDI-524 (Numax, MedImmune), an affinity optimized humanized anti RSV antibody; Zamyl (Smart M195, Protein Design Lab/Kanebo), a humanized anti-CD33 IgG antibody; Remitogen (Smart 1D10, Protein Design Lab/Kanebo) which is a humanized anti-HLA antibody; ONCOLYM™ (Lym-1, Techniclone) is a radiolabelled murine anti-HLA DR antibody; Efalizumab (Genetech/Xoma), a humanized monoclonal anti-CD11a antibody; ICM3 (ICOS Pharm), a humanized anti-ICAM3 antibody; IDEC-114 (DEC Pharm/Mitsubishi), a primatized anti-CD80 antibody; eculizumab (5G1.1, Alexion Pharm) a humanized anti-complement factor 5 (C5) antibody; pexelizumab (5G1.1-SC, Alexion Pharm) a fully humanized single chain monoclonal antibody; LDP-01 (Millennium/Xoma), a humanized anti-β2-integrin IgG antibody. In specific embodiments, the multidomain proteins of the invention are not Numax® or an antigen-binding fragment thereof (e.g., a Fab fragment of Numax®).

5.4. Generation of Antibodies

In one embodiment, the multidomain proteins of the invention are antibodies that specifically bind to a target molecule. Nonlimiting examples of target molecules are described above (see section 5.3). Antibodies that specifically bind any target (also referred to herein as "antigen") can be produced by any method known in the art for the synthesis of antibodies, in particular, by chemical synthesis or preferably, by recombinant expression techniques.

Polyclonal antibodies specific for an antigen can be produced by various procedures well-known in the art. For example, a human antigen can be administered to various host animals including, but not limited to, rabbits, mice, rats, etc. to induce the production of sera containing polyclonal antibodies specific for the human antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. Briefly, mice can be immunized with a non-murine antigen and once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding the antigen. Ascites fluid, which generally contains high levels of antibodies, can be generated by immunizing mice with positive hybridoma clones.

Monoclonal antibodies can be generated by the method comprising culturing a hybridoma cell secreting an antibody of the invention wherein, preferably, the hybridoma is generated by fusing splenocytes isolated from a mouse immunized with a non-murine antigen with myeloma cells and then screening the hybridomas resulting from the fusion for hybridoma clones that secrete an antibody able to bind to the antigen.

Antibody fragments which recognize specific particular epitopes (referred to herein as "antigen binding domain(s)") may be generated by any technique known to those of skill in the art. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain. Further, the antibodies of the present invention can also be generated using various phage display methods known in the art.

In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with an scFv linker by PCR and cloned into a phagemid vector. The vector is electroporated in E. coli and the E. coli is infected with helper phage. Phage used in these methods are typically filamentous phage including fd and M13 and the VH and VL domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies of the present invention include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; International application No. PCT/GB91/O1 134; International publication Nos. WO 90/02809, WO 91/10737, WO 92/01047, WO 92/18619, WO 93/11236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce Fab, Fab' and F(ab')2 fragments can also be employed using methods known in the art such as those disclosed in PCT publication No. WO 92/22324; Mullinax et al., 1992, BioTechniques 12(6):864-869; Sawai et al., 1995, AJRI 34:26-34; and Better et al., 1988, Science 240:1041-1043.

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a VH constant region, e.g., the human gamma 4 constant region, and the PCR amplified VL domains can be cloned into vectors expressing a VL constant region, e.g., human kappa or lamba constant regions. Preferably, the vectors for expressing the VH or VL domains comprise a promoter, a secretion signal, a cloning site for the variable domain, constant domains, and a selection marker such as neomycin. The VH and VL domains may also cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

Methods for making bispecific antibodies are known in the art. Traditional production of full-length bispecific antibodies is based on the coexpression of two immunoglobulin heavy chain-light chain pairs, where the two chains have different specificities (Millstein et al., 1983, Nature, 305:537-539). Because of the random assortment of immunoglobulin heavy and light chains, these hybridomas (quadromas) produce a potential mixture of different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., 1991, EMBO J., 10:3655-3659. A more directed approach is the generation of a Di-diabody a tetravalent bispecific antibody. Methods for producing a Di-diabody are known in the art (see e.g., Lu et al., 2003, J Immunol Methods 279:219-32; Marvin et al., 2005, Acta Pharmacolical Sinica 26:649).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when, the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., 1986, Methods in Enzymology, 121:210. According to another approach described in WO96/27011, a pair of antibody molecules can be engineered to maximize the percentage of heterodimers which are recovered from recombinant cell culture. The preferred interface comprises at least a part of the CH3 domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

For some uses, including in vivo use of antibodies in humans and in vitro detection assays, it may be preferable to use humanized antibodies or chimeric antibodies. Completely human antibodies and humanized antibodies are particularly desirable for therapeutic treatment of human subjects. Human antibodies can be made by a variety of methods known in the art including phage display methods described above using antibody libraries derived from human immunoglobulin sequences. See also U.S. Pat. Nos. 4,444,887 and 4,716,111; and International publication Nos. WO 98/46645, WO 98/50433, WO 98/24893, WO98/16654, WO 96/34096, WO 96/33735, and WO 91/10741.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g., International publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598. In addition, companies such as Abgenix, Inc. (Freemont, Calif.) and Genpharm (San Jose, Calif.) can be engaged to provide human antibodies directed against a selected antigen using technology similar to that described above.

A chimeric antibody is a molecule in which different portions of the antibody are derived from different immunoglobulin molecules. Methods for producing chimeric antibodies are known in the art. See e.g., Morrison, 1985, Science 229:1202; Oi et al., 1986, BioTechniques 4:214; Gillies et al., 1989, J. Immunol. Methods 125:191-202; and U.S. Pat. Nos. 5,807,715, 4,816,567, 4,816,397, and 6,311,415.

A humanized antibody is an antibody or its variant or fragment thereof which is capable of binding to a predetermined antigen and which comprises a framework region having substantially the amino acid sequence of a human immunoglobulin and a CDR having substantially the amino acid sequence of a non-human immunoglobulin. A humanized antibody comprises substantially all of at least one, and typically two, variable domains (Fab, Fab', F(ab').sub.2, Fabc, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. Ordinarily, the antibody will contain both the light chain as well as at least the variable domain of a heavy chain. The antibody also may include the CH1, hinge, CH2, CH3, and CH4 regions of the heavy chain. The humanized antibody can be selected from any class of immunoglobulins, including IgM, IgG, IgD, IgA and IgE, and any isotype, including IgG1, IgG2, IgG3 and IgG4. Usually the constant domain is a complement fixing constant domain where it is desired that the humanized antibody exhibit cytotoxic activity, and the class is typically IgG1. Where such cytotoxic activity is not desirable, the constant domain may be of the IgG2 class. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. Usually, at least 75% of the humanized antibody residues will correspond to those of the parental framework and CDR sequences, more often 90%, and most preferably greater than 95%. A humanized antibody can be produced using variety of techniques known in the art, including but not limited to, CDR-grafting (see e.g., European Patent No. EP 239,400; International Publication No. WO 91/09967; and U.S. Pat. Nos. 5,225,539, 5,530,101, and 5,585,089), veneering or resurfacing (see e.g., European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, PNAS 91:969-973), chain shuffling (see e.g., U.S. Pat. No. 5,565,332), and techniques disclosed in, e.g., U.S. Pat. No. 6,407,213, U.S. Pat. No. 5,766,886, International Publication No. WO 9317105, Tan et al., J. Immunol. 169:1119-25 (2002), Caldas et al., Protein Eng. 13(5):353-60 (2000), Morea et al., Methods 20(3):267-79 (2000), Baca et al., J. Biol. Chem. 272(16):10678-84 (1997), Roguska et al., Protein Eng. 9(10):895-904 (1996), Couto et al., Cancer Res. 55 (23 Supp):5973s-5977s (1995), Couto et al., Cancer Res. 55(8):1717-22 (1995), Sandhu J S, Gene 150(2):409-10

(1994), and Pedersen et al., J. Mol. Biol. 235(3):959-73 (1994). Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature 332:323.)

Further, the antibodies of the invention can, in turn, be utilized to generate anti-idiotype antibodies that "mimic" a receptor using techniques well known to those skilled in the art. (See, e.g., Greenspan & Bona, 1989, FASEB J. 7(5): 437-444; and Nissinoff, 1991, J. Immunol. 147(8): 2429-2438). For example, antibodies of the invention which bind to and competitively inhibit the binding of an receptor (as determined by assays well known in the art and disclosed infra) to its ligands can be used to generate anti-idiotypes that "mimic" the ligand and, as a consequence, bind to and neutralize the receptor and/or its ligands. Such neutralizing anti-idiotypes or Fab fragments of such anti-idiotypes can be used in therapeutic regimens to neutralize a ligand and/or its receptor. The invention provides methods employing the use of polynucleotides comprising a nucleotide sequence encoding an antibody of the invention or a fragment thereof.

The invention provides polynucleotides comprising a nucleotide sequence encoding an antibody or fragment thereof that specifically binds to an antigen and having one or more amino acid substitutes for improved therapeutic and/or formulation and/or manufacturing characteristics. The invention also encompasses polynucleotides that hybridize under high stringency, intermediate or lower stringency hybridization conditions to polynucleotides that encode an antibody of the invention.

The polynucleotides may be obtained, and the nucleotide sequence of the polynucleotides determined, by any method known in the art. The nucleotide sequence of antibodies specific for a desired antigen can be obtained, e.g., from the literature or a database such as GenBank. Nucleotide or alternatively, if the amino acid sequence of an antibody or fragment thereof that specifically binds to an antigen is known, the nucleotide sequences encoding the antibody or a fragment thereof (e.g., a CDR) can be determined using methods well known in the art, i.e., nucleotide codons known to encode particular amino acids are assembled in such a way to generate a nucleic acid that encodes the antibody. Such a polynucleotide encoding the antibody may be assembled from chemically synthesized oligonucleotides (e.g., as described in Kutmeier et al., 1994, BioTechniques 17:242), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Current Protocols in Molecular Biology, F. M. Ausubel et al., ed., John Wiley & Sons (Chichester, England, 1998); Molecular Cloning: A Laboratory Manual, 3rd Edition, J. Sambrook et al., ed., Cold Spring Harbor Laboratory Press (Cold Spring Harbor, N.Y., 2001); Antibodies: A Laboratory Manual, E. Harlow and D. Lane, ed., Cold Spring Harbor Laboratory Press (Cold Spring Harbor, N.Y., 1988); and Using Antibodies: A Laboratory Manual, E. Harlow and D. Lane, ed., Cold Spring Harbor Laboratory (Cold Spring Harbor, N.Y., 1999)), to generate antibodies having a different amino acid sequence, for example to create amino acid substitutions, deletions, and/or insertions.

In a specific embodiment, one or more of the CDRs is inserted within framework regions using routine recombinant DNA techniques. The framework regions may be naturally occurring or consensus framework regions, and preferably human framework regions (see, e.g., Chothia et al., 1998, J. Mol. Biol. 278: 457-479 for a listing of human framework regions). Preferably, the polynucleotide generated by the combination of the framework regions and CDRs encodes an antibody that specifically binds to a particular antigen. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

5.5. Generation of Antibody Domain Fusion Proteins Conjugates and Derivatives

As described above multidomain proteins include but are not limited to antibodies which also encompasses antibody-like and antibody-domain fusion proteins. An antibody-like molecule is any molecule that has been generated with a desired binding property, see, e.g., PCT Publication Nos. WO 04/044011; WO 04/058821; WO 04/003019 and WO 03/002609. Antibody-domain fusion proteins may incorporate one or more antibody domains or fragments thereof, such as the Fc domain or the variable domain with a fusion partner which in general can be an protein, including, but not limited to, a ligand, an enzyme, the ligand portion of a receptor, an adhesion protein, or some other protein or domain. For example, the heterologous polypeptides may be fused or conjugated to a Fab fragment, Fd fragment, Fv fragment, F(ab)2 fragment, a VH domain, a VL domain, a VH CDR, a VL CDR, or fragment thereof. A large number of antibody-domain molecules are known in the art including, but not limited to, diabodies (dsFv)2 (Bera et al., 1998, J. Mol. Biol. 281:475-83); minibodies (homodimers of scFv-CH3 fusion proteins) (Pessi et al., 1993, Nature 362:367-9), tetravalent di-diabody (Lu et al., 2003 J. Immunol. Methods 279:219-32), tetravalent bi-specific antibodies called Bs(scFv)4-IgG (Zuo et al., 2000, Protein Eng. 13:361-367) and Fc domain fusions (See, e.g., Chamow et al., 1996, Trends Biotechnol 14:52-60; Ashkenazi et al., 1997, Curr Opin Immunol 9:195-200; Heidaran et al., 1995, FASEB J. 9:140-5.).

In one embodiment, a multidomain comprises an antibody domain that binds to a molecule (i.e., target antigen) including, but not limited to, those disclosed herein (see Section 5.3) fused to a fusion partner. Fusion partners include, but are not limited to, peptides, polypeptides, proteins, small molecules, mimetic agents, synthetic drugs, inorganic molecules, and organic molecules. In one embodiment, a fusion partner is a polypeptide comprising at least 5, at least 10, at least 20, at least 30, at least 40, at least 50, at least 60, at least 70, at least 80, at least 90 or at least 100 contiguous amino acid residues, and is heterologous to the amino acid sequence of the antibody domain. In certain embodiments, said fusion partner is a bioactive molecule. The nucleotide sequences encoding a bioactive molecule may be obtained from any information available to those of skill in the art (i.e., from Genbank, the literature, or by routine cloning).

The fusion does not necessarily need to be direct, but may occur through linker sequences. Such linker molecules are commonly known in the art and described in Denardo et al., 1998, Clin Cancer Res 4:2483; Peterson et al., 1999, Bioconjug Chem 10:553; Zimmerman et al., 1999, Nucl Med Biol 26:943; Garnett, 2002, Adv Drug Deliv Rev 53:171. For example, antibody domains may be used to target heterologous polypeptides to particular cell types, either in vitro or in vivo, by fusing or conjugating the heterologous protein to antibodies domains specific for particular cell surface receptors. Antibody domains fused or conjugated to heterologous polypeptides may also be used in in vitro immunoassays and purification methods using methods known in the art. See e.g., International publication No. WO 93/21232; European Patent No. EP 439,095; Naramura et al., 1994, Immunol. Lett. 39:91-99; U.S. Pat. No. 5,474,981; Gillies et al., 1992, PNAS 89:1428-1432; and Fell et al., 1991, J. Immunol. 146:2446-2452.

Methods for fusing or conjugating polypeptides to antibody portions are well known in the art. See, e.g., U.S. Pat. Nos. 5,336,603, 5,783,181, 5,622,929, 5,359,046, 5,349,053, 5,447,851, 5,723,125, 5,908,626, 5,844,095, and 5,112,946; European Patent Nos. EP 307,434 and EP 367,166 and EP 394,827; PCT Publication Nos. WO 96/04388, WO 91/06570 WO 96/22024, WO 97/34631, and WO 99/04813; Ashkenazi et al., 1991, Proc. Natl. Acad. Sci. USA 88: 10535-10539; Traunecker et al., 1988, Nature, 331:84-86; Zheng et al., 1995, J. Immunol. 154:5590-5600; and Vil et al., 1992, Proc. Natl. Acad. Sci. USA 89:11337-11341.

Multidomain proteins (e.g., an antibody domain fusion protein) can be produced by standard recombinant DNA techniques or by protein synthetic techniques, e.g., by use of a peptide synthesizer. For example, a nucleic acid molecule encoding a multidomain protein (e.g., an antibody domain fusion protein) can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., Current Protocols in Molecular Biology, Ausubel et al., eds., John Wiley & Sons, 1992). The nucleotide sequence coding for a multidomain protein (e.g., an antibody domain fusion protein) can be inserted into an appropriate expression vector, i.e., a vector that contains the necessary elements for the transcription and translation of the inserted protein-coding sequence. A variety of host-vector systems may be utilized in the present invention to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

Additional fusion proteins, e.g., of antibody domains that specifically bind an antigen (e.g., supra), may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793; 5,811,238; 5,830,721; 5,834,252; and 5,837,458, and Patten et al., 1997, Curt Opinion Biotechnol. 8:724-33; Harayama, 1998, Trends Biotechnol. 16(2): 76-82; Hansson, et al., 1999, J. Mol. Biol. 287:265-76; and Lorenzo and Blasco, 1998, Biotechniques 24(2): 308-313. Antibodies or fragments thereof, or the encoded antibodies or fragments thereof, may be altered by being subjected to random mutagenesis by error-prone PCR, random nucleotide insertion or other methods prior to recombination. One or more portions of a polynucleotide encoding an antibody or antibody fragment, which portions specifically bind to an Antigen may be recombined with one or more components, motifs, sections, parts, domains, fragments, etc. of one or more heterologous molecules.

Moreover, antibodies or fragments thereof can be fused to marker sequences, such as a peptide to facilitate purification. In certain embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA 86:821-824, for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al., 1984, Cell 37:767) and the "flag" tag.

Antibodies and antibody domain fusion proteins include derivatives that are modified (i.e., by the covalent attachment of any type of molecule to an antibody or antibody domain fusion protein) such derivatives are collectively referred to herein as "antibody derivatives". For example, but not by way of limitation, the antibody derivatives include antibodies and antibody domain fusion proteins that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

Antibodies or antibody domain fusion proteins with increased in vivo half-lives can be generated by attaching to said antibodies or antibody domain fusion proteins, polymer molecules such as high molecular weight polyethyleneglycol (PEG). PEG can be attached to said antibodies or antibody domain fusion proteins with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

Further, antibodies or antibody domain fusion proteins can be conjugated to albumin in order to make them more stable in vivo or have a longer half life in vivo. The techniques are well known in the art, see e.g., International Publication Nos. WO 93/15199, WO 93/15200, and WO 01/77137; and European Patent No. EP 413, 622. The present invention encompasses the use of antibodies or antibody domain fusion proteins conjugated or fused to one or more moieties, including but not limited to, peptides, polypeptides, proteins, fusion proteins, nucleic acid molecules, small molecules, mimetic agents, synthetic drugs, inorganic molecules, and organic molecules.

In certain embodiments, antibody domains are conjugated to a diagnostic or detectable agent. Such multidomain proteins can be useful for monitoring or prognosing the development or progression of a cancer as part of a clinical testing procedure, such as determining the efficacy of a particular therapy. Such diagnosis and detection can be accomplished by coupling the antibody to detectable substances including, but not limited to various enzymes, such as but not limited to horseradish peroxidase, alkaline phosphatase, beta-galactosidase, or acetylcholinesterase; prosthetic groups, such as but not limited to streptavidin/biotin and avidin/biotin; fluorescent materials, such as but not limited to, umbelliferone, fluorescein, fluorescein isothiocynate, rhodamine, dichlorotriazinylamine fluorescein, dansyl chloride or phycoerythrin; luminescent materials, such as but not limited to, luminol; bioluminescent materials, such as but not limited to, luciferase, luciferin, and aequorin; radioactive materials, such as but not limited to iodine (131I, 125I, 123I, 121I,), carbon (14C), sulfur (35S), tritium (3H), indium (115In, 113In, 112In, 111In,), and technetium (99Tc), thallium (201Ti), gallium (68Ga, 67Ga), palladium (103Pd), molybdenum (99Mo), xenon (133Xe), fluorine (18F), 153Sm, 177Lu, 159Gd, 149Pm, 140La, 175Yb, 166Ho, 90Y, 47Sc, 186Re, 188Re, 142 Pr, 105Rh, 97Ru, 68Ge, 57Co, 65Zn, 85Sr, 32P, 153Gd, 169Yb, 51Cr, 54Mn, 75Se, 113Sn, and 117Tin; positron emitting metals using various positron emission tomographies, noradioactive paramagnetic metal ions, and molecules that are radiolabelled or conjugated to specific radioisotopes.

An antibody or an antibody domain may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells. Examples include ribonuclease, monomethylauristatin E and F, paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, epirubicin, and cyclophosphamide and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BCNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). A more extensive list of therapeutic moieties can be found in PCT publications WO 03/075957.

Further, an antibody or antibody domain may be conjugated to a therapeutic agent or drug moiety that modifies a given biological response. Therapeutic agents or drug moieties are not to be construed as limited to classical chemical therapeutic agents. For example, the drug moiety may be a protein or polypeptide possessing a desired biological activity. Such proteins may include, for example, a toxin such as abrin, ricin A, Onconase (or another cytotoxic RNase), pseudomonas exotoxin, cholera toxin, or diphtheria toxin; a protein such as tumor necrosis factor, α-interferon, β-interferon, nerve growth factor, platelet derived growth factor, tissue plasminogen activator, an apoptotic agent, e.g., TNF-α, TNF-β, AIM I (see, International Publication No. WO 97/33899), AIM II (see, International Publication No. WO 97/34911), Fas Ligand (Takahashi et al., 1994, J. Immunol., 6:1567), and VEGI (see, International Publication No. WO 99/23105), a thrombotic agent or an anti-angiogenic agent, e.g., angiostatin or endostatin; or, a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF")), or a growth factor (e.g., growth hormone ("GH")).

Moreover, an antibody can be conjugated to therapeutic moieties such as a radioactive materials or macrocyclic chelators useful for conjugating radiometal ions (see above for examples of radioactive materials). In certain embodiments, the macrocyclic chelator is 1,4,7,10-tetraazacyclododecane-N,N',N",N"-tetraacetic acid (DOTA) which can be attached to the antibody via a linker molecule. Such linker molecules are commonly known in the art and described in Denardo et al., 1998, Clin Cancer Res. 4:2483; Peterson et al., 1999, Bioconjug. Chem. 10:553; and Zimmerman et al., 1999, Nucl. Med. Biol. 26:943.

Techniques for conjugating therapeutic moieties to antibodies are well known. Moieties can be conjugated to antibodies by any method known in the art, including, but not limited to aldehyde/Schiff linkage, sulphydryl linkage, acid-labile linkage, cis-aconityl linkage, hydrazone linkage, enzymatically degradable linkage (see generally Garnett, 2002, Adv Drug Deliv Rev 53:171). Techniques for conjugating therapeutic moieties to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, Immunol. Rev. 62:119.

Alternatively, an antibody or antibody domain can be conjugated to a second antibody to form an antibody heteroconjugate as described by Segal in U.S. Pat. No. 4,676,980.

5.6. Production of Multidomain Proteins

Recombinant expression of a multidomain protein, derivative, analog or fragment thereof, (e.g., an antibody or fusion protein), requires construction of an expression vector containing a polynucleotide that encodes the multidomain protein (e.g., antibody, or fusion protein). Once a polynucleotide encoding a multidomain protein (e.g., antibody, or fusion protein) has been obtained, the vector for the production of the multidomain protein (e.g., antibody, or fusion protein) may be produced by recombinant DNA technology using techniques well known in the art. Thus, methods for preparing a protein by expressing a polynucleotide containing a multidomain protein (e.g., antibody, or fusion protein) encoding nucleotide sequence are described herein. Methods that are well known to those skilled in the art can be used to construct expression vectors containing multidomain protein (e.g., antibody, or fusion protein) coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding a multidomain protein of the invention, operably linked to a promoter. Such vectors may include the nucleotide sequence encoding the constant region of the antibody molecule (see, e.g., International Publication No. WO 86/05807; International Publication No. WO 89/01036; and U.S. Pat. No. 5,122,464) and the variable domain of the antibody, or a polypeptide for generating an multidomain protein may be cloned into such a vector for expression of the full length antibody chain (e.g. heavy or light chain), or complete multidomain protein comprising a fusion of a non-antibody derived polypeptide and a an antibody domain.

The expression vector is transferred to a host cell by conventional techniques and the transfected cells are then cultured by conventional techniques to produce a multidomain. Thus, the invention includes host cells containing a polynucleotide encoding a multidomain protein of the invention, operably linked to a heterologous promoter. In specific embodiments for the expression of multidomain proteins comprising double-chained antibodies, vectors encoding both the heavy and light chains may be co-expressed in the host cell for expression of the entire immunoglobulin molecule, as detailed below.

A variety of host-expression vector systems may be utilized to express the multidomain proteins of the invention (e.g., antibody or fusion protein molecules) (see, e.g., U.S. Pat. No. 5,807,715). Such host-expression systems represent vehicles by which the coding sequences of interest may be produced and subsequently purified, but also represent cells which may, when transformed or transfected with the appropriate nucleotide coding sequences, express an multidomain protein of the invention in situ. These include but are not limited to microorganisms such as bacteria (e.g., *E. coli* and *B. subtilis*) transformed with recombinant bacteriophage DNA, plasmid DNA or cosmid DNA expression vectors containing multidomain protein coding sequences; yeast (e.g., *Saccharomyces Pichia*) transformed with recombinant yeast expression vectors containing multidomain protein coding sequences; insect cell systems infected with recombinant virus expression vectors (e.g., baculovirus) containing multidomain protein coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing multidomain protein coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In certain embodiments, bacterial cells such as *Escherichia coli*, or eukaryotic cells, are used for the expression of a multidomain protein which is a recombinant antibody or fusion protein molecules. For example, mammalian cells such as Chinese hamster ovary cells (CHO), in conjunction with a vector such as the major intermediate early gene promoter element from human cytomegalovirus is an effective expression system for antibodies (Foecking et al., 1986, Gene 45:101; and Cockett et al., 1990, Bio/Technology 8:2). In a specific embodiment, the expression of nucleotide sequences encoding a multidomain protein of the invention (e.g., antibody or fusion protein) is regulated by a constitutive promoter, inducible promoter or tissue specific promoter.

In bacterial systems, a number of expression vectors may be advantageously selected depending upon the use intended for the multidomain protein (e.g., antibody or fusion protein) being expressed. For example, when a large quantity of such a protein is to be produced, for the generation of pharmaceutical compositions of a multidomain protein, vectors that direct the expression of high levels of fusion protein products that are readily purified may be desirable. Such vectors include, but are not limited to, the *E. coli* expression vector pUR278 (Ruther et al., 1983, EMBO 12:1791), in which the multidomain protein coding sequence may be ligated individually into the vector in frame with the lac Z coding region so that a lac Z-fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The multidomain protein (e.g., antibody or fusion protein) coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the multidomain protein (e.g., antibody or fusion protein) coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the multidomain protein (e.g., antibody or fusion protein) in infected hosts (e.g., see Logan & Shenk, 1984, Proc. Natl. Acad. Sci. USA 8 1:355-359). Specific initiation signals may also be required for efficient translation of inserted multidomain protein coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., 1987, Methods in Enzymol. 153:516-544).

The expression of a multidomain protein (e.g., antibody or fusion protein) may be controlled by any promoter or enhancer element known in the art. Promoters which may be used to control the expression of the gene encoding an multidomain protein (e.g., antibody or fusion protein) include, but are not limited to, the SV40 early promoter region (Bernoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42), the tetracycline (Tet) promoter (Gossen et al., 1995, Proc. Nat. Acad. Sci. USA 89:5547-5551); prokaryotic expression vectors such as the β-lactamase promoter (Villa-Kamaroff et al., 1978, Proc. Natl. Acad. Sci. U.S.A. 75:3727-3731), or the tac promoter (DeBoer et al., 1983, Proc. Natl. Acad. Sci. U.S.A. 80:21-25; see also "Useful proteins from recombinant bacteria" in Scientific American, 1980, 242:74-94); plant expression vectors comprising the nopaline synthetase promoter region (Herrera-Estrella et al., Nature 303:209-213) or the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286); neuronal-specific enolase (NSE) which is active in neuronal cells (Morelli et al., 1999, Gen. Virol. 80:571-83); brain-derived neurotrophic factor (BDNF) gene control region which is active in neuronal cells (Tabuchi et al., 1998, Biochem. Biophysic. Res. Corn. 253:818-823); glial fibrillary acidic protein (GFAP) promoter which is active in astrocytes (Gomes et al., 1999, Braz J Med Biol Res 32(5): 619-631; Morelli et al., 1999, Gen. Virol. 80:571-83) and gonadotropic releasing hormone gene control region which is active in the hypothalamus (Mason et al., 1986, Science 234:1372-1378).

Expression vectors containing inserts of a gene encoding a multidomain protein (e.g., antibody or fusion protein) can be identified by three general approaches: (a) nucleic acid hybridization, (b) presence or absence of "marker" gene functions, and (c) expression of inserted sequences. In the first approach, the presence of a gene encoding a peptide, polypeptide, protein or a fusion protein in an expression vector can be detected by nucleic acid hybridization using probes comprising sequences that are homologous to an inserted gene encoding the peptide, polypeptide, protein or the fusion protein, respectively. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a nucleotide sequence encoding a multidomain protein (e.g., antibody or fusion protein) in the vector. For example, if the nucleotide sequence encoding the multidomain protein (e.g., antibody or fusion protein) is inserted within the marker gene sequence of the vector, recombinants containing the gene encoding the multidomain protein (e.g., antibody or fusion protein) insert can be identified by the absence of the marker gene function. In the third approach, recombinant expression vectors can be identified by assaying the gene product (e.g., antibody or fusion protein) expressed by the recombinant. Such assays can be based, for example, on the physical or functional properties of the fusion protein in in vitro assay systems, e.g., binding with anti-bioactive molecule antibody.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered fusion protein may be controlled. Furthermore, different host cells have characteristic and specific mechanisms for the translational and post-translational processing and modification (e.g., glycosylation, phosphorylation of proteins). Appropriate cell lines or host systems can be chosen to ensure the desired modification and processing of the foreign protein expressed. For example, expression in a bacterial system will produce an unglycosylated product and expression in yeast will produce a glycosylated product. Eukaryotic host cells that possess the cellular machinery for proper processing of the primary transcript (e.g., glycosylation, and phosphorylation) of the gene product may be used. Such mammalian host cells include, but are not limited to, CHO, VERY, BHK, Hela, COS, MDCK, 293, 3T3, WI38, NS0, and in particular, neuronal cell lines such as, for example, SK-N-AS, SK-N-FI, SK-N-DZ human neuroblastomas (Sugimoto et al., 1984, J. Natl. Cancer Inst. 73: 51-57), SK-N-SH human neuroblastoma (Biochim. Biophys. Acta, 1982, 704: 450-460), Daoy human cerebellar medulloblastoma (He et al., 1992, Cancer Res. 52: 1144-1148) DBTRG- 05MG glioblastoma cells (Kruse et al., 1992, In Vitro Cell. Dev. Biol. 28A: 609-614), IMR-32 human neuroblastoma (Cancer Res., 195470, 30: 2110-2118), 1321N1 human astrocytoma (Proc. Natl Acad. Sci. USA, 1977, 74: 4816), MOG-G-CCM human astrocytoma (Br. J. Cancer, 1984, 49: 269), U87MG human glioblastoma-astrocytoma (Acta Pathol. Microbiol. Scand., 1968, 74: 465-486), A172 human glioblastoma (Olopade et al., 1992, Cancer Res. 52: 2523-2529), C6 rat glioma cells (Benda et al., 1968, Science 161: 370-371), Neuro-2a mouse neuroblastoma (Proc. Natl. Acad. Sci. USA, 1970, 65: 129-136), NB41A3 mouse neuroblastoma (Proc. Natl. Acad. Sci. USA, 1962, 48: 1184-1190), SCP sheep choroid plexus (Bolin et al., 1994, J. Virol. Methods 48: 211-221), G355-5, PG-4 Cat normal astrocyte (Haapala et al., 1985, J. Virol. 53: 827-833), Mpf ferret brain (Trowbridge et al., 1982, In Vitro 18: 952-960), and normal cell lines such as, for example, CTX TNA2 rat normal cortex brain (Radany et al., 1992, Proc. Natl. Acad. Sci. USA 89: 6467-6471) such as, for example, CRL7030 and Hs578Bst. Furthermore, different vector/host expression systems may effect processing reactions to different extents.

For long-term, high-yield production of recombinant proteins, stable expression is often preferred. For example, cell lines which stably express a multidomain protein of the invention (e.g., antibody or fusion protein) may be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci that in turn can be cloned and expanded into cell lines. This method may advantageously be used to engineer cell lines that express a multidomain protein that specifically binds to an antigen. Such engineered cell lines may be particularly useful in screening and evaluation of compounds that affect the activity of a multidomain protein (e.g., a polypeptide or a fusion protein) that specifically binds to an antigen.

A number of selection systems may be used, including but not limited to the herpes simplex virus thymidine kinase (Wigler et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy et al., 1980, Cell 22:817) genes can be employed in tk-, hgprt- or aprt-cells, respectively. Also, antimetabolite resistance can be used as the basis of selection for dhfr, which confers resistance to methotrexate (Wigler et al., 1980, Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147) genes.

Once an multidomain protein (e.g., antibody, or a fusion protein) has been produced by recombinant expression, it may be purified by any method known in the art for purification of a protein, for example, by chromatography (e.g., ion exchange, affinity, particularly by affinity for the specific antigen after Protein A, and sizing column chromatography), centrifugation, differential solubility, or by any other standard technique for the purification of proteins.

The expression levels of an multidomain protein (e.g., antibody or fusion protein) can be increased by vector amplification (for a review, see Bebbington and Hentschel, The use of vectors based on gene amplification for the expression of cloned genes in mammalian cells in DNA cloning, Vol. 3. (Academic Press, New York, 1987)). For example, when a marker in the vector system expressing a multidomain protein (e.g., antibody or fusion protein) is amplifiable, increase in the level of inhibitor present in culture of host cell will increase the number of copies of the marker gene. Since the amplified region is associated with the multidomain protein gene, production of the multidomain protein will also increase (Crouse et al., 1983, Mol. Cell. Biol. 3:257).

The host cell may be co-transfected with two expression vectors of the invention. For example, the first vector encoding a heavy chain derived polypeptide and the second vector encoding a light chain derived polypeptide. The two vectors may contain identical selectable markers, which enable equal expression of heavy and light chain polypeptides. Alternatively, a single vector may be used which encodes, and is capable of expressing, a fusion protein or both heavy and light chain polypeptides. The coding sequences for the fusion protein or heavy and light chains may comprise cDNA or genomic DNA.

5.7. Preparation of Liquid Formulations of Multidomain Proteins

The liquid formulations of multidomain proteins, such as antibodies, can be prepared using any method known in the art. In one embodiment, a liquid preparation can be prepared by a method comprising: purifying the multidomain proteins from conditioned medium (either single lots or pooled lots of medium) and concentrating a fraction of the purified multidomain proteins to a final concentration from about 15 mg/ml, about 20 mg/ml, about 30 mg/ml, about 40 mg/ml, about 50 mg/nil, about 60 mg/ml, about 70 mg/ml, about 80 mg/ml, about 90 mg/ml, about 100 mg/ml, about 110 mg/ml, about 125 mg/ml, about 150 mg/ml, about 200 mg/ml, about 250 mg/ml, or about 300 mg/ml.

In a specific embodiment, the liquid formulations can be prepared by a method comprising concentrating a fraction containing the purified antibody or a fragment to a final antibody or fragment concentration of from about 15 mg/ml, about 20 mg/ml, about 30 mg/ml, about 40 mg/ml, about 50 mg/ml, about 60 mg/ml, about 70 mg/ml, about 80 mg/ml, about 90 mg/ml, about 100 mg/ml, about 110 mg/ml, about 125 mg/ml, about 150 mg/ml, about 200 mg/ml, about 250 mg/ml, or about 300 mg/ml using a semipermeable membrane with an appropriate molecular weight (MW) cutoff (e.g., 30 kD cutoff for whole antibody molecules and F(ab')2 fragments; and 10 kD cutoff for antibody fragments, such as Fab fragments) and difiltrating the concentrated antibody fraction into the formulation buffer using the same membrane. Conditioned medium containing antibody or a fragment thereof that specifically binds to a target antigen is subjected to CUNO filtration and the filtered antibody is subjected to HS50 cation exchange chromatography. The fraction from the HS50 cation exchange chromatography is then subjected to rProtein A affinity chromatography followed by low pH treatment. Following low pH treatment, the antibody fraction is subject to super Q 650 anion exchange chromatography and then nanofiltration. The fraction of the antibody obtained after nanofiltration is then subjected to diafiltration to concentrate the antibody fraction into the formulation buffer using the same membrane.

The formulation buffer can comprise histidine at a concentration ranging from about 1 mM to about 100 mM, about 10 mM to about 50 mM, or about 20 mM to about 30 mM. The formulations may further comprise an amino acid at a concentration of less than 100 mM, less than 50 mM, less than 3.0 mM, less than 2.0 mM, or less than 1.8 mM. The amount of amino acid in the formulation should not cause a significant buffering in order to avoid multidomain protein precipitation at its isoelectric point. The pH of the formulation may range from about 5.0 to about 7.0, or about 5.5 to about 6.5, or about 5.8 to about 6.2, or about 6.0. To obtain an appropriate pH for a particular multidomain protein, it is generally understood that histidine (and glycine, if added) is first dissolved in water to obtain a buffer solution with higher pH than the desired pH and then the pH is brought down to the desired level by adding HCl. This way, the formation of inorganic salts (e.g., formation of NaCl when, for example, histidine hydrochloride is used as histidine and pH is raised to a desired level by adding NaOH) can be avoided.

The liquid formulations can be prepared as unit dosage forms by preparing a vial containing an aliquot of the liquid formulation for a one-time use. For example, a unit dosage per vial may contain 1 ml, 2 ml, 3 ml, 4 ml, 5 ml, 6 ml, 7 ml, 8 ml, 9 ml, 10 ml, 15 ml, or 20 ml of different concentrations of a multidomain protein ranging from about 15 mg/ml to about 300 mg/ml. If necessary, these preparations can be adjusted to a desired concentration by adding a sterile diluent to each vial. In a specific embodiment, the multidomain protein is an antibody that binds to a target antigen.

The liquid formulations of the present invention may be sterilized by various sterilization methods, including sterile filtration, radiation, etc. In a specific embodiment, the difiltrated antibody formulation is filter-sterilized with a presterilized 0.2 or 0.22-micron filter.

5.8. Preparation of Lyophilized Formulations of Multidomain Proteins

Lyophilization is a freeze drying process that is often used in the preparation of pharmaceutical products to preserve their biological activity. The liquid composition is prepared, then lyophilized to form a dry cake-like product. The process generally involves drying a previously frozen sample in a vacuum to remove the ice, leaving the non-water components intact, in the form of a powdery or cake-like substance. The lyophilized product can be stored for prolonged periods of time, and at elevated temperatures, without loss of biological activity, and can be readily reconstituted into a particle-free solution by the addition of an appropriate diluent. An appropriate diluent can be any liquid which is biologically acceptable and in which the lyophilized powder is completely soluble. Water, particularly sterile, pyrogen-free water, is a preferred diluent, since it does not include salts or other compounds which may affect the stability of the multidomain protein. The advantage of lyophilization is that the water content is reduced to a level that greatly reduce the various molecular events which lead to instability of the product upon long-term storage. The lyophilized product is also more readily able to withstand the physical stresses of shipping. The reconstituted product is preferably substantially particle free, thus it can be administered without prior filtration.

The following criteria are important in developing stable lyophilized protein products. Protein unfolding during lyophilization should be minimized. Various degradation pathways should be minimized. Residual moisture should be low.

A strong and elegant cake structure should be obtained. A reconstitution time 15 should be short, for example, less than 60 minutes, or less then 40 minutes, or less then 20 minutes, or less then 10 minutes, or less then 5 minutes, or less than 2 minutes, or less than 1 minute.

The protein in the pre-lyophilized formulation has a high concentration of at least 5 mg/ml, or at least 10 mg/ml, or at least 25 mg/ml, or at least 50 mg/ml or greater. The ph of the formulation may range from about 5.0 to about 7.0, or about 5.5 to about 6.5, or about 5.8 to about 6.2, or about 6. Examples of buffers that control the ph in this range include succinate (such as sodium succinate), gluconate, histidine, citrate and other organic acid buffers. Histidine is a preferred buffer for subcutaneous, intramuscular and peritoneal injection. A specific buffer contains about 5-30 mm histidine.

A surfactant may be added to the protein formulation. exemplary surfactants include nonionic surfactants such as polysorbates (e.g. polysorbates 20, 80, such as tween 20, 10 tween 80) or poloxamers (e.g. poloxamer 188). The amount of surfactant added is such that it reduces aggregation of the formulated protein and/or minimizes the formation of particulates in the formulation and/or reduces protein adsorption onto the container. The surfactant also reduces the reconstitution time of the lyophilized formulation. For example, the surfactant is present in the formulation in an amount from about 0.001% to about 0.5%, or from about 0.005% to about 0.1% or from about 0.01% to about 0.05%.

Lyophilized formulations may optional contain one or more of the following, an excipient, such as saccharides, polyols and sugar alcohols, a bulking agent that provides good lyophilized cake properties, such as serine, glycine, mannitol, and tonicity modifiers such as salts (e.g., NaCl, KCl, $MgCl_2$, $CaCl_2$).

5.9. Administration of Formulations of Multidomain Proteins

The formulated protein drug can be administered to a subject in an effective amount for treating or preventing a disease condition in the subject. The subject is preferably a mammal such as non-primate (e.g., cows, pigs, horses, cats, dogs, rats etc.) and a primate (e.g., monkey such as a cynomolgous monkey and a human). In a specific embodiment, the subject is a human.

Various delivery systems are known and can be used to administer the formulated drug. Methods of administering formulations include, but are not limited to, parenteral administration (e.g., intradermal, intramuscular, intraperitoneal, intravenous and subcutaneous), epidural administration, topical administration, pulmonary administration, and mucosal administration (e.g., intranasal and oral routes). In a specific embodiment, liquid formulations, including reconstituted lyophilized formulations, of a therapeutic protein are administered intramuscularly, intravenously, subcutaneously or, intramuscularly. The formulations may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can be employed, e.g., by use of an inhaler or nebulizer.

The formulation of the present invention can be packaged in a hermetically sealed container such as an ampoule or sachette indicating the quantity of multidomain protein. It is contemplated that the formulations of the present invention are in a hermetically sealed container indicating the quantity and concentration of multidomain protein. in certain embodiments, the formulation of the present invention is supplied in a hermetically sealed container at least 15 mg/ml, 20 mg/ml, 30 mg/ml, 40 mg/ml, 50 mg/ml, 60 mg/ml, 70 mg/ml, 80 mg/ml, 90 mg/ml, 100 mg/ml, 150 mg/ml, 200 mg/ml, 250 mg/ml, or 300 mg/ml, in a quantity of about 1 ml, 2 ml, 3 ml, 4 ml, 5 ml, 6 ml, 7 ml, 8 ml, 9 ml, 10 ml, 15 ml, or 20 ml.

The amount of the formulations of the present invention which will be effective in the treatment, prevention, management or amelioration of a disease, one or more symptoms thereof, or an undesirable condition associated with the disease, can be determined by standard clinical techniques. For example, the dosage of a drug formulation which will be effective in the treatment, prevention, management or amelioration of a disease can be determined by administering the formulation to an animal model (e.g., a cotton rat or monkey) and measuring the serum titer of the active protein, e.g., the serum titer of the multidomain protein. Accordingly, a dosage of the formulation that results in a serum titer of at least 1 µg/ml, at least 2 µg/ml, at least 5 µg/ml, at least 10 µg/ml, at least 20 µg/ml, at least 25 µg/ml, at least 35 µg/ml, at least 40 µg/ml, at least 50 µg/ml, at least 75 µg/ml, at least 100 µg/ml, at least 125 µg/ml, at least 150 µg/ml, at least 200 µg/ml, at least 250 µg/ml, at least 300 µg/ml, at least 350 µg/ml, at least 400 µg/ml, or at least 450 µg/ml can be administered to a human for the treatment, prevention, management or amelioration of a disease. In addition, in vitro assays may optionally be employed to help identify optimal dosage ranges. In specific embodiments, the multidomain protein is an antibody that bind to a target antigen.

The precise dose to be employed in the formulation will also depend on the route of administration, and the seriousness of the disease, and should be decided according to the judgment of the practitioner and each patient's circumstances. Effective doses may be extrapolated from dose-response curves derived from in vitro or animal model (e.g., the cotton rat or cynomolgous monkey) test systems.

For antibodies, proteins, polypeptides, peptides and fusion proteins, the dosage administered to a patient may be about 0.1 mg/kg to 30 mg/kg of the patients body weight. For example, generally, human antibodies have a longer half-life within the human body than antibodies from other species due to the immune response to the foreign polypeptides. Thus, lower dosages of human antibodies and less frequent administration is often possible. Further, the dosage, volume and frequency of administration of liquid formulations, including reconstituted lyophilized formulations, of the present invention may be reduced by increasing the concentration of an antibody or a fragment thereof in the formulations, increasing affinity and/or avidity of the antibody or a fragment thereof, and/or increasing the half-life of the antibody or a fragment thereof.

Exemplary doses of a small molecule include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram).

6. EXAMPLES

The following examples are presented by way of illustration of the present invention, and is not intended to limit the present invention in any way. In the examples, to show the structural relationships among the antibodies, a naming scheme illustrated in FIG. 23 is used. In the naming scheme, the first 3 characters identify the antigen binding domain: the capital letter designates the target, the lower case letter designates a particular epitope of the target, the number designates the variant of the antibody (for simplicity reasons, number 0 is often omitted). The last 4 characters identify the Fc domain: the first 3 characters identify the source and subclass of the Fc domain, the last lower case letter designates the Fc variant. The example in FIG. 23, Aa1-hG1a, thus identifies the "1" variant of an antibody that binds epitope "a" of target "A" and has variant "a" of a human gamma-1 (hG1) as its Fc domain. Such a naming scheme allows easy determination, e.g., that antibodies Aa-hG1 and Aa1-hG1 are different variants of an antibody that both bind to the same epitope of the same target and have the same Fc domain, or that antibodies Aa-hG1 and Ab-hG1 are different antibodies that bind to different epitopes of the same target and have the same Fc region, and so on.

6.1. Example 1

Contribution of Fab and Fc Domains to Tm Values and Stability

The Fab and Fc fragments of Ca-hG1 and Ba-hG1 were generated in order to learn more about the properties of the antibody Components. One long-term goal in studies of intact Mabs and their fragments is to understand the relationship between stability and structure. Currently it is known that Ca-hG1 is more stable with respect to aggregation when compared to Ba-hG1. This stability is further confirmed using the battery of analytical stability indicating assays. This stability difference offers an opportunity to compare properties of each antibody and to determine if there are measurable differences that can be exploited to understand the stability of these specific Mabs and more broadly applied to additional antibodies.

Fab and Fc domains were generated from full Mabs Ca-hG1 and Ba-hG1 using papain. A commercial kit from Pierce (Immunopure Fab Preparation Kit Pierce product #44885: Immunopure IgG Binding Buffer, Immunopure IgG Elution Buffer, Affinitypak Immobilized Protein A Column, Immobilized Papain, Cysteine Monohydrochloride, Phosphate Buffer, and Serum Separators) was used to digest the intact antibodies. Ca-hG1 was successfully digested using the method described in the kit. Ba-hG1 required an alternate chromatography step. For Ba-hG1, both the Fab and Fc bound to the protein A column. Purification of these components required anion exchange chromatography (Hitrap DEAE FF 5 ml—Amersham Product #17-5154-01). In addition to chromatography optimization, enzymology was optimized to achieve the best cleavage of the Mab in a reasonable time.

Fab and Fc domains were generated from Ca-hG1 using the following steps: A) adding antibody to papain and incubating overnight at 37° C., ~10 mg of IgG per digestion; B) separating crude digest from immobilized enzyme; C) applying digest to protein A column; D) eluting the Fab fragment in unretained fraction at pH-8.0; E) eluting the Fc fragment at pH-3.0; and F) dialyzing the fragments into a required buffer.

Fab and Fc domains were generated from Ba-hG1 using the above procedure with the following modification: Using double enzyme to Mab ratio, increasing agitation, increasing incubation time to 24 hrs, omitting protein A column, buffering exchange digested solution into equilibration buffer for DEAE column (Start Buffer: 10 mM NaCl, 10 mM Tris pH-7.8, Elution Buffer: 100 mM NaCl, 10 mM Tris pH-7.8). The Fab portion of the antibody was in the unretained fraction which was eluted during sample loading. The Fc fragment was eluted with the 100 mM NaCl buffer. Table 1 summarizes the Fab and Fc fragments obtained by the procedures.

TABLE 1

Fab And Fc Obtained

| Fragment | Ca-hG1 | Ba-hG1 |
|---|---|---|
| Fab | Purified | No Recovery |
| Fc | Purified | Fc + Fab Mix |

Differential Scanning Calorimetry (DSC) was used to examine the melting curve of the full length monoclonal antibody (Mab) Ca-hG1 (FIG. 1, Top). Deconvolution of the thermogram of the full length Mab reveals that at least three separate Tm values (Tm1=69° C., Tm2=83° C. And Tm3=87° C.) make up the curve (FIG. 2). Fab and Fc domain fragments were generated from Ca-hG1 and the purified fragments were analyzed individually by DSC (FIG. 1, bottom). The results show that individual Tm values in a full antibody may be assigned to individual domains with the largest peak generated by the Fab domain (FIG. 1 bottom, also see FIG. 10 bottom). Analysis of the peaks generated by the Fc domain indicate that the Tm of the $C_H2$ region is represented by the first peak in the Fc DSC profile and the Tm of the $C_H3$ region is represented by the second peak (FIG. 1 bottom, also see FIG. 10 bottom).

The reversibility of melting was examined at two different temperatures for the full length Ca-hG1 Mab (FIGS. 3 and 4), The Fab domain (FIGS. 5 and 6) and the Fc domain (FIGS. 7 and 8). The results show that instability of the full antibody is a result of the instability of the Fab domain.

The DSC profiles of an unrelated full length Mab, Ba-hG1, were also measured and compared to Ca-hG1 (FIG. 9). To determine which domain contributes the most to the differences in the Tm profile, The DSC profiles of the Fab and Fc domains of Ba-hG1 were determined individually. In FIG. 10, the top panel shows the DSC profile for the intact Ba-hG1 antibody and the bottom panel shows the profiles for the Fc and Fab domains. As was seen for Ca-hG1, the largest peak is generated by the melting of the Fab domain. As expected, the Fc region generated two smaller peaks which correspond to those seen for the identical Fe region isolated from Ca-hG1 (compare FIGS. 1 and 10, bottom panels). Deconvolution of the full antibody DSC profile indicates that at least three separate Tm values (Tm1=71° C., Tm2=82° C. And Tm3=93° C.) make up the curve of full length Ba-hG1 (FIG. 11). The reversibility of melting was examined for the full length Ba-hG1 Mab (FIGS. 12 and 13), The Fab domain (FIGS. 14 and 15) and the Fc domain (FIG. 16). The results also indicate that instability of the full antibody is a result of the instability of the Fab domain.

A comparison of the DSC profiles of Ba-hG1 and Ca-hG1 shows that the Fab domain contributes the most to the difference between the profiles for the two different Mab molecules (compare FIG. 1, bottom panel and FIG. 9, bottom panel). The results show that Ba-hG1 is less stable than Ca-hG1 because the Fab domain of Ba-hG1 is less stable than the Fab domain of Ca-hG1. Thus, the stability of an antibody may be predicted by evaluating the stability of the Fab domain.

6.2. Example 2

Examination of the Contribution of the Variable Domain to Tm and pI Values

Fab fragments from 6 individual antibodies, several of which recognize the same epitope (Ca-hG1, Ca1-hG1 and Ca1-hG1a) were isolated. The Tm and pI for each was determined. The Fab fragments from Ca-hG1 and Ca1-hG1 differ by only about 13 amino acids, while Ca1-hG1 and Ca1-hG1a differ by only 3 amino acids. These three highly related molecules show only small differences in their pI and Tm values. In contrast, the completely unrelated molecules, Aa-hG1, Ba-hG1 and Da-hG1, show very different profiles (FIG. 17).

Figure 18A:
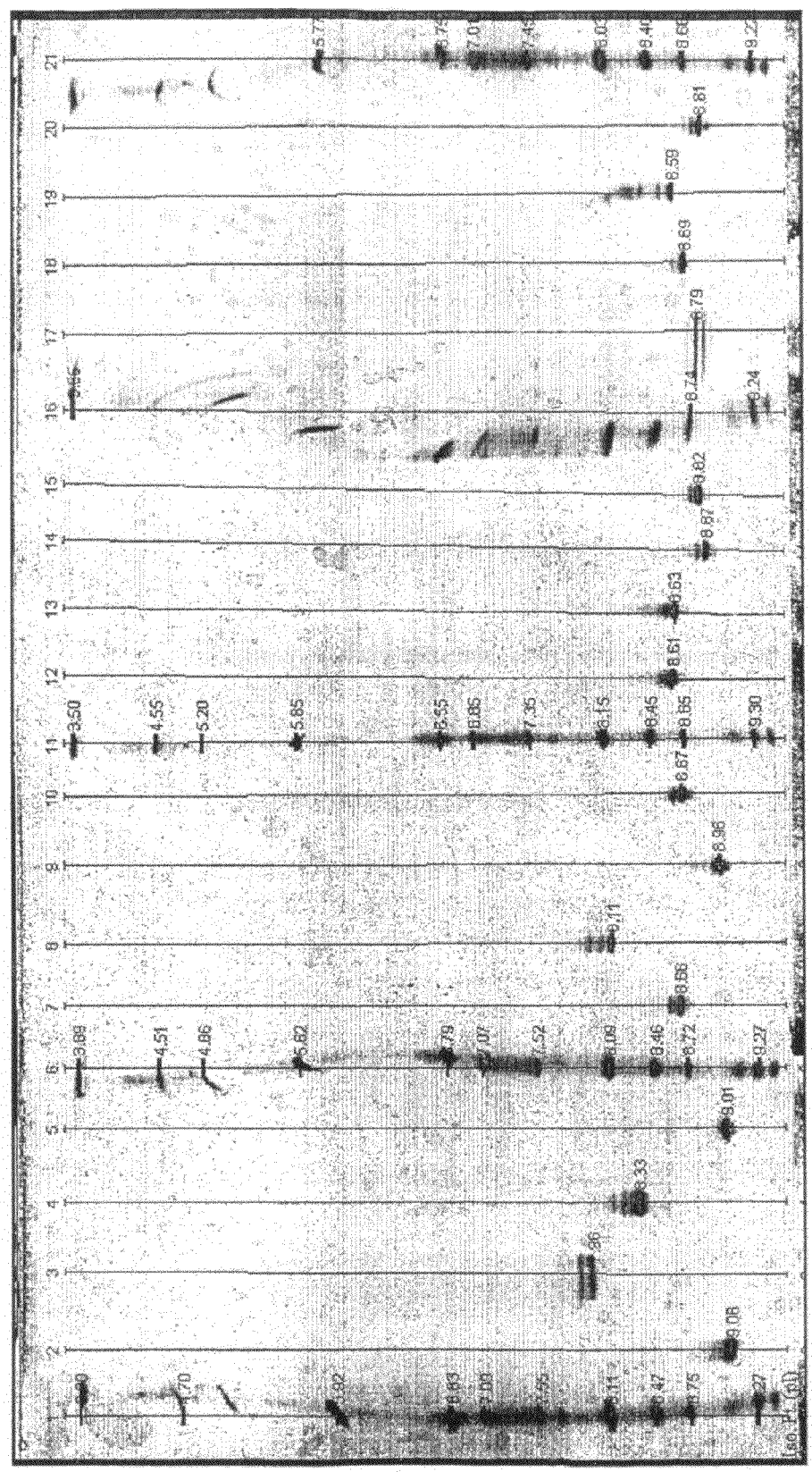
Figure 18B:
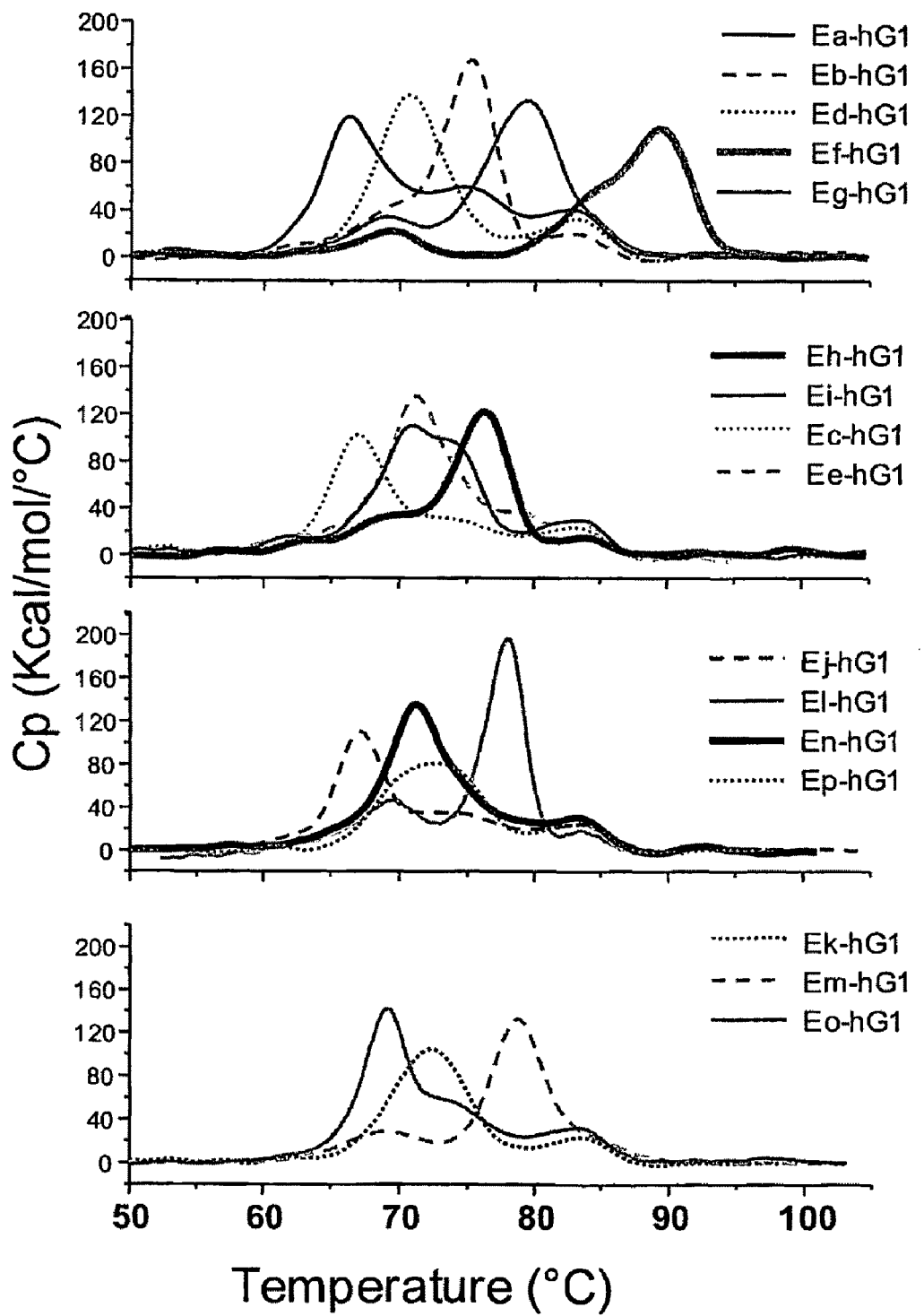
Figure 18C:
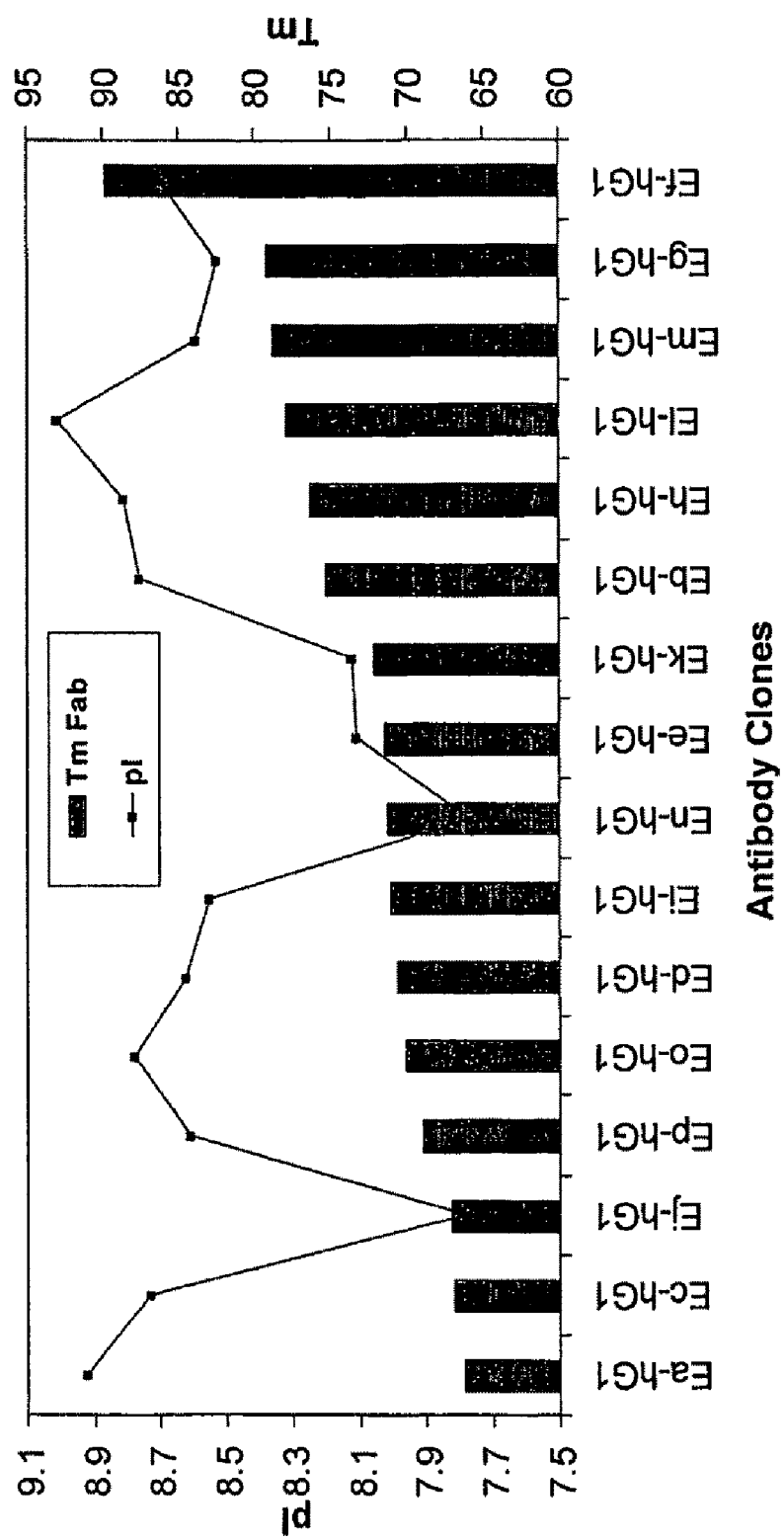

To examine the contribution of the Fab region to Tm and pI values in the context of a full length antibody, 18 individual Fab clones isolated from a single phage display library were converted into full length IgG1 and purified from transient transfections. These molecules differ only in their variable regions. The subsequent analysis of these clones demonstrate that they have a wide range of characteristics. For example, they exhibit dissociation constants (Kd) between a high of about 330 nM to a low of just 22 nM (data not shown). The Tm values of the Fab fragments, determined by DSC analysis of the intact antibodies, range from a low of just about 70° C. to a high of about 90° C. (FIGS. 18B and 18C). pI values of the intact antibodies also showed a wide range with the antibodies having pI values from 7.8-9.0 (FIGS. 18A and 18C).

FIG. 19 shows Tm and pI values of an additional panel of antibodies that bind to a variety of different epitopes present on a single protein as well as the previously analyzed Ca1-hG1 and two chimeric antibodies (Ha-hG1, Ia-hG1) generated by combining the heavy and light chains from two different antibodies. These antibodies also have a common Fc domain and vary only in their Fab domains. As was seen above, the different Fab domains result in a wide range of both pI and Tm values. In contrast, FIG. 20 shows the Tm and pI values of a panel of antibodies which differ by only a few amino acids in the hinge domain. These hinge variants, which have identical Fab domains, vary little in either their pI or Tm. Note that for the hinge variants for which a pI was determined, the amino acid changes made did not alter the net charge based on amino acid sequence.

FIG. 21 shows the viscosities of a 100 mg/mL solution of Ca-hG1, Ca1-hG1, Ba-hG1 and Da-hG1 as a function of temperature. It can be seen that the antibody with the lowest pI, Da-hG1, had the highest viscosity under the conditions measured. Also shown is the viscosity of Ba-hG1 as a function of temperature at increasing concentrations (100, 126, 138 and 150 mg/mL). The higher the concentration the higher the viscosity of the antibody solution. Accordingly, for the formulation of high concentration liquid formulations it is generally desirable to use an antibody with a lower inherent viscosity. These studies indicate that the pI of an antibody provides a measure indicative of the viscosity of the antibody in solution.

Figure 22A:
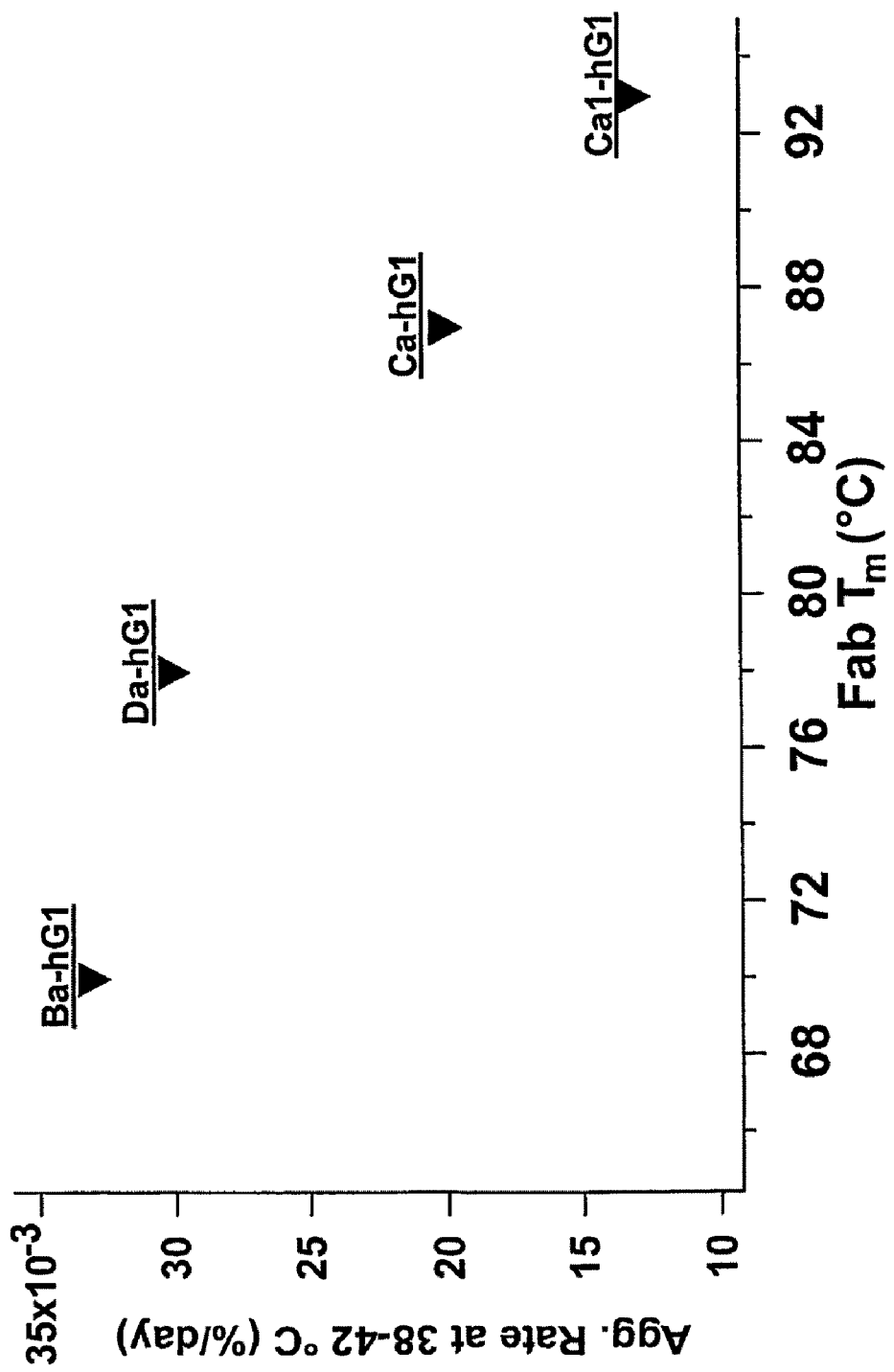

FIG. 22A shows the aggregation rates of the Ba-hG1, Ca-hG1, Ca1-hG1 and Da-hG1 antibodies at ~40° C. as a function of the Tm of the Fab. It can be seen that the aggregation rate increases for antibodies having a lower Fab Tm. As shown in Table 2 this trend is also consistent for these molecules when stored at room temperature (25° C.) and 5° C. These results indicate that increased Fab Tm values correlate with reduced aggregation rates over a wide temperature range. Two of these antibodies, Ba-hG1 and Ca-hG1, were chosen for further analysis.

Figure 22B:
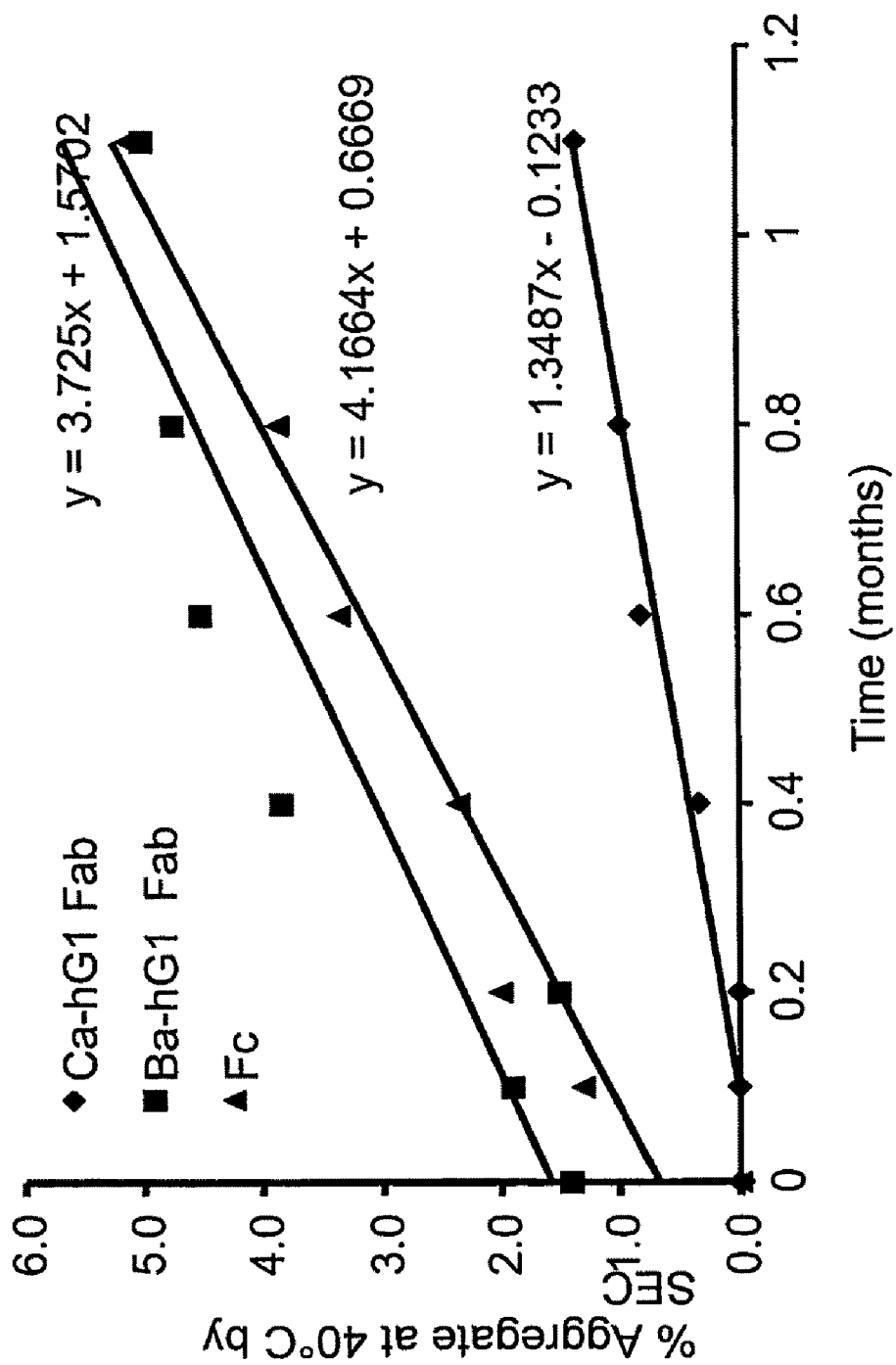

The Fab and Fc fragments of Ba-hG1 and Ca-hG1 were isolated and the stability at 40° C. of each fragment was examined. FIG. 22B shows the aggregation profiles of the Fab and Fc fragments of Ba-hG1 and Ca-hG1 over time at 40° C. The ratio of the aggregation rates of both the Fab fragments and the full length Mabs are shown in Table 2. The ratio for the Fab fragments (Ba-hG1/Ca-hG1) is about 2.8 which is similar to ratio of the aggregation rates for the intact antibodies, about 2.4 (see Table 2). The aggregation rate of the Fc region is similar to that seen for the Ba-hG1 Fab fragment. Together these data indicate that the Fab domain plays a significant role in the formation of aggregates in the intact antibodies and that the aggregation rate of the intact antibody is influenced by the Tm of the Fab domain. Furthermore, these data also indicate that an increase in the Tm of the Fab region reduced the tendency for an antibody to aggregate over time and results in a more stable molecule. Accordingly, rapid screening by heating a cooling cycles using DSC can be used as a measure for the propensity of and antibody to form aggregate upon storage.

TABLE 2

Aggregation Rates
Aggregation Rate (% aggregate/month)

| MAb | 20° C. | 5° C. | 40° C. | | Ratio |
|---|---|---|---|---|---|
| Ba-hG1 | 0.19 | 0.06 | Fab of Ba-hG1 to Fab of Ca-hG1 | | 2.8 |
| Da-hG1 | 0.25 | 0.04 | Mab of Ba-hG1 to Mab of Ca-hG1 | | 2.4 |
| Ca-hG1 | 0.08 | 0.01 | | | |
| Ca1-hG1 | 0.06 | 0.02 | | | |

These results show that antibodies with various preferred characteristics can be screened using relevant in vitro and in vivo studies to determine the most desirable combination of characteristics. For example, for targeting a particular target, e.g., target "E", a panel of antibodies that bind different antigens of the target, have different Tm values, and different pI values may be screened to obtain one or more that have desired combinations of these characteristics.

6.3. Example 3

Examination of the Contribution of the Fc Hinge Region to Tm and pI Values

A number of different mutations were generated in the hinge region of the antibody Fa6-hG1. The Tm of the Fab domain of the parental antibody and each hinge mutant was determined by DSC analysis of the intact antibodies (FIG. 20). In addition, the pI values of the parent and several of the mutants were determined (FIG. 20). Note that for the hinge variants for which a pI was determined, the amino acid changes made did not alter the net charge based on amino acid sequence and as expected has little effect on the pI. In addition, the Tm values for these closely related molecules are nearly identical indicating that the sequence of hinge has little influence on the Tm of the Fab.

6.4. Example 4

Engineering the Fc Domain to Alter the pI

A series of amino acid residue substitutions were generated in the Fc domain (human IgG1) of an anti-IL9 antibody to raise or lower the isoelectric point (pI). The substitutions were selected to have minimal impact on effector functions such as antibody-dependent cell-mediated cytotoxicity (ADCC) and complement-dependent cytotoxicity (CDC). The substitutions were also chosen to prevent disruption of the binding sites for protein A (a protein used for antibody purification) and FcRn (a receptor that mediates IgG homeostasis). Using the crystal structure of the human Fc as a guide, residues in the following regions: 339-375 and 390-414 (using the EU numbering scheme as described in Kabat et al., 1991, NIH Publication 91-3242, National Technical Information Service, Springfield, Va.) were selected for substitution. Within these regions, prolines were excluded as possible sites for substitution because of the likelihood that prolines are necessary to maintain the protein fold. Ribbon diagrams of the human Fc CH2-CH3 regions are shown in FIGS. 24 and 25. The red indicates a region where mutations may affect C1q, FcγR, FcRn, and protein A binding, the blue indicates a region where substitutions may affect FcγR and FcRn binding, and the green indicates a region where substitutions may affect FcRn and protein A binding. The yellow region is where the two CH3 domains pack against each other. The location of the residues selected for substitution are indicated in pink and are space filled.

The pI of a protein is defined as the pH at which the protein carries no net charge. At a pH below the protein's pI, the protein carries a net positive charge and at a pH above the protein's pI the protein carries a net negative charge. The acidic amino acids aspartic acid (D) and glutamic acid (E) are deprotonated at or near physiological pH and carry a negative charge. The basic amino acids lysine (K) and arginine (R) are protonated at or near physiological pH and carry a positive charge. At each amino acid residue of a protein, there are two possible changes that can be made: charged residues can be changed to uncharged residues or residues with the opposite charge and uncharged residues can be changed to residues with either a positive or negative charge. The maximum change in charge that can occur is where an amino acid is substituted with another amino acid of opposite charge. Replacing a charged residue with an uncharged residue serves only to remove charge, not add opposite charge and is less effective than replacing a charged residue with one of opposite charge. Substitutions of D and E with either K or R, or vice versa, are likely to have the greatest impact on pI. When choosing what residue should substitute for a given residue in the wild type sequence, the MHC type II immunogenicity of the new residue was checked using the website: http://www.syfpeithi.de/scripts/MHCServer.dll/home.htm. It was discovered that introducing a polar uncharged residue for a charged residue was less likely to be immunogenic than introducing a nonpolar residue for a charged residue.

Five sites were initially chosen for substitution, K340, E345, R355, Q362, and D401 (FIG. 24). Site-directed mutagenesis was performed on the anti-IL9 antibody using a Stratagene QuikChange II XL kit. The modified antibodies were produced in 293H cells and purified using protein A. Isoelectric focusing gels (IEF) were run to determine the pI changes. The IEF gels are shown FIGS. 26 and 27 and the pI values and net changes are summarized in Table 3. The trend for pI changes was as expected. The wild type produced in 293H cells was used as a basis for comparison in FIGS. 26 and 27. The pI of wild type produced in NSO cells was found to be nearly identical to that seen for antibody produced in 293H cells (FIG. 27, compare lanes 1 and 2). K340E had a lower pI than K340Q and both of these were lower than the pI of the wild type. The same pattern was observed for R355E and R355Q. E345K had a higher pI than E345Q and both of these mutants had a higher pI than wild type. This same pattern was also observed for D401K and D401N. Replacement of the residue Q362, which does not carry a charge, with E lowered the pI and replacement of the residue Q362 with K increased the pI. The largest magnitude change that lowered the pI was −0.62, R355E, and the largest magnitude change that increased the pI was 0.47, E345K.

After analyzing that data on the single substitutions, combinatorial substitutions were made. As expected, combinatorial substitutions had a greater impact on pI than single mutations alone (FIG. 27 and Table 3). The K340E R355E double substitutions showed a larger decrease in charge than the R355E Q362E double substitutions (−1.03 and −0.82, respectively). This decrease resulted from the switching in charge of two residues while in the R355E Q362E double substitution only the residue R355 was switched to its opposite charge. Both the E345K D401N and E345K D401K double substitution gave a greater magnitude increase in pI than any of the single mutations (0.68 and 0.62, respectively), although switching the charge of both residues didn't result in a greater increase in the pI. Their pIs fall very close to each other and are probably within the experimental error of the gel (note the smearing of the band in FIG. 27). The K340E R355E Q362E and K340Q R355E Q362E triple substitutions followed the expected pattern and had the largest pI decreases of any of the substitutions. The E345K Q362K D401K and E345K Q362K D401N triple substitutions ran off the gel shown in FIG. 27 which suggested that their pIs were largely increased.

Several additional sites for substitution, G341, Q342, R344, E356, M358, T359, N361, L365, N390, L398, and K409, were also chosen (FIG. 25). The pI could not be determined for the M358K substitution because the proteins were too faint to make a clear determination. The change in pI for the remaining substitutions followed the same trends as was seen for the first set of single substitutions (FIG. 28 and Table 3). These data demonstrate that targeted substitutions within the Fc domain are useful for engineering the pI of an antibody. In addition, these data indicate that targeted substitutions will prove useful for engineering the pI of other therapeutic molecules such as Fc fusion proteins.

Differential Scanning Calorimetry (DSC) was used to examine the melting curves of the single and triple substitutions to examine the effect of each substitution on the Tm of the substituted antibodies. The E345Q, E345K, R355Q, R335E, Q362E and Q362K substitutions have similar Tm profiles as wild type (FIG. 30, left panel), while the K340Q, K340E and D401K substitutions resulted in altered Tm profiles (FIG. 30, right panel). The triple substitutions, which both contain a substitution at position D401, show a similar alteration in Tm profiles as the single substitution D401K (compare FIG. 30, left panel and FIG. 31). These results indicate that substitutions may be selected to both engineer the pI and the Tm of protein domains such as, for example, the Fc domain.

TABLE 3

Isoelectric points of single, double, and triple mutants.

| Name | pI | pI Change from WT | Charge Change from WT |
|---|---|---|---|
| Wild Type | 8.15 | 0 | 0 |
| K340Q | 7.88 | −0.27 | −1 |
| K340E | 7.57 | −0.58 | −2 |
| E345Q | 8.37 | 0.22 | 1 |
| E345K | 8.62 | 0.47 | 2 |
| R355Q | 7.79 | −0.36 | −1 |
| R355E | 7.53 | −0.62 | −2 |
| Q362E | 7.83 | −0.32 | −1 |
| Q362K | 8.36 | 0.21 | 1 |
| D401N | 8.34 | 0.19 | 1 |
| D401K | 8.49 | 0.34 | 2 |
| K340E R355E | 7.12 | −1.03 | −4 |
| R355E Q362E | 7.33 | −0.82 | −3 |
| E345K D401N | 8.83 | 0.68 | 3 |
| E345K D401K | 8.77 | 0.62 | 4 |
| K340E R355E Q362E | 6.80 | −1.35 | −5 |
| K340Q R355E Q362E | 6.99 | −1.16 | −4 |
| E345K Q362K D401K | ND¥ | ND¥ | 5 |
| E345K Q362K D401N | ND¥ | ND¥ | 4 |

TABLE 3-continued

Isoelectric points of single, double, and triple mutants.

| Name | pI | pI Change from WT | Charge Change from WT |
|---|---|---|---|
| Q342E | 7.88 | −0.27 | −1 |
| Q342K | 8.32 | 0.17 | 1 |
| R344Q | 7.90 | −0.25 | −1 |
| R344E | 7.66 | −0.49 | −2 |
| E356Q | 8.31 | 0.16 | 1 |
| E356K | 8.59 | 0.44 | 2 |
| L365E[a] | 8.20 | 0.05 | −1 |
| L365K[a] | 8.22 | 0.07 | 1 |
| L398E | 7.92 | −0.23 | −1 |
| L398K | 8.31 | 0.16 | 1 |
| K409Q[a] | 7.93 | −0.22 | −1 |
| K409E[a] | 7.77 | −0.38 | −2 |
| G341D | 7.97 | −0.18 | −1 |
| G341K | 8.45 | 0.3 | +1 |
| M358E | 7.95 | −0.2 | −1 |
| M358K | ND‡ | ND‡ | +1 |
| T359E | 7.94 | −0.21 | −1 |
| T359K | 8.45 | 0.3 | +1 |
| N361D | 7.90 | −0.25 | −1 |
| N361K | 8.44 | 0.29 | +1 |
| N390D | 7.90 | −0.25 | −1 |
| N390K | 8.39 | 0.24 | +1 |
| E345KQ362K | 8.73 | 0.58 | +3 |

[a]this position is a buried residue
ND¥ indicates that the value could not be determined using the present IEF gel method likely equal to or more than 9.0
ND‡ indicates that the value could not be determined because the proteins did not run clearly on the gel or was too faint

6.5. Example 5 pI and Tm Analysis for Candidate Selection

Two variants of an antibody, designated Fa-hG1, were generated for consideration as clinical candidates. For ease of administration high concentration liquid formulations are desired. The first variant, designated Fa-hG1b, was generated by making several substitutions in the Fc region of the molecule, one of which (L235E) reduces the charge by 1.0 and is expected to modestly reduced the pI (see Example 4 above). The second variant, designated Fa-hG4a, was generated by replacing the human IgG1 Fc region with a human IgG4 Fc region and engineering several substitutions including L235E. Based on amino acid sequence analysis Fa-hG4a will have a charge change of −4 compared to the wild type antibody. The three antibodies were analyzed to determine their Tm and pI values.

The DSC profiles of each antibody are shown overlaid in FIG. 32. As described above, the Tm of the largest peak is used as the Tm of the Fab domain. The Tm of the Fab domain of the parental antibody was seen to be 70.4° C. and the Tm of the Fa-hG4a and Fa-hG1b variants was 70.4° C. and 70.9° C., respectively. These data demonstrate that the alterations of the Fc region did not change the major Tm peak of the Fab region. However, the DSC profile of Fa-hG4a dropped off dramatically above ~71° C. indicating that this antibody may have precipitated due to instability introduced by the addition of the variant IgG4 Fc region.

Isoelectric focusing gels (IEF) were run to determine the pI of each antibody. The wild type antibody had a pI of ~8.35 (position of the major protein peak in FIG. 33). The Fa-hG1b variant showed a modest reduction to ~8.18 while the pI of Fa-hG4a was significantly reduced to ~7.13 (FIG. 33). The reduction in pI seen for the Fa-hG1b variant is in agreement with the change in pI seen for similar substitutions (see Table 3). The Fa-hG4a variant had a net pI change of −1.22 and a total charge change of −4 which is also in agreement with the change in pI seen for similar substitutions (see Table 3).

For selection of a clinical candidate, both the Tm and the pI of the antibody are taken into account. In this case, although the Tm of the Fab domain for each of the variants differed by less then 0.5° C., the DSC profile of the Fa-hG4a antibody indicated that this variant may be subject to some additional instability. Analysis of the pI revealed that the Fa-hG4a variant had a relatively low pI (~7.13). Accordingly, based on the correlation of low pI with increased viscosity and the potential instability revealed by DSC analysis of the Fa-hG4a variant, the Fa-hG1b variant was selected as a clinical candidate.

6.6. Methods

Isoelectric Focusing Gel Electrophoresis: Isoelectric points were determined using a Pharmacia Biotech Multiphor 2 electrophoresis system with a multi temp 3 refrigerated bath recirculation unit and an EPS 3501 XL power supply. Pre-cast ampholine gels (Amersham Biosciences, pI range 2.5-10 or pI range 3.5-9.5) were loaded with 5-8 μg of protein. Protein samples were dialyzed in 10 mM Histidine pH-6 before loading on the gel as required. Broad range pI marker standards (Amersham, pI range 3-10, 8 μL) were used to determine relative pI for the Mabs. Electrophoresis was performed at 1500 V, 50 mA for 105 minutes. The gel was fixed using a Sigma fixing solution (5×) diluted with purified water to 1×. Staining was performed overnight at room temperature using Simply Blue stain (Invitrogen). Destaining was carried out with a solution that consisted of 25% ethanol, 8% acetic acid and 67% purified water. Isoelectric points were determined using a Bio-Rad's GS-800 calibrated densitometer relative to calibration curves of the standards.

Differential Scanning Calorimetry: Thermal melting temperatures (Tm) were measured with a VP-DSC (MicroCal, LLC) using a scan rate of 1.0° C./min and a temperature range of 25-120° C. A filter period of 8 seconds was used along with a 5-15 minute pre-scan thermostating. Samples were prepared by dialysis into 10 mM Histidine-HCl, pH 6 using Pierce dialysis cups (3.5 kD). Average Mab concentrations were 50 μg/mL to 790 μg/mL as determined by A280. Melting temperatures were determined following manufacturer procedures using Origin software supplied with the system. Briefly, multiple baselines were run with buffer in both the sample and reference cell to establish thermal equilibrium. After the baseline was subtracted from the sample thermogram, the data were concentration normalized and fitted using the deconvolution function.

Viscosity determination: Viscosity of mAB solutions were performed using a ViscoLab 4000 Viscometer System (Cambridge Applied Systems) equipped with a ViscoLab Piston (SN:7497, 0.3055", 1-20 cP) and S6S Reference Standard (Koehler Instrument Company, Inc.). The viscometer was connected to a water bath and the system equilibrated to 20° C. Piston was checked using S6S viscosity reference standard (8.530 cP @20.00° C.). Check piston was also checked using RODI H2O (1.00 cP @20.0° C.). The piston was cleaned and rinsed thoroughly with soap and water between measurements of each different solution type. The system was then cooled to ≦2° C. When the system temperature was at or below 2° C., sample was loaded into the chamber and the piston was lowered into the sample. After sample was equilibrated to the temperature of the chamber, measurement was initiated. The temperature was increased at 1° C. increments every 7-10 minutes to a final temperature of ≧25° C. The temperature was adjusted on the water bath but the recorded temperature was what was displayed on the viscometer. The viscosity result was recorded immediately prior to increasing the temperature. The piston remained in motion during measurements to minimize the need for re-equilibration.

Site Directed Mutagenesis: mutagenesis was performed according to the manufacturer's instructions using a Stratagene QuikChange II XL kit and the primers listed in Table 4.

TABLE 4

Primers used for site directed mutagenesis

| Primer | Sequence‡ | SEQ ID NO. |
|---|---|---|
| K340Q-F | CCATCTCCAAAGCCCAGGGGCAGCCCCGAGAACC | 1 |
| K340Q-R | GGTTCTCGGGGCTGCCCCTGGGCTTTGGAGATGG | 2 |
| K340E-F | CCATCTCCAAAGCCGAGGGGCAGCCCCGAGAACC | 3 |
| K340E-R | GGTTCTCGGGGCTGCCCCTCGGCTTTGGAGATGG | 4 |
| E345Q-F | GCCAAAGGGCAGCCCCGACAGCCACAGGTGTACACCC | 5 |
| E345Q-R | GGGTGTACACCTGTGGCTGTCGGGGCTGCCCTTTGGC | 6 |
| E345K-F | GCCAAAGGGCAGCCCCGAAAGCCACAGGTGTACACCC | 7 |
| E345K-R | GGGTGTACACCTGTGGCTTTCGGGGCTGCCCTTTGGC | 8 |
| R355Q-F | CCCTGCGCCCATCCCAGGAGGAGATGACCAAGAACC | 9 |
| R355Q-R | GGTTCTTGGTCATCTCCTCCTGGGATGGGGCAGGG | 10 |
| R355E-F | CCCTGCCCCATCCGAGGAGGAGATGACCAAGAACC | 11 |
| R355E-R | GGTTCTTGGTCATCTCCTCCTCGGATGGGGCAGGG | 12 |
| Q362E-F | GGAGATGACCAAGAACGAGGTCAGCCTGACCTGCC | 13 |
| Q362E-R | CCAGGCAGGTCAGGCTGACCTCGTTCTTGGTCATCTCC | 14 |
| Q362K-F | GGAGATGACCAAGAACAAGGTCAGCCTGACCTGCC | 15 |

TABLE 4-continued

Primers used for site directed mutagenesis

| Primer | Sequence‡ | SEQ ID NO. |
|---|---|---|
| Q362K-R | CCAGGCAGGTCAGGCTGACCTTGTTCTTGGTCATCTCC | 16 |
| D401N-F | CGCCTCCCGTGCTGGACTCCAACGGCTCCTTCTTCC | 17 |
| D401N-R | GGAAGAAGGAGCCGTTGGAGTCCAGCACGGGAGGCG | 18 |
| D401K-F | CGCCTCCCGTGCTGGACTCCAAGGGCTCCTTCTTCC | 19 |
| D401K-R | GGAAGAAGGAGCCCTTGGAGTCCAGCACGGGAGGCG | 20 |
| L365E-for | GACCAAGAACCAGGTCAGCGAGACCTGCCTGGTCAAAGGC | 21 |
| L365E-rev | GCCTTTGACCAGGCAGGTCTCGCTGACCTGGTTCTTGGTC | 22 |
| L365K-for | GACCAAGAACCAGGTCAGCAAGACCTGCCTGGTCAAAGGC | 23 |
| L365K-rev | GCCTTTGACCAGGCAGGTCTTGCTGACCTGGTTCTTGGTC | 24 |
| K409Q-for | GCTCCTTCTTCCTCTATAGCCAGCTCACCGTGGACAAGAGC | 25 |
| K409Q-rev | GCTCTTGTCCACGGTGAGCTGGCTATAGAGGAAGAAGGAGC | 26 |
| K409E-for | GCTCCTTCTTCCTCTATAGCGAGCTCACCGTGGACAAGAGC | 27 |
| K409E-rev | GCTCTTGTCCACGGTGAGCTCGCTATAGAGGAAGAAGGAGC | 28 |
| Q342E-for | CCATCTCCAAAGCCAAAGGGGAGCCCCGAGAACCACAGGTG | 29 |
| Q342E-rev | CACCTGTGGTTCTCGGGGCTCCCCTTTGGCTTTGGAGATGG | 30 |
| Q342K-for | CCATCTCCAAAGCCAAAGGGAAGCCCCGAGAACCACAGGTG | 31 |
| Q342K-rev | CACCTGTGGTTCTCGGGGCTTCCCTTTGGCTTTGGAGATGG | 32 |
| R344Q-for | CTCCAAAGCCAAAGGGCAGCCCCAGGAACCACAGGTGTACCCC | 33 |
| R344Q-rev | GGGTGTACACCTGTGGTTCCTGGGGCTGCCCTTTGGCTTTGGAG | 34 |
| R344E-for | CTCCAAAGCCAAAGGGCAGCCCGAGGAACCACAGGTGTACCCC | 35 |
| R344E-rev | GGGTGTACACCTGTGGTTCCTCGGGCTGCCCTTTGGCTTTGGAG | 36 |
| E356Q-for | CCCTGCCCCCATCCCGGCAGGAGATGACCAAGAACCAGG | 37 |
| E356Q-rev | CCTGGTTCTTGGTCATCTCCTGCCGGGATGGGGGCAGGG | 38 |
| E356K-for | CCCTGCCCCCATCCCGGAAGGAGATGACCAAGAACCAGG | 39 |
| E356K-rev | CCTGGTTCTTGGTCATCTCCTTCCGGGATGGGGGCAGGG | 40 |
| L398E-for | CAAGACCACGCCTCCCGTGGAGGACTCCGACGGCTCCTTCTTCC | 41 |
| L398E-rev | GGAAGAAGGAGCCGTCGGAGTCCTCCACGGGAGGCGTGGTCTTG | 42 |
| L398K-for | CAAGACCACGCCTCCCGTGAAGGACTCCGACGGCTCCTTCTTCC | 43 |
| L398K-rev | GGAAGAAGGAGCCGTCGGAGTCCTTCACGGGAGGCGTGGTCTTG | 44 |
| G341D-F | CCATCTCCAAAGCCAAAGACCAGCCCCGAGAACCACAGG | 45 |
| G341D-R | CCTGTGGTTCTCGGGGCTGGTCTTTGGCTTTGGAGATGG | 46 |
| G341K-F | CCATCTCCAAAGCCAAAAAGCAGCCCCGAGAACCACAGG | 47 |
| G341K-R | CCTGTGGTTCTCGGGGCTGCTTTTTGGCTTTGGAGATGG | 48 |
| M358E-F | CCCCCATCCCGGGAGGAGGAAACCAAGAACCAGGTCAGCC | 49 |
| M358E-R | GGCTGACCTGGTTCTTGGTTTCCTCCTCCCGGGATGGGG | 50 |
| M358K-F | CCCCCATCCCGGGAGGAGAAGACCAAGAACCAGGTCAGCC | 51 |
| M358K-R | GGCTGACCTGGTTCTTGGTCTTCTCCTCCCGGGATGGGG | 52 |
| T359E-F | CCATCCCGGGAGGAGATGGAGAAGAACCAGGTCAGCC | 53 |

TABLE 4-continued

Primers used for site directed mutagenesis

| Primer | Sequence‡ | SEQ ID NO. |
|---|---|---|
| T359E-R | GGCTGACCTGGTTCTTCTCCATCTCCTCCCGGGATGG | 54 |
| T359K-F | CCATCCCGGGAGGAGATGAAGAAGAACCAGGTCAGCC | 55 |
| T359K-R | GGCTGACCTGGTTCTTCTTCATCTCCTCCCGGGATGG | 56 |
| N361D-F | CCCGGGAGGAGATGACCAAGGACCAGGTCAGCCTGACCTGC | 57 |
| N361D-R | GCAGGTCAGGCTGACCTGGTCCTTGGTCATCTCCTCCCGGG | 58 |
| N361K-F | CCCGGGAGGAGATGACCAAGAAGCAGGTCAGCCTGACCTGC | 59 |
| N361K-R | GCAGGTCAGGCTGACCTGCTTCTTGGTCATCTCCTCCCGGG | 60 |
| N390D-F | GCAATGGGCAGCCGGAGAACGACTACAAGACCACGCCTCCCG | 61 |
| N390D-R | CGGGAGGCGTGGTCTTGTAGTCGTTCTCCGGCTGCCCATTGC | 62 |
| N390K-F | GCAATGGGCAGCCGGAGAACAAGTACAAGACCACGCCTCCCG | 63 |
| N390K-R | CGGGAGGCGTGGTCTTGTACTTGTTCTCCGGCTGCCCATTGC | 64 |

‡Underlined indicates location of mutation

Expression and Purification of Mutated anti-IL9 Antibodies: 293H cells were grown in Dulbecco's Modified Eagle Medium (DMEM) liquid (4.5 g/L D-glucose), with L-glutamine, and pyridoxine HCl, but no sodium pyruvate, plus 1% nonessential amino acids plus 10% fetal bovine serum. Transfections were performed by mixing 20 µg of each of the heavy and light chain vectors per T175 flask (two flasks were used per mutant) with 1.5 ml of Opti-MEM I. This mixture was then combined with 1.5 ml of Opti-MEM I containing 70 µl of Lipofectamine 2000 and left to sit at room temperature for ½ hour. Three mls of this mixture was added to a T175 containing 27 mls of DMEM plus 1% nonessential amino acids plus 5% ultra low bovine IgG fetal bovine serum. Three harvests were performed spaced three days apart. The harvested media was then spun at 1000 rpm and filtered through a 0.2 µm filter. Next, the antibodies were purified using protein A and were concentrated to between 0.1 and 1 mg/ml. Samples were dialyzed into 10 mM Histidine pH 6 and protein concentration adjusted to approximately 1 mg/ml.

Stability of Intact Antibodies: Intact antibodies were concentrated to 100 mg/ml in 10 mM Histidine pH 6. Samples were incubated at three temperatures 2-8° C., 23-27° C., and 38-42° C. and analyzed by SEC at predetermined time points. Samples were diluted to 10 mg/ml and 250 µg was injected onto the SEC column (see, SEC Analysis).

Stability of Fab and Fc Fragments: Fab and Fc fragments were isolated using papain digestion followed by column chromatography (also see, Example 1). The antibodies studied all had the same Fc region. Sample purity was analyzed and confirmed by SDS-PAGE and SEC. Fab and Fc fragments in 10 mM Histidine pH 6 were concentrated to 50 mg/ml. The concentrated material was incubated at 38-42° C. and sampled to monitor aggregate. The sample was diluted to 2 mg/ml and 70 µg was injected onto the SEC column (see, Size Exclusion Chromatography (SEC) Analysis).

Size Exclusion Chromatography (SEC) Analysis: SEC analysis was conducted on an Agilent 1100 High Performance Liquid Chromatography (HPLC) System with a flow rate of 1 mL/min. A TOSOH BIOSEP TSK G3000SW$_{XL}$ column (7.8 mm×30 cm) with guard column was used for the analysis. The mobile phase consisted of 100 mM Sodium Phosphate Dibasic Anhydrous, 100 mM Sodium Sulfate, and 0.05% Sodium Azide pH 6.8.

7. REFERENCES CITED

All references cited herein are incorporated herein by reference in their entirety and for all purposes to the same extent as if each individual publication or patent or patent application was specifically and individually indicated to be incorporated by reference in its entirety for all purposes. In addition, U.S. provisional Patent Application No. 60/696,113 filed Jul. 1, 2005 and 60/788,692 filed Apr. 4, 2006 are incorporated by reference in their entirety for all purposes.

Many modifications and variations of the present invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

The invention claimed is:

1. An engineered multidomain protein comprising an Fc domain, wherein the Fc domain has been modified to raise or lower the pI by replacing one or more amino acid residues in the Fc domain, wherein the modified Fc domain comprises an amino acid replacement selected from the group consisting of Q362D; Q362E; Q362K; and Q362R, as numbered by the EU index as set forth in Kabat.

2. The engineered multidomain protein of claim 1, wherein the Fc domain has been modified to increase the pI, and wherein the modified Fc domain comprises an amino acid replacement of Q362K or Q362R, as numbered by the EU index as set forth in Kabat.

3. The engineered multidomain protein of claim 2, wherein the amino acid replacement is Q362K, as numbered by the EU index as set forth in Kabat.

4. The engineered multidomain protein of claim 2, wherein the amino acid replacement is Q362R, as numbered by the EU index as set forth in Kabat.

5. The engineered multidomain protein of claim 2, wherein the modified Fc domain further comprises an amino acid replacement of E345K, as numbered by the EU index as set forth in Kabat.

6. The engineered multidomain protein of claim 5, wherein the modified Fc domain further comprises an amino acid replacement of D401K or D401N, as numbered by the EU index as set forth in Kabat.

7. The engineered multidomain protein of claim 2, wherein the modified Fc domain comprises an amino acid replacement selected from the group consisting of:
   a) E345K and Q362K and D401K; and
   b) E345K and Q362K and D401N;
   as numbered by the EU index as set forth in Kabat.

8. The engineered multidomain protein of claim 3, wherein the multidomain protein is an antibody.

9. The engineered multidomain protein of claim 3, wherein the multidomain protein is an Fc fusion protein.

10. The engineered multidomain protein of claim 4, wherein the multidomain protein is an antibody.

11. The engineered multidomain protein of claim 4, wherein the multidomain protein is an Fc fusion protein.

12. The engineered multidomain protein of claim 7, wherein the multidomain protein is an antibody.

13. The engineered multidomain protein of claim 7, wherein the multidomain protein is an Fc fusion protein.

14. The engineered multidomain protein of claim 1, wherein the Fc domain has been modified to decrease the pI, and wherein the modified Fc domain comprises an amino acid replacement of Q362D or Q362E, as numbered by the EU index as set forth in Kabat.

15. The engineered multidomain protein of claim 14, wherein the amino acid replacement is Q362D, as numbered by the EU index as set forth in Kabat.

16. The engineered multidomain protein of claim 14, wherein the amino acid replacement is Q362E, as numbered by the EU index as set forth in Kabat.

17. The engineered multidomain protein of claim 14, wherein the modified Fc domain further comprises an amino acid replacement of R355E, as numbered by the EU index as set forth in Kabat.

18. The engineered multidomain protein of claim 17, wherein the modified Fc domain further comprises an amino acid replacement of K340E or K340Q, as numbered by the EU index as set forth in Kabat.

19. The engineered multidomain protein of claim 14, wherein the modified Fc domain comprises an amino acid replacement selected from the group consisting of:
   a) R355E and Q362E;
   b) K340E and R355E and Q362E; and
   c) K340Q and R355E and Q362E;
   as numbered by the EU index as set forth in Kabat.

20. The engineered multidomain protein of claim 15, wherein the multidomain protein is an antibody.

21. The engineered multidomain protein of claim 15, wherein the multidomain protein is an Fc fusion protein.

22. The engineered multidomain protein of claim 16, wherein the multidomain protein is an antibody.

23. The engineered multidomain protein of claim 16, wherein the multidomain protein is an Fc fusion protein.

24. The engineered multidomain protein of claim 19, wherein the multidomain protein is an antibody.

25. The engineered multidomain protein of claim 19, wherein the multidomain protein is an Fc fusion protein.

* * * * *